US012643936B2

(12) United States Patent
Gottschalk et al.

(10) Patent No.: US 12,643,936 B2
(45) Date of Patent: Jun. 2, 2026

(54) CHIMERIC GMCSF-IL18 RECEPTOR

(71) Applicant: St. Jude Children's Research Hospital, Inc., Memphis, TN (US)

(72) Inventors: Stephen Gottschalk, Germantown, TN (US); Laurens Sand, Utrecht (NL); Shannon Lange, Memphis, TN (US)

(73) Assignee: ST. JUDE CHILDREN'S RESEARCH HOSPITAL, INC., Memphis, TN (US)

( * ) Notice: Subject to any disclaimer, the term of this patent is extended or adjusted under 35 U.S.C. 154(b) by 976 days.

(21) Appl. No.: 17/791,181

(22) PCT Filed: Jan. 6, 2021

(86) PCT No.: PCT/US2021/012307
§ 371 (c)(1),
(2) Date: Jul. 6, 2022

(87) PCT Pub. No.: WO2021/141986
PCT Pub. Date: Jul. 15, 2021

(65) Prior Publication Data
US 2023/0030680 A1     Feb. 2, 2023

Related U.S. Application Data

(60) Provisional application No. 62/958,037, filed on Jan. 7, 2020.

(51) Int. Cl.
| | |
|---|---|
| *C07K 14/715* | (2006.01) |
| *A61K 40/11* | (2025.01) |
| *A61K 40/31* | (2025.01) |
| *A61K 40/42* | (2025.01) |
| *A61K 38/00* | (2006.01) |

(52) U.S. Cl.
CPC .......... *C07K 14/7153* (2013.01); *A61K 40/11* (2025.01); *A61K 40/31* (2025.01); *A61K 40/4205* (2025.01); *A61K 40/4217* (2025.01); *A61K 40/422* (2025.01); *C07K 14/7155* (2013.01); *A61K 38/00* (2013.01); *A61K 2239/31* (2023.05); *A61K 2239/38* (2023.05); *A61K 2239/46* (2023.05); *C07K 2319/03* (2013.01)

(58) Field of Classification Search
CPC ..... C07K 14/7153; A61K 40/11; A61K 40/31
See application file for complete search history.

(56) References Cited

U.S. PATENT DOCUMENTS

| | | |
|---|---|---|
| 5,747,292 A | 5/1998 | Greenberg et al. |
| 2008/0206189 A1 | 8/2008 | Bam et al. |
| 2012/0141464 A1 | 6/2012 | Cohen et al. |
| 2016/0075755 A1 | 3/2016 | Valdes et al. |
| 2019/0127435 A1 | 5/2019 | Schmitt et al. |

OTHER PUBLICATIONS

International Search Report and Written Opinion mailed Apr. 7, 2021 for International Patent Application No. PCT/US2021/012307 (Applicant: St. Jude Children's Research Hospital, Inc.) (15 pages).
Dinarello, et al., Interleukin-18 and IL-18 binding protein, Frontiers in Immunology, Oct. 8, 2013, www.frontiersin.org, vol. 4, Article 289.
Hercus, et al., The granulocyte-macrophage colony-stimulating factor receptor: linking its structure to cell signaling and its role in disease, Blood, Aug. 13, 2009, vol. 114, No. 7.
Hansen, et al., The Structure of the GM-CSF Receptor Complex Reveals a Distinct Mode of Cytokine Receptor Activation, Cell, Aug. 8, 2008, 496-507.
Evans, et al., Expression of Chimeric Granulocyte-Macrophage Colony-Stimulating Factor/Interleukin 2 Receptors in Human Cytotoxic T Lymphocyte Clones Results in Granulocyte-Macrophage Colony-Stimulating Factor-Dependent Growth, Chimeric Cytokine Receptors, www.liebertpub.com, May 19, 1999.

*Primary Examiner* — Valarie E Bertoglio
(74) *Attorney, Agent, or Firm* — Troutman Pepper Locke LLP

(57)     ABSTRACT

The present invention provides chimeric cytokine receptors, particularly chimeric cytokine receptors that can be activated in tumor microenvironment, and their uses in tumor immunotherapy (e.g., adoptive cell therapy). The present invention further provides methods of genetically modifying therapeutic cells resulting in an enhanced immune response against a target antigen. The application further provides therapeutic cells that express said chimeric cytokine receptors and methods for treating patients using the modified therapeutic cells.

44 Claims, 21 Drawing Sheets
Specification includes a Sequence Listing.

GM-CSFR (CD116)

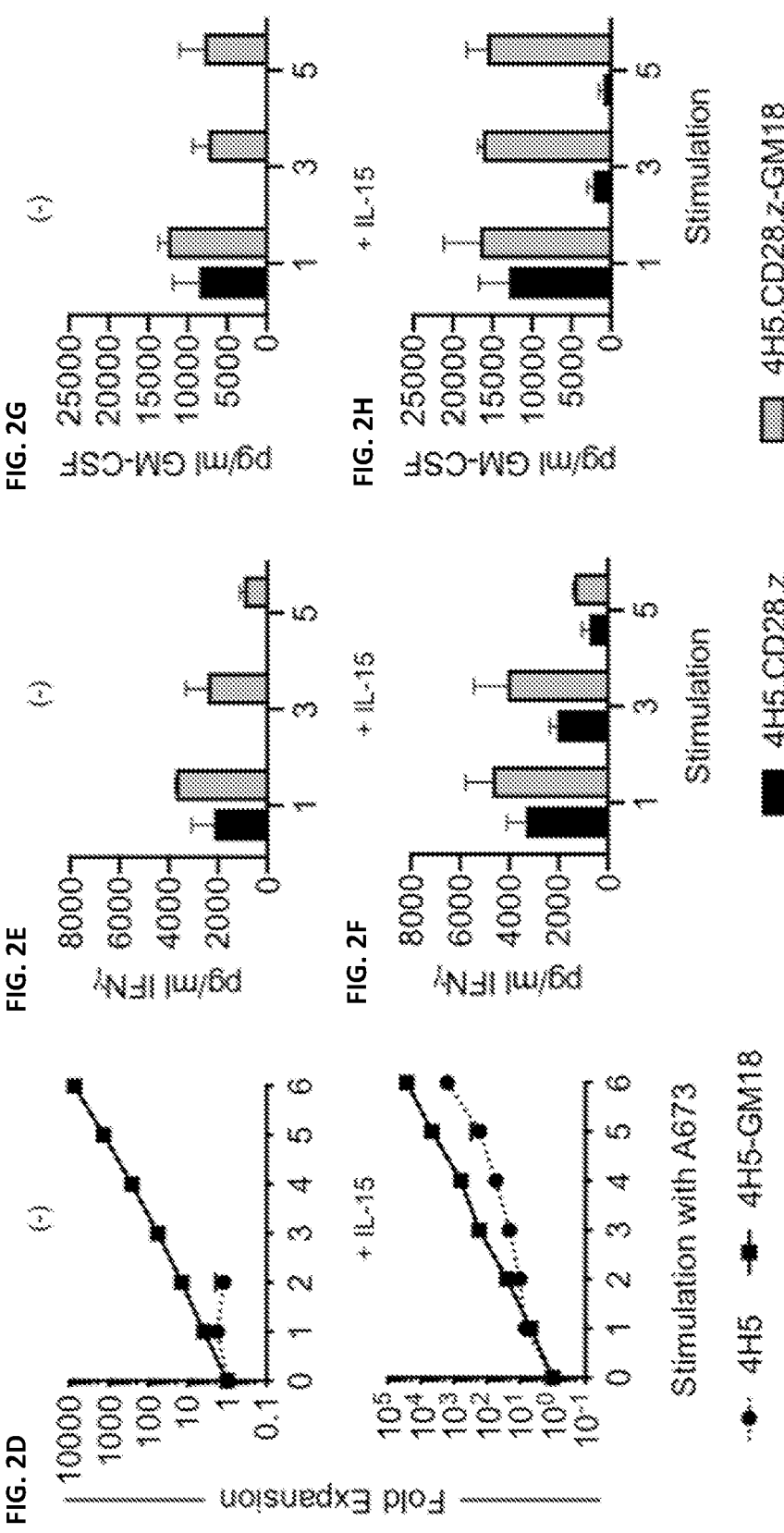

Dotted line: tumor only
Solid line: FRP5-CD28.z
Grey line: FRP5-CD28.z-GM18

Percent survival

Day post T cell injection

NSG
(7-9wk old)

Tumor cells
LM7-ffLuc
1x10⁶ i.p.

HER2-CAR
T cells
3x10⁵ i.v.

FIG. 6A

GM18 Nucleotide sequence:

*Leader sequence GMCSFR beta*
ATGGTTCTGGCCCAGGGCCTGCTGTCTATGGCTCTGCTTGCTCTGTGC (SEQ ID NO: 16)

*GMCSFR beta isoform 2 extracellular domain (P32927-2)*
TGGGAGAGAAGTCTGGCTGGCGCCGAGGAAACAATCCCTCTGCAGACCCTGCGGT
GCTACAACGACTACACCAGCCACATCACCTGTAGATGGGCCGACACACAGGACGC
CCAGAGACTGGTCAATGTGACCCTGATCAGAAGAGTGAACGAGGACCTGCTGGAAC
CCGTGTCCTGTGACCTGAGCGACGATATGCCTTGGAGCGCCTGTCCTCATCCTAGA
TGTGTGCCTCGGAGATGCGTGATCCCCTGCCAGAGCTTTGTGGTCACCGATGTGGA
CTACTTCAGCTTCCAGCCTGACAGACCCCTGGGCACCAGACTGACAGTGACACTGA
CACAGCACGTGCAGCCTCCAGAGCCTAGGGACCTGCAGATCTCTACCGACCAGGA
CCACTTCCTGCTGACTTGGAGTGTGGCCCTGGGAAGCCCTCAGTCTCATTGGCTTA
GCCCTGGCGACCTGGAATTCGAGGTGGTGTACAAGAGACTGCAGGACAGCTGGGA
AGATGCCGCCATCCTGCTGAGCAATACCAGCCAGGCTACACTGGGCCCCGAACAC
CTGATGCCTAGCTCTACCTATGTGGCCAGAGTGCGGACAAGACTGGCCCCTGGATC
TAGACTGAGCGGCAGACCTTCTAAGTGGTCCCCTGAAGTCTGCTGGGATAGCCAGC
CTGGGGATGAAGCCCAGCCTCAGAACCTGGAATGCTTCTTCGATGGCGCCGCTGT
GCTGAGCTGTTCTTGGGAAGTGCGGAAAGAGGTGGCCAGCAGCGTTAGCTTCGGC
CTGTTCTACAAGCCCTCTCCAGATGCCGGATCTGCCGTGCTGCTGAGAGAAGAGGA
ATGCAGCCCCGTGCTCAGAGAAGGCCTGGGATCTCTGCACACCAGACACCACTGT
CAGATCCCCGTGCCTGATCCTGCCACACACGGCCAGTATATCGTGTCCGTGCAGCC
AAGAAGGGCCGAGAAGCACATCAAGAGCAGCGTGAACATCCAGATGGCCCCTCCA
AGCCTGAACGTGACCAAGGACGGCGACAGCTACAGCCTGAGATGGGAGACAATGA
AGATGCGCTACGAGCACATCGACCACACCTTCGAGATCCAGTACCGGAAGGATACC
GCCACCTGGAAGGACAGCAAGACCGAGACACTGCAGAACGCCCACTCTATGGCAC
TGCCAGCTCTCGAGCCCTCCACCAGATATTGGGCCAGAGTCAGAGTGCGGACCAG
CAGAACAGGCTACAACGGCATTTGGAGCGAGTGGAGCGAAGCCAGAAGCTGGGAT
ACAGAGTCTGTACTACCAATGTGG (SEQ ID NO: 8)

*IL-18R beta TM domain \*altered – 3 bp missing (O95256)*
GGCGTGCTGCTGTACATCCTGCTGGGCACAATCGGAACACTGGTGGCTGTGCTGG
CTGCC (SEQ ID NO: 10)

*IL-18R beta intracellular domain (O95256)*
AGCGCTCTGCTGTATAGACACTGGATCGAGATCGTCCTGCTGTACCGGACCTACCA
GAGCAAGGATCAGACCCTGGGCGACAAGAAGGACTTCGACGCCTTTGTGTCCTAC
GCCAAGTGGTCCAGCTTTCCCAGCGAGGCCACAAGCAGCCTGAGCGAAGAACATC
TGGCCCTGTCTCTGTTCCCCGATGTGCTGGAAAACAAATACGGCTACAGCCTGTGC
CTGCTGGAAAGAGATGTTGCCCCTGGCGGAGTGTACGCCGAGGATATCGTGTCCAT
CATCAAGCGGAGCAGACGGGGCATCTTCATTCTGAGCCCCAACTACGTGAACGGC
CCCAGCATCTTTGAACTGCAAGCCGCCGTGAACCTGGCTCTGGACGATCAGACACT
GAAGCTGATCCTGATCAAGTTCTGCTACTTCCAAGAGCCTGAGAGCCTGCCTCACC
TGGTCAAGAAAGCCCTGAGAGTGCTGCCTACCGTGACTTGGAGAGGCCTGAAGTC
CGTGCCTCCTAACAGCAGATTCTGGGCCAAGATGAGATACCACATGCCTGTGAAGA
ACAGCCAGGGCTTCACCTGGAACCAGCTGCGGATCACCTCCAGAATCTTCCAGTGG
AAGGGCCTGAGCCGGACCGAGACAACAGGCAGAAGCAGCCAGCCTAAAGAGTGG
(SEQ ID NO: 12)

FIG. 6B

GM18 Nucleotide sequence (cont'd):

*T2A sequence*
GGCTCCGGAGAGGGCAGAGGCAGCCTGCTGACATGTGGCGACGTGGAAGAGAA
CCCAGGCCCA (SEQ ID NO: 22)

*Leader sequence GMCSFR alpha*
ATGCTGCTGCTGGTCACATCTCTGCTGCTGTGCGAGCTGCCCCATCCTGCCTTTC
TGCTGATCCCC (SEQ ID NO: 14)

*GMCSFR alpha extracellular domain (P15509)*
GAGAAGTCCGACCTGAGAACAGTGGCCCCTGCCAGCTCTCTGAACGTTCGCTTC
GACAGCCGGACCATGAACCTGAGCTGGGACTGCCAAGAGAACACAACCTTCAGC
AAGTGCTTCCTGACCGACAAGAAGAACCGGGTCGTCGAGCCCAGACTGAGCAAC
AATGAGTGCTCCTGCACCTTCAGAGAGATCTGCCTGCACGAGGGCGTGACCTTT
GAGGTGCACGTGAACACAAGCCAGCGGGGCTTTCAGCAGAAGCTGCTGTACCC
CAATAGCGGCAGAGAGGGAACCGCCGCTCAGAACTTCAGCTGCTTCATCTACAA
CGCCGACCTCATGAACTGCACCTGGGCCAGAGGACCTACCGCTCCTAGAGATGT
GCAGTACTTCCTGTACATTCGGAACAGCAAGCGGCGGAGAGAAATCAGGTGCCC
CTACTACATCCAAGACAGCGGCACACACGTGGGCTGCCACCTGGATAATCTGTC
TGGCCTGACCAGCCGGAACTACTTCCTGGTCAATGGCACCAGCCGCGAGATCGG
CATCCAGTTCTTTGACAGCCTGCTGGACACCAAGAAGATCGAGCGGTTCAACCCT
CCTAGCAACGTGACCGTGCGGTGCAACACCACACATTGTCTCGTGCGGTGGAAG
CAGCCCCGGACATACCAGAAGCTGAGCTACCTGGACTTCCAGTACCAGCTGGAT
GTGCACCGGAAGAACACCCAGCCTGGCACCGAGAACCTGCTGATCAATGTGTCC
GGCGACCTGGAAAACCGGTACAACTTCCCTAGCAGCGAGCCCAGGGCCAAGCA
CAGCGTGAAAATTAGAGCCGCCGATGTGCGCATCCTGAACTGGTCCTCTTGGAG
CGAGGCCATCGAGTTTGGATCCGACGACGGC (SEQ ID NO: 2)

*IL-18R alpha TM domain (Q13478)*
ATGATCATTGCCGTGCTGATCCTGGTGGCCGTCGTGTGTCTGGTCACCGTGTGC
GTGATC (SEQ ID NO: 4)

*IL-18R alpha intracellular domain (Q13478)*
TACAGAGTGGACCTGGTGCTGTTCTACCGGCACCTGACCAGAAGGGACGAGACA
CTGACCGACGGCAAGACCTACGATGCCTTCGTGTCCTACCTGAAAGAGTGCAGA
CCCGAGAACGGCGAGGAACACACCTTCGCCGTGGAAATCCTGCCTAGAGTGCTG
GAAAAGCACTTCGGCTACAAGCTGTGCATCTTCGAGAGGGACGTTGTGCCTGGC
GGAGCTGTGGTGGATGAGATCCACAGCCTGATCGAGAAGTCCAGACGGCTGATC
ATCGTGCTGAGCAAGAGCTACATGAGCAACGAAGTCCGCTACGAGCTGGAAAGC
GGACTGCACGAAGCCCTGGTGGAACGGAAGATCAAGATCATCCTGATTGAGTTC
ACCCCTGTGACCGACTTCACATTCCTGCCTCAGAGCCTGAAGCTGCTGAAGTCC
CACAGAGTGCTGAAGTGGAAGGCCGACAAGAGCCTGAGCTACAACAGCCGGTTC
TGGAAGAACCTGCTGTACCTGATGCCTGCCAAGACCGTGAAGCCCGGCAGAGAT
GAACCTGAGGTGCTGCCTGTGCTGAGCGAGTCTTAA (SEQ ID NO: 6)

FIG. 6C

GM18 amino acid sequence:

*Leader sequence GMCSFR beta*
MVLAQGLLSMALLALC (SEQ ID NO: 15)

*GMCSFR beta isoform 2 extracellular domain (P32927-2)*
WERSLAGAEETIPLQTLRCYNDYTSHITCRWADTQDAQRLVNVTLIRRVNEDLLEPV
SCDLSDDMPWSACPHPRCVPRRCVIPCQSFVVTDVDYFSFQPDRPLGTRLTVTLT
QHVQPPEPRDLQISTDQDHFLLTWSVALGSPQSHWLSPGDLEFEVVYKRLQDSWE
DAAILLSNTSQATLGPEHLMPSSTYVARVRTRLAPGSRLSGRPSKWSPEVCWDSQ
PGDEAQPQNLECFFDGAAVLSCSWEVRKEVASSVSFGLFYKPSPDAGSAVLLREE
ECSPVLREGLGSLHTRHHCQIPVPDPATHGQYIVSVQPRRAEKHIKSSVNIQMAPP
SLNVTKDGDSYSLRWETMKMRYEHIDHTFEIQYRKDTATWKDSKTETLQNAHSMA
LPALEPSTRYWARVRVRTSRTGYNGIWSEWSEARSWDTESVLPMW (SEQ ID NO:
7)

*IL-18R beta TM domain \*altered – 3 bp missing (O95256)*
GVLLYILLGTIGTLVAVLAA (SEQ ID NO: 9)

*IL-18R beta intracellular domain (O95256)*
SALLYRHWIEIVLLYRTYQSKDQTLGDKKDFDAFVSYAKWSSFPSEATSSLSEEHLA
LSLFPDVLENKYGYSLCLLERDVAPGGVYAEDIVSIIKRSRRGIFILSPNYVNGPSIFE
LQAAVNLALDDQTLKLILIKFCYFQEPESLPHLVKKALRVLPTVTWRGLKSVPPNSRF
WAKMRYHMPVKNSQGFTWNQLRITSRIFQWKGLSRTETTGRSSQPKEW (SEQ ID
NO: 11)

*T2A sequence*
GSGEGRGSLLTCGDVEENPGP (SEQ ID NO: 21)

*Leader sequence GMCSFR alpha*
MLLLVTSLLLCELPHPAFLLIP (SEQ ID NO: 13)

*GMCSFR alpha extracellular domain (P15509)*
EKSDLRTVAPASSLNVRFDSRTMNLSWDCQENTTFSKCFLTDKKNRVVEPRLSNN
ECSCTFREICLHEGVTFEVHVNTSQRGFQQKLLYPNSGREGTAAQNFSCFIYNADL
MNCTWARGPTAPRDVQYFLYIRNSKRRREIRCPYYIQDSGTHVGCHLDNLSGLTSR
NYFLVNGTSREIGIQFFDSLLDTKKIERFNPPSNVTVRCNTTHCLVRWKQPRTYQKL
SYLDFQYQLDVHRKNTQPGTENLLINVSGDLENRYNFPSSEPRAKHSVKIRAADVRI
LNWSSWSEAIEFGSDDG (SEQ ID NO: 1)

*IL-18R alpha TM domain (Q13478)*
MIIAVLILVAVVCLVTVCVI (SEQ ID NO: 3)

*IL-18R alpha intracellular domain (Q13478)*
YRVDLVLFYRHLTRRDETLTDGKTYDAFVSYLKECRPENGEEHTFAVEILPRVLEKH
FGYKLCIFERDVVPGGAVVDEIHSLIEKSRRLIIVLSKSYMSNEVRYELESGLHEALV
ERKIKIILIEFTPVTDFTFLPQSLKLLKSHRVLKWKADKSLSYNSRFWKNLLYLMPAKT
VKPGRDEPEVLPVLSES\* (SEQ ID NO: 5)

FIG. 7A
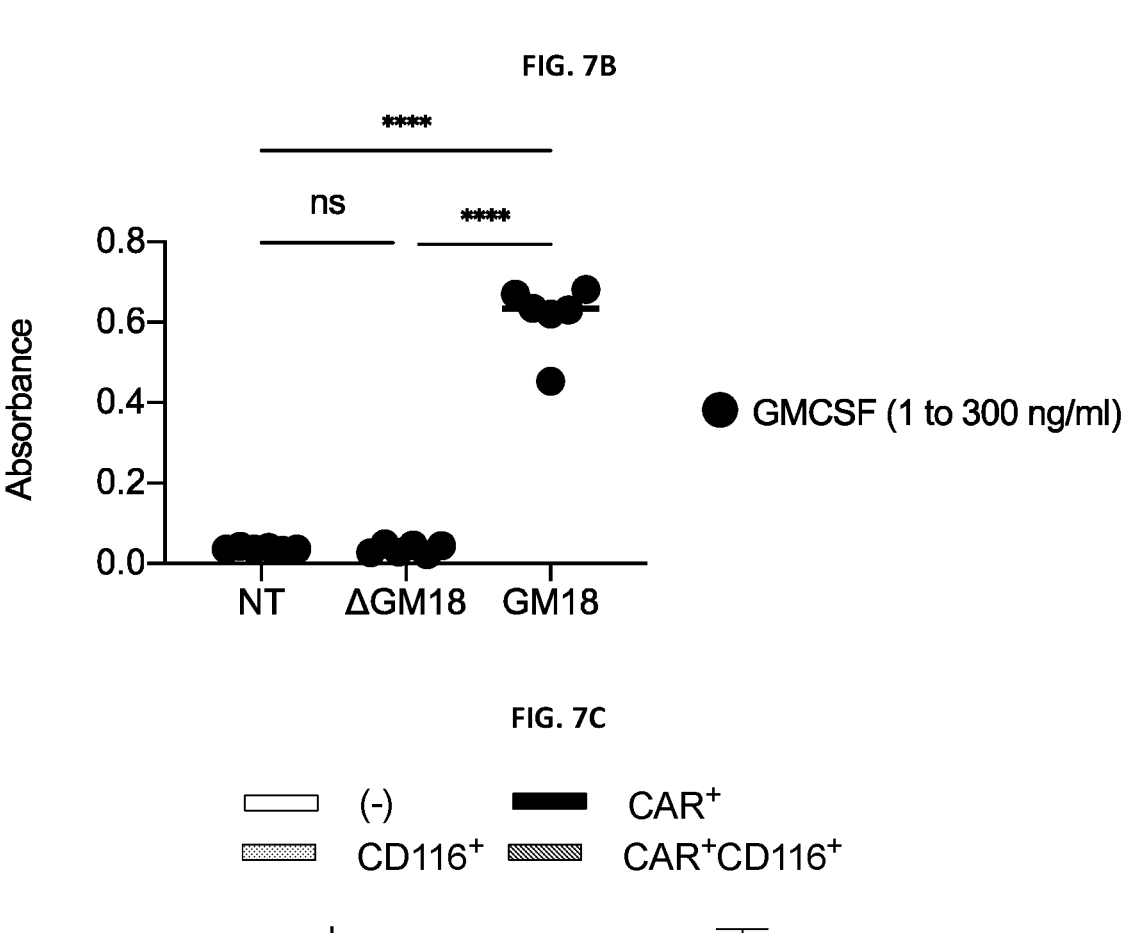
FIG. 7B
FIG. 7C
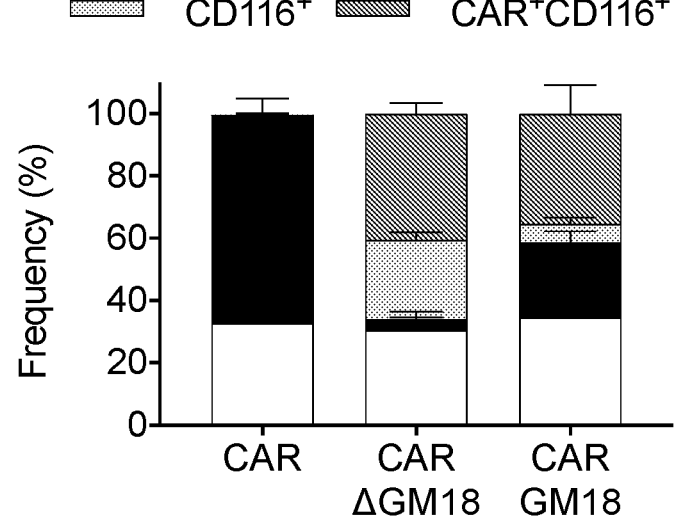

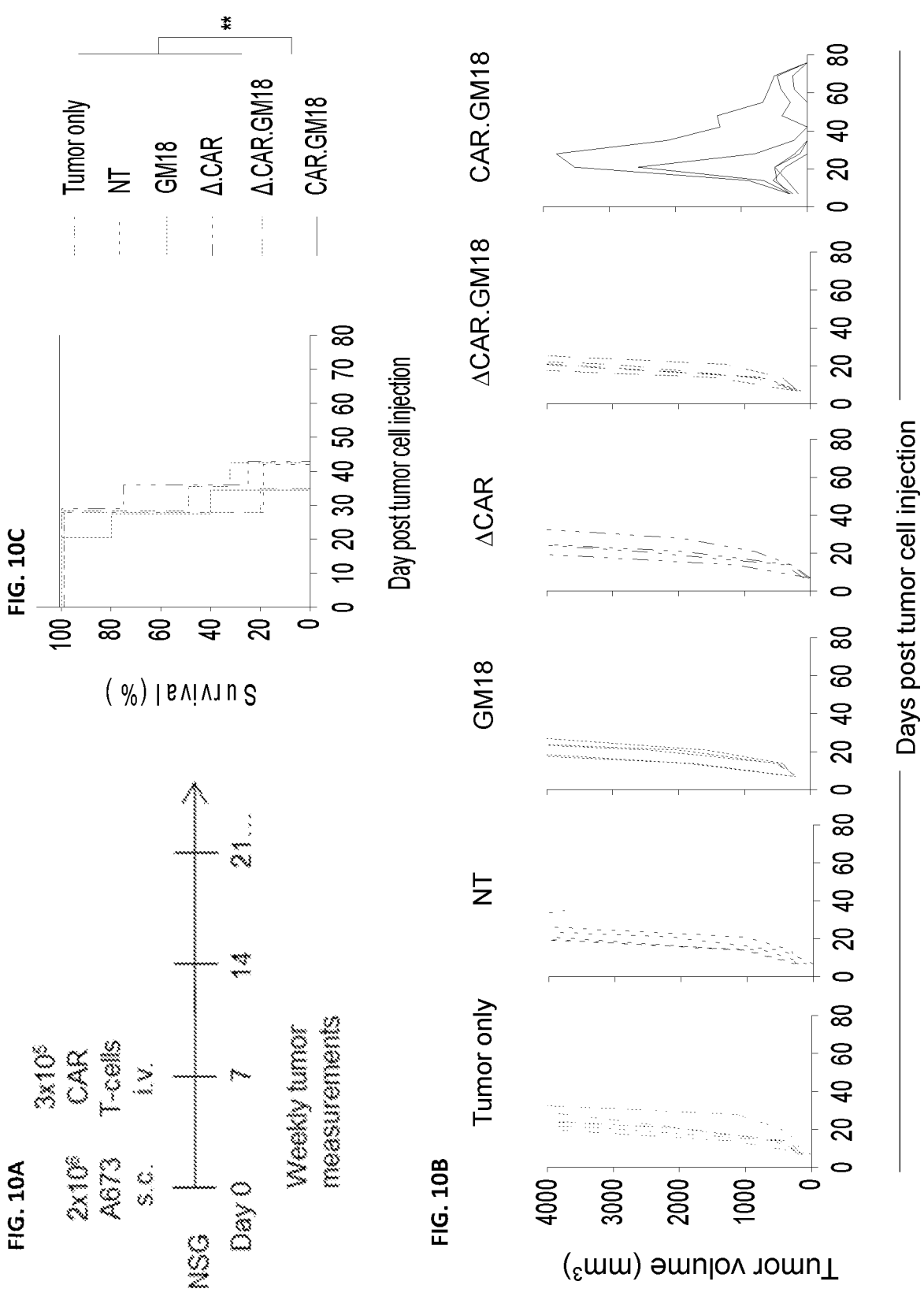

CHIMERIC GMCSF-IL18 RECEPTOR

CROSS-REFERENCE TO RELATED APPLICATIONS

This application is a National Stage Application of International Application No. PCT/US21/12307, filed Jan. 6, 2021, which claims priority to U.S. Provisional Application No. 62/958,037, filed Jan. 7, 2020, all of which are herein incorporated by reference in its entirety their entireties.

SEQUENCE LISTING

The instant application contains a Sequence Listing which has been submitted electronically in ASCII format and is hereby incorporated by reference in its entirety. Said ASCII copy, created on Jan. 5, 2021, is named 243734_000143_SL.txt and is 87,926 bytes in size.

FIELD OF THE INVENTION

The application relates to chimeric cytokine receptors, particularly chimeric cytokine receptors that can be activated in the tumor microenvironment, and their uses in tumor immunotherapy (e.g., adoptive cell therapy). The application further relates to methods of genetically modifying therapeutic immune cells resulting in an enhanced immune response against a target antigen. The application further relates to therapeutic cells that express said chimeric cytokine receptors and methods for treating patients using the modified therapeutic cells.

BACKGROUND

Immunotherapy, particularly chimeric antigen receptor (CAR) T cells, has emerged as a promising treatment option for various cancers following its success for the treatment of B cell hematological malignancies. However, the solid tumor microenvironment (TME) has presented many challenges to the efficacy and persistence of therapeutic immune cells, in part due to lack of immune cell-supportive cytokines at the tumor site. Accordingly, there is a need for means to improve efficacy and persistence of therapeutic cells used in immunotherapy.

SUMMARY OF THE INVENTION

The present invention provides, among other things, chimeric cytokine receptors that can be activated in the tumor microenvironment. The chimeric cytokine receptors when expressed in a therapeutic immune cell, can enhance the effector function (e.g., expansion, persistence and/or tumor killing activity) of the immune cell.

In one aspect, the present disclosure provides a polynucleotide encoding a chimeric cytokine receptor, said chimeric cytokine receptor comprising an extracellular domain of granulocyte-macrophage colony-stimulating factor (GM-CSF) receptor, or a functional portion thereof, a transmembrane domain, and an intracellular domain of interleukin-18 receptor (IL-18) receptor, or a functional portion thereof.

In one aspect, the present disclosure provides a chimeric cytokine receptor, comprising an extracellular domain of granulocyte-macrophage colony-stimulating factor (GM-CSF) receptor, or a functional portion thereof, a transmembrane domain, and an intracellular domain of interleukin-18 receptor (IL-18) receptor, or a functional portion thereof.

In some embodiments, the chimeric cytokine receptor comprises i. a first polypeptide comprising an extracellular region of GM-CSF receptor α chain, or a functional portion thereof, a first transmembrane region, and an intracellular region of IL-18 receptor α chain, or a functional portion thereof; and ii. a second polypeptide comprising an extracellular region of GM-CSF receptor β chain, or a functional portion thereof, a second transmembrane region, and an intracellular region of IL-18 receptor β chain, or a functional portion thereof.

In some embodiments, the chimeric cytokine receptor comprises i. a first polypeptide comprising an extracellular region of GM-CSF receptor α chain, or a functional portion thereof, a first transmembrane region, and an intracellular region of IL-18 receptor β chain, or a functional portion thereof, and ii. a second polypeptide comprising an extracellular region of GM-CSF receptor β chain, or a functional portion thereof, a second transmembrane region, and an intracellular region of IL-18 receptor α chain, or a functional portion thereof.

In one embodiment, the extracellular region of GM-CSF receptor α chain comprises the amino acid sequence of SEQ ID NO: 1, or an amino acid sequence having at least 80% sequence identity thereof.

In one embodiment, the sequence encoding the extracellular region of GM-CSF receptor α chain comprises the nucleotide sequence of SEQ ID NO: 2, or a nucleotide sequence having at least 80% sequence identity thereof.

In one embodiment, the intracellular region of IL-18 receptor α chain comprises the amino acid sequence of SEQ ID NO: 5, or an amino acid sequence having at least 80% sequence identity thereof.

In one embodiment, the sequence encoding the intracellular region of IL-18 receptor α chain comprises the nucleotide sequence of SEQ ID NO: 6, or a nucleotide sequence having at least 80% sequence identity thereof.

In one embodiment, the extracellular region of GM-CSF receptor β chain comprises the amino acid sequence of SEQ ID NO: 7, or an amino acid sequence having at least 80% sequence identity thereof.

In one embodiment, the sequence encoding the extracellular region of GM-CSF receptor β chain comprises the nucleotide sequence of SEQ ID NO: 8, or a nucleotide sequence having at least 80% sequence identity thereof.

In one embodiment, the intracellular region of IL-18 receptor β chain comprises the amino acid sequence of SEQ ID NO: 11, or an amino acid sequence having at least 80% sequence identity thereof.

In one embodiment, the sequence encoding the intracellular region of IL-18 receptor β chain comprises the nucleotide sequence of SEQ ID NO: 12, or a nucleotide sequence having at least 80% sequence identity thereof.

In one embodiment, at least one of the transmembrane regions is derived from a transmembrane domain of IL-18 receptor or GM-CSF receptor.

In one embodiment, the first transmembrane region comprises a transmembrane region of IL-18 receptor α chain.

In one embodiment, the transmembrane region of IL-18 receptor α chain comprises the amino acid sequence of SEQ ID NO: 3, or an amino acid sequence having at least 80% sequence identity thereof.

In one embodiment, the sequence encoding the transmembrane region of IL-18 receptor α chain comprises the nucleotide sequence of SEQ ID NO: 4, or a nucleotide sequence having at least 80% sequence identity thereof.

In one embodiment, the second transmembrane region comprises a transmembrane region of IL-18 receptor β chain.

In one embodiment, the transmembrane region of IL-18 receptor β chain comprises the amino acid sequence of SEQ ID NO: 9, or an amino acid sequence having at least 80% sequence identity thereof.

In one embodiment, the sequence encoding the transmembrane region of IL-18 receptor β chain comprises the nucleotide sequence of SEQ ID NO: 10, or a nucleotide sequence having at least 80% sequence identity thereof.

In some embodiments, the first polypeptide further comprises a first leader sequence.

In one embodiment, the first leader sequence is derived from a leader sequence of GM-CSF receptor α chain.

In one embodiment, the first leader sequence comprises the amino acid sequence of SEQ ID NO: 13, 44 or 46, or an amino acid sequence having at least 80% sequence identity thereof.

In one embodiment, the nucleotide encoding the first leader sequence comprises the nucleotide sequence of SEQ ID NO: 14, 45 or 47, or a nucleotide sequence having at least 80% sequence identity thereof.

In some embodiments, the second polypeptide further comprises a second leader sequence.

In one embodiment, the second leader sequence is derived from a leader sequence of GM-CSF receptor β chain.

In one embodiment, the second leader sequence comprises the amino acid sequence of SEQ ID NO: 15, 44 or 46, or an amino acid sequence having at least 80% sequence identity thereof.

In one embodiment, the nucleotide encoding the second leader sequence comprises the nucleotide sequence of SEQ ID NO: 16, 45 or 47, or a nucleotide sequence having at least 80% sequence identity thereof.

In one embodiment, the first polypeptide comprises the amino acid sequence of SEQ ID NO: 17, or an amino acid sequence having at least 80% sequence identity thereof.

In one embodiment, the sequence encoding the first polypeptide comprises the nucleotide sequence of SEQ ID NO: 18, or a nucleotide sequence having at least 80% sequence identity thereof.

In one embodiment, the second polypeptide comprises the amino acid sequence of SEQ ID NO: 19, or an amino acid sequence having at least 80% sequence identity thereof.

In one embodiment, the sequence encoding the second polypeptide comprises the nucleotide sequence of SEQ ID NO: 20, or a nucleotide sequence having at least 80% sequence identity thereof.

In some embodiments, the sequence encoding the first polypeptide is operably linked to the sequence encoding a second polypeptide via a sequence encoding a self-cleaving peptide or an internal ribosomal entry site (IRES).

In some embodiments, the self-cleaving peptide is a 2A peptide. In some embodiments, the 2A peptide is T2A, P2A, E2A, or F2A peptide.

In one embodiment, the self-cleaving 2A peptide comprises the amino acid sequence of SEQ ID NO: 21, or an amino acid sequence having at least 80% sequence identity thereof.

In one embodiment, the sequence encoding the self-cleaving 2A peptide comprises the nucleotide sequence of SEQ ID NO: 22, or a nucleotide sequence having at least 80% sequence identity thereof.

In one embodiment, the chimeric cytokine receptor comprises the amino acid sequence of SEQ ID NO: 23, or an amino acid sequence having at least 80% sequence identity thereof.

In one embodiment, the polynucleotide comprises the nucleotide sequence of SEQ ID NO: 24, or a nucleotide sequence having at least 80% sequence identity thereof.

In another aspect, provided herein is a polynucleotide encoding the first polypeptide of the chimeric cytokine receptor of any one of those described above.

In another aspect, provided herein is a polynucleotide encoding the second polypeptide of the chimeric cytokine receptor of any one of those described above.

In various embodiments, the polynucleotide encoding a chimeric cytokine receptor (or the first or second polypeptide of the chimeric cytokine receptor) described herein is a DNA molecule.

In various embodiments, the polynucleotide encoding a chimeric cytokine receptor (or the first or second polypeptide of the chimeric cytokine receptor) described herein is an RNA molecule.

In another aspect, the present disclosure also provides a recombinant vector comprising the polynucleotide encoding a chimeric cytokine receptor (or the first or second polypeptide of the chimeric cytokine receptor) described herein.

In some embodiments, the vector is a viral vector. In some embodiments, the viral vector is a retroviral vector, a lentiviral vector, an adenoviral vector, an adeno-associated viral (AAV) vector, a herpes viral vector, or a baculoviral vector. In one embodiment, the viral vector is a retroviral vector.

In some embodiments, the vector is a non-viral vector. In some embodiments, the non-viral vector is a minicircle plasmid, a Sleeping Beauty transposon, a piggyBac transposon, or a single or double stranded DNA molecule that is used as a template for homology directed repair (HDR) based gene editing.

In another aspect, the present disclosure also provides a chimeric cytokine receptor encoded by the polynucleotide described herein.

In another aspect, the present disclosure also provides an isolated host cell comprising the polynucleotide or the recombinant vector described herein.

In another aspect, the present disclosure also provides an isolated host cell comprising the chimeric cytokine receptor described herein.

In some embodiments, the cell further expresses a chimeric antigen receptor (CAR), an antigen specific T cell receptor (TCR) or a bispecific antibody.

In some embodiments, the CAR, TCR or bispecific antibody specifically binds a tumor antigen. In some embodiments, the tumor antigen is selected from carbonic anhydrase EX, alpha-fetoprotein, A3, antigen specific for A33 antibody, Ba 733, BrE3-antigen, CA125, CD1, CD1a, CD3, CD5, CD15, CD16, CD19, CD20, CD21, CD22, CD23, CD25, CD30, CD33, CD38, CD45, CD74, CD79a, CD80, CD123, CD138, colon-specific antigen-p (CSAp), CEA (CEACAM5), CEACAM6, CSAp, EGFR, EGP-I, EGP-2, Ep-CAM, EphA1, EphA2, EphA3, EphA4, EphA5, EphA6, EphA7, EphA8, EphA10, EphB1, EphB2, EphB3, EphB4, EphB6, Flt-I, Flt-3, folate receptor, HLA-DR, human chorionic gonadotropin (HCG) and its subunits, human epidermal growth factor receptor 2 (HER2), hypoxia inducible factor (HIF-I), Ia, IL-2, IL-6, IL-8, interleukin 13 receptor α2 (IL13Rα2), insulin growth factor-1 (IGF-I), KC4-antigen, KS-1-antigen, KS1-4, Le-Y, macrophage inhibition factor (MIF), MAGE, MUC1, MUC2, MUC3, MUC4, NCA66, NCA95, NCA90, antigen specific for PAM-4 antibody, placental growth factor, p53, prostatic acid phosphatase, PSA, PSMA, RS5, S100, TAC, TAG-72, tenascin, TRAIL receptors, Tn antigen, Thomson-Friedenreich antigens, tumor necrosis antigens, VEGF, and fibronectin-EDB (oncofetal fibronectin, FN-EDB, EDB).

In some embodiments, the cell comprises a CAR that specifically binds human epidermal growth factor receptor 2 (HER2). In one embodiment, the HER2 CAR comprises the amino acid sequence of SEQ ID NO: 26, or an amino acid sequence having at least 80% sequence identity thereof. In one embodiment, the sequence encoding the HER2 CAR comprises the nucleotide sequence of SEQ ID NO: 27, or a nucleotide sequence having at least 80% sequence identity thereof.

In some embodiments, the cell comprises a CAR that specifically binds ephrin type-A receptor 2 (EphA2). In one embodiment, the EphA2 CAR comprises the amino acid sequence of SEQ ID NO: 28, or an amino acid sequence having at least 80% sequence identity thereof. In one embodiment, the sequence encoding the EphA2 CAR comprises the nucleotide sequence of SEQ ID NO: 29, or a nucleotide sequence having at least 80% sequence identity thereof.

In some embodiments, the CAR comprises one or more co-stimulatory domains selected from 4-1BB (CD137), CD28, CD40, ICOS, CD134 (OX-40), BTLA, CD27, CD30, GITR, CD226, CD79A, MyD88, CD40 and HVEM.

In various embodiments, the cell is an immune cell. In various embodiments, the cell expresses GM-CSF upon activation.

In various embodiments, the cell is a T cell. In some embodiments, the T cell is an αβ TCR T cell, a γδ T cell, or an iNKT cell.

In various embodiments, the cell is a nature killer (NK) cell.

In various embodiments, the host cell has been activated and/or expanded ex vivo.

In various embodiments, the host cell is an allogeneic cell. In various embodiments, the host cell is an autologous cell.

In another aspect, the present disclosure provides a pharmaceutical composition comprising the host cell described herein and a pharmaceutically acceptable carrier and/or excipient.

In another aspect, the present disclosure provides a method of enhancing effector function of an immune cell, wherein the immune cell expresses a chimeric antigen receptor (CAR), an antigen specific T cell receptor (TCR) and/or a bispecific antibody, comprising genetically modifying the cell with a polynucleotide described herein or a recombinant vector described herein. In some embodiments, the effector function is one or more of expansion, persistence, and/or tumor killing activity.

In another aspect, the present disclosure provides a method of generating the isolated host cell described herein, said method comprising genetically modifying the host cell with the polynucleotide described herein or the recombinant vector described herein.

In some embodiments, the method further comprises genetically modifying the host cell to express a chimeric antigen receptor (CAR), an antigen specific T cell receptor (TCR) and/or a bispecific antibody.

In some embodiments, the genetic modifying step is conducted via viral gene delivery.

In some embodiments, the genetic modifying step is conducted via non-viral gene delivery.

In some embodiments, the genetically modifying step is conducted ex vivo.

In some embodiments, the method further comprises activation and/or expansion of the host cell ex vivo before, after and/or during said genetic modification.

In various embodiments of the methods described above, the cell is an immune cell. In various embodiments, the cell expresses GM-CSF upon activation.

In some embodiments of the methods described above, the cell is a T cell. In some embodiments, the cell is an αβ TCR T cell, a γδ T cell, or an iNKT cell.

In some embodiments of the methods described above, the cell is a nature killer (NK) cell.

In another aspect, the present disclosure provides a method of treating a disease comprising administering to the subject an effective amount of the host cell described herein, or the pharmaceutical composition described herein.

In some embodiments of the treatment method described above, the host cell is an autologous cell. In some embodiments of the treatment method described above, the host cell is an allogeneic cell.

In some embodiments, the treatment method comprises
a) isolating T cells or NK cells from the subject or donor;
b) modifying said T cells or NK cells ex vivo with the polynucleotide described herein or the recombinant vector described herein;
c) optionally modifying said T cells or NK cells ex vivo to express a chimeric antigen receptor (CAR), an antigen specific T cell receptor (TCR) and/or a bispecific antibody, said CAR, TCR or bispecific antibody specifically binds an antigen associated with said disease;
d) optionally, expanding and/or activating the modified T cells or NK cells before, after and/or during step b) or c); and
e) introducing a therapeutically effective amount of the modified T cells or NK cells into the subject.

In some embodiments of the treatment methods described above, the T cell is an αβ TCR T cell, a γδ T cell, or an iNKT cell.

In some embodiments, the disease is a cancer. In some embodiments, the cancer is a solid tumor.

In some embodiments, one or more cells of the cancer express HER2. In some embodiments, the cancer expressing HER2 is brain, breast, stomach, ovary, uterine serous endometrial carcinoma, colon, bladder, lung, uterine cervix, head and neck, sarcoma, bone tumors, or esophagus cancer.

In some embodiments, one or more cells of the cancer express EphA2. In some embodiments, the cancer expressing EphA2 is breast, prostate, urinary bladder, skin, lung, ovary, sarcoma, bone tumors or brain cancer.

In various embodiments, the subject being treated is human.

BRIEF DESCRIPTION OF THE DRAWINGS

FIG. 1A is a drawing of the exemplary chimeric GM-CSF:IL-18 switch receptor (GM18). The chimeric switch receptor (GM18) can activate MyD88 signaling. FIG. 1B is a schematic of a retroviral vector encoding GM18. ec: extracellular domain, TM: transmembrane domain, ic: intracellular domain. FIGS. 1C-1D show the transduction efficiency measured 4-7 days following transduction by fluorescence-activated cell sorting (FACS) via detection of the GM-CSF receptor (GM-CSFR) α chain (CD116). FIG. 1C is a representative histogram of CD116 expression in non-transduced (NT) cells (gray) and GM18 cells (black line). FIG.

1D is a graph showing the GM18 transduction efficiency from 6 healthy donors. Error bars indicate SEM. ****p<0.0001 according to paired t-test.

Figures 2A, 2B, 2C:
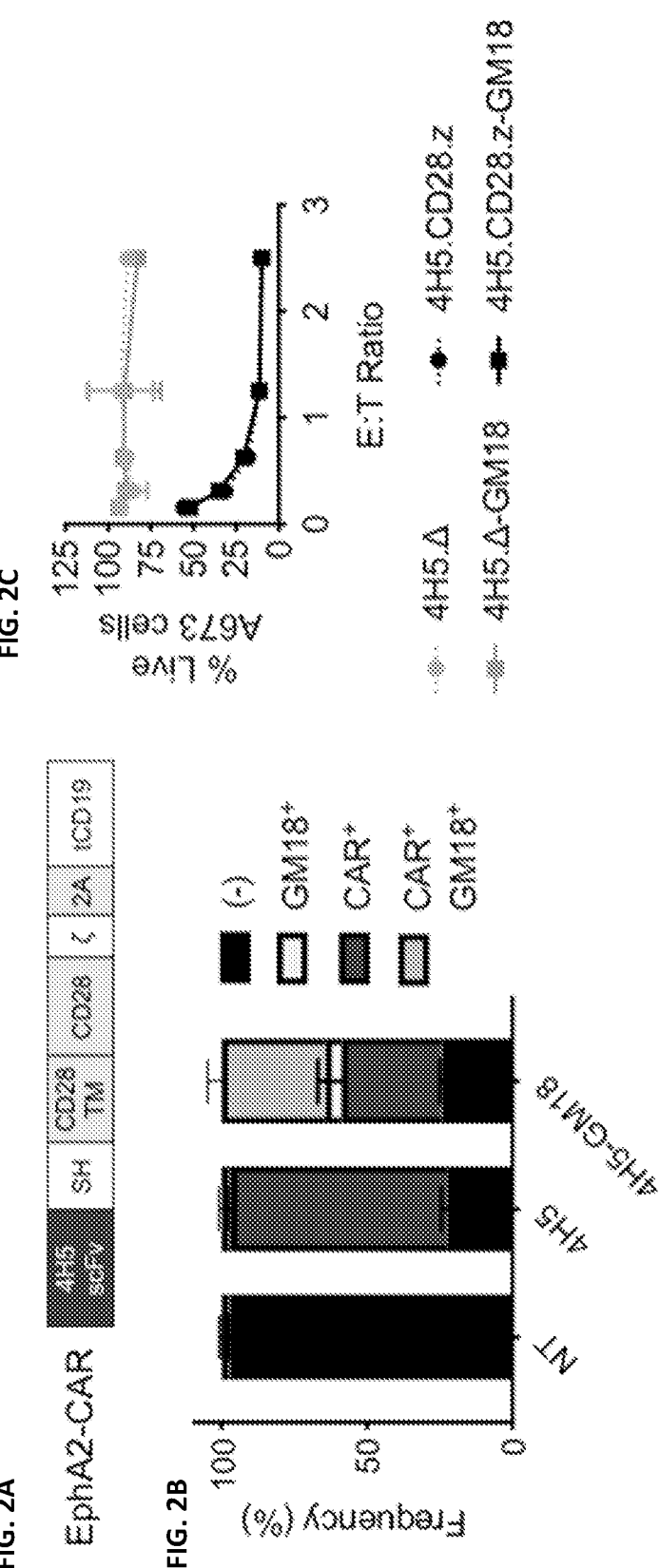
Figure 2K:
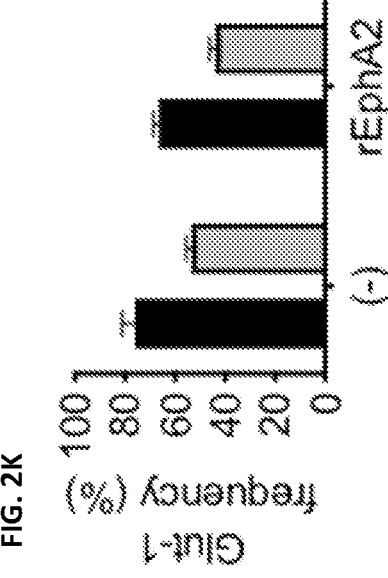
Figure 2J:
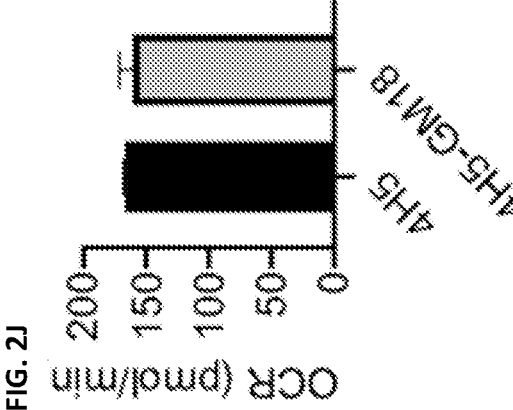
Figure 2I:
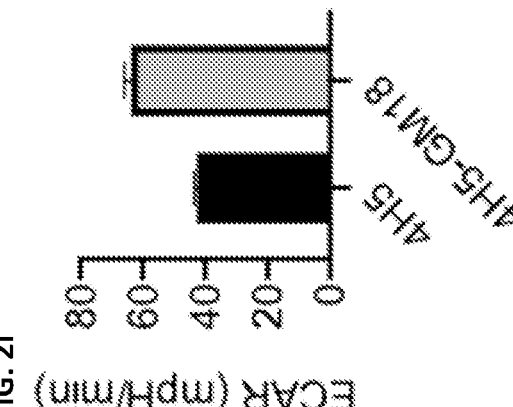

FIGS. 2A-2K demonstrate that GM18-expressing CAR T cells exhibit greater expansion, persistence, and glycolytic activity in vitro. FIG. 2A is a schematic of the retroviral vector encoding the EphA2-CAR (hereinafter referred to as 4H5). FIG. 2B shows the transduction efficiency measured by FACS via detection of the GM-CSFR α chain (CD116) versus CAR detection via CD19. NT: non-transduced. FIG. 2C shows the results from an MTS assay after 24 hour coculture of A673 tumor cells with 4H5 versus 4H5-GM18 (black) CAR T cells, or a non-functional CAR (4H5.Δ, gray). FIG. 2D shows expansion of 4H5 (circle, dotted line) and 4H5-GM18 (squares, solid line) CAR T cells with or without IL-15 after weekly serial coculture with A673 tumors cells at a 2:1 effector to target (E:T) ratio. FIGS. 2E-2H show the results from cytokine Multiplex analysis of supernatant from serial cocultures collected 48 hours after addition of fresh tumor cells. FIGS. 2E-2F show levels of IFN-gamma without (FIG. 2E) or with (FIG. 2F) exogenous IL-15 added. FIGS. 2G-2H show levels of GM-CSF without (FIG. 2G) or with (FIG. 2H) exogenous IL-15 added. FIGS. 2I-2J show extracellular acidification rate (ECAR, FIG. 2I) and maximal respiratory capacity (OCR, FIG. 2J) of 4H5 and 4H5-GM18 CAR T cells from Seahorse flux analysis. FIG. 2K shows the percentage of live 4H5 (black) and 4H5-GM18 (gray) CAR+ cells that express Glut-1. Error bars indicate SEM. In FIG. 2B: n=3, in FIGS. 2C-2K: n=2 healthy donors.

Figures 3A, 3B, 3C, 3D:
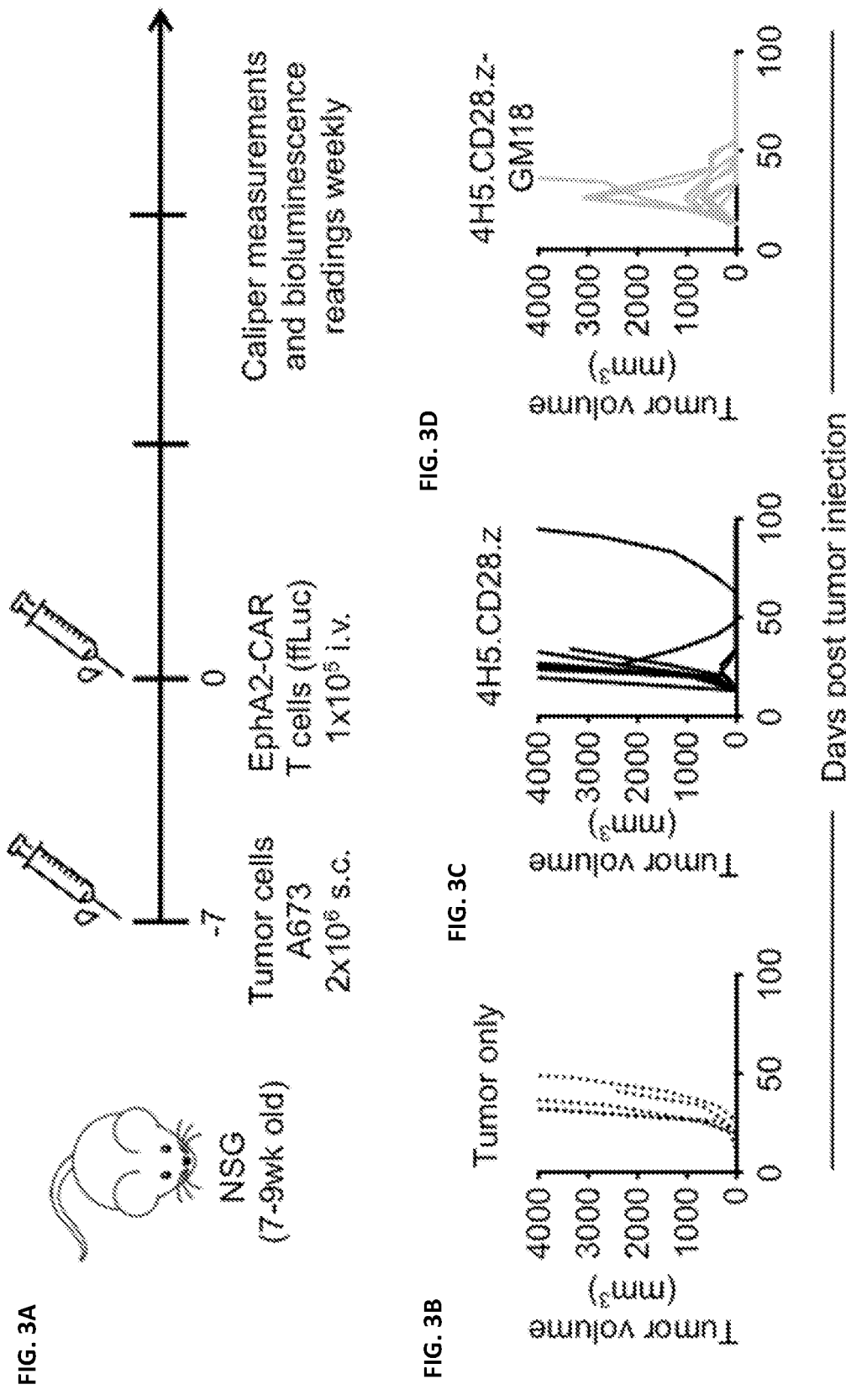
Figures 3E, 3F:
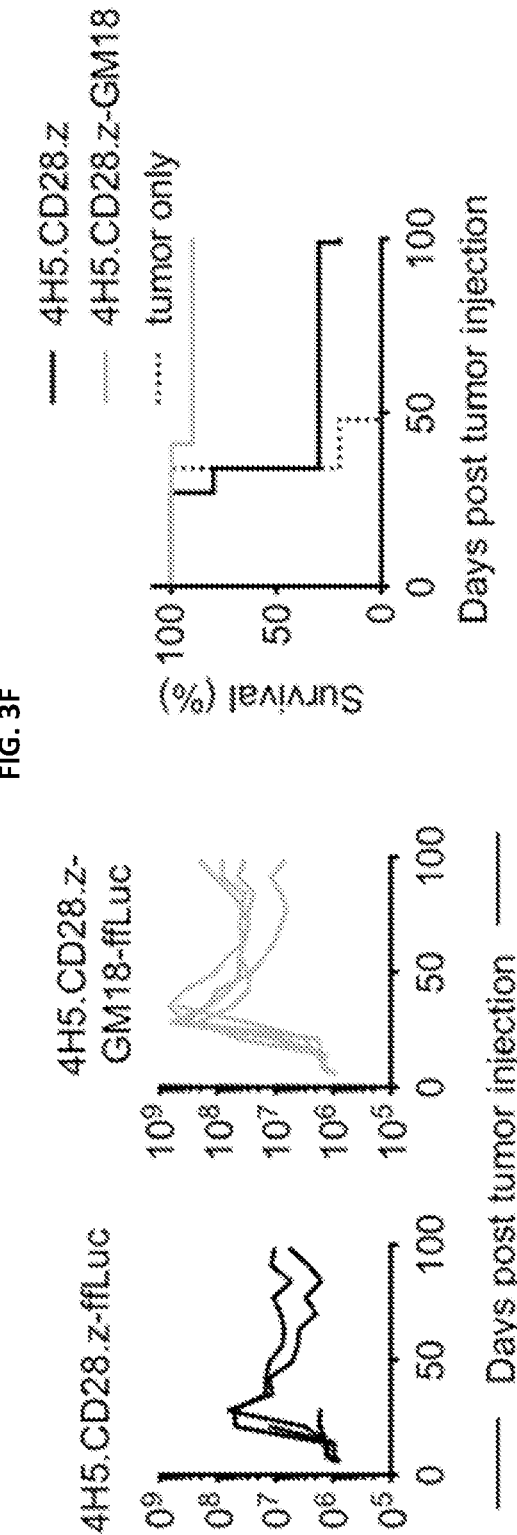

FIGS. 3A-3F demonstrate that GM18-expressing EphA2-CAR T cells display enhanced expansion, persistence, and tumor killing in vivo. FIG. 3A is a schematic of the experimental design of the in vivo study. FIGS. 3B-3D are plots showing tumor growth (tumor volume, mm³) in tumor only group (FIG. 3B, n=5), EphA2-CAR T cell (4H5.CD28.z) treatment group (FIG. 3C, n=10), and EphA2-CAR-GM18 T cell (4H5.CD28.z-GM18) treatment group (FIG. 3D, n=10). FIG. 3E shows results from bioluminescence imaging by IVIS, shown quantitatively (total flux [p/s], n=5 each group). FIG. 3F is a plot showing overall survival of mice (tumor only: n=5, 4H5.CD28.z: n=10, 4H5.CD28.z-GM18: n=10).

Figures 4A, 4B, 4C:
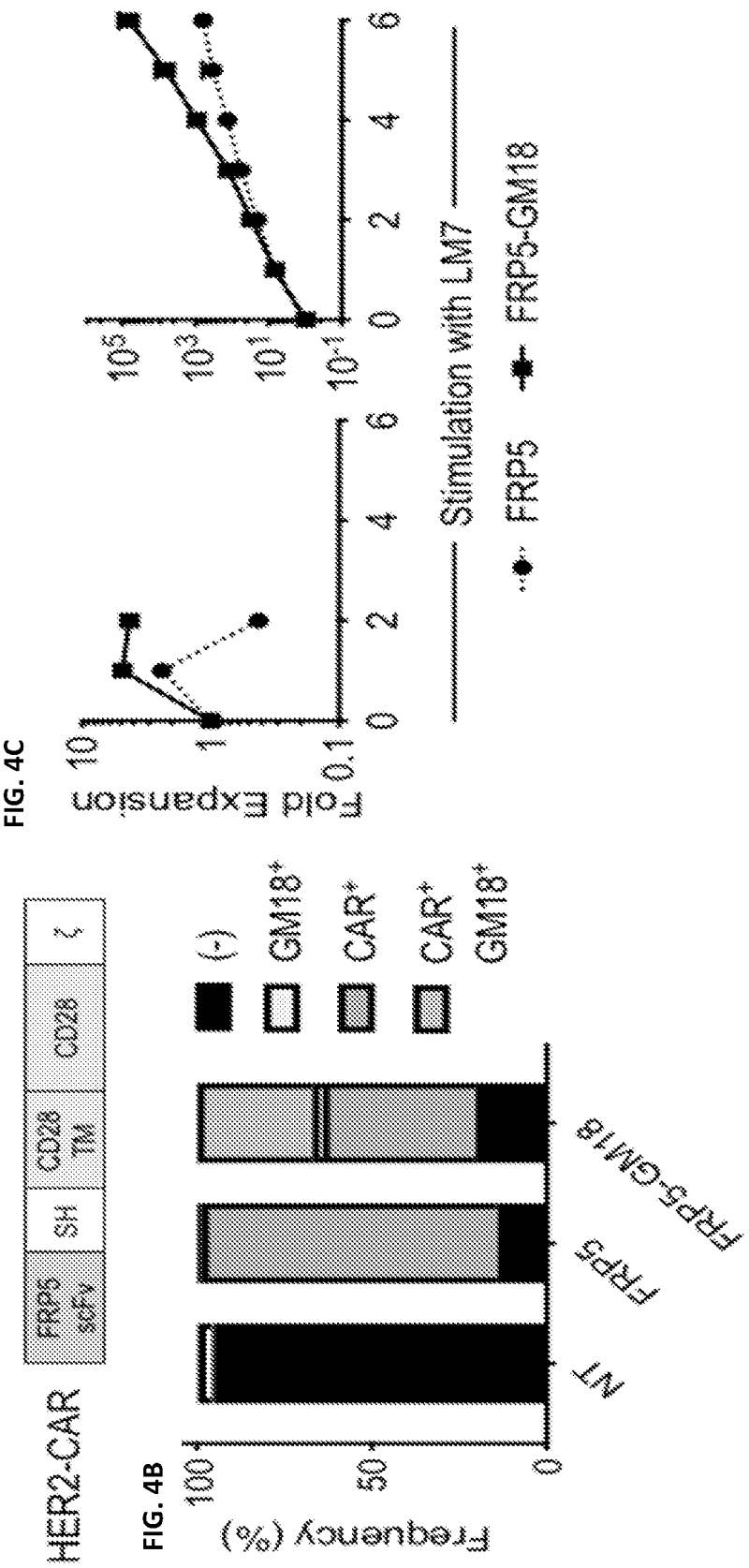
Figures 4D, 4E:
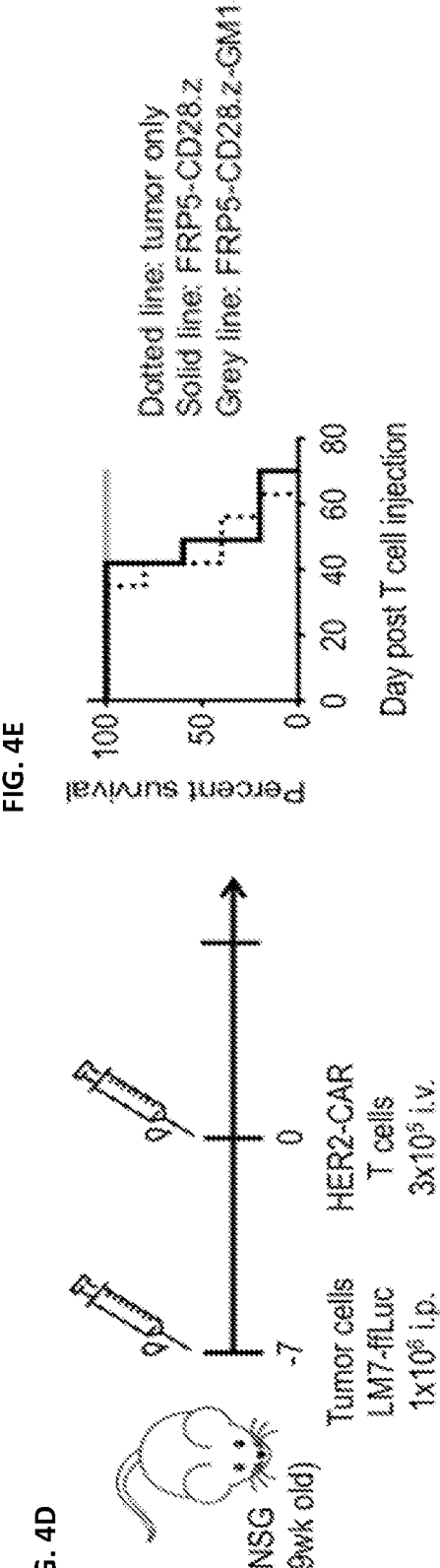
Figures 4F, 4G, 4H:
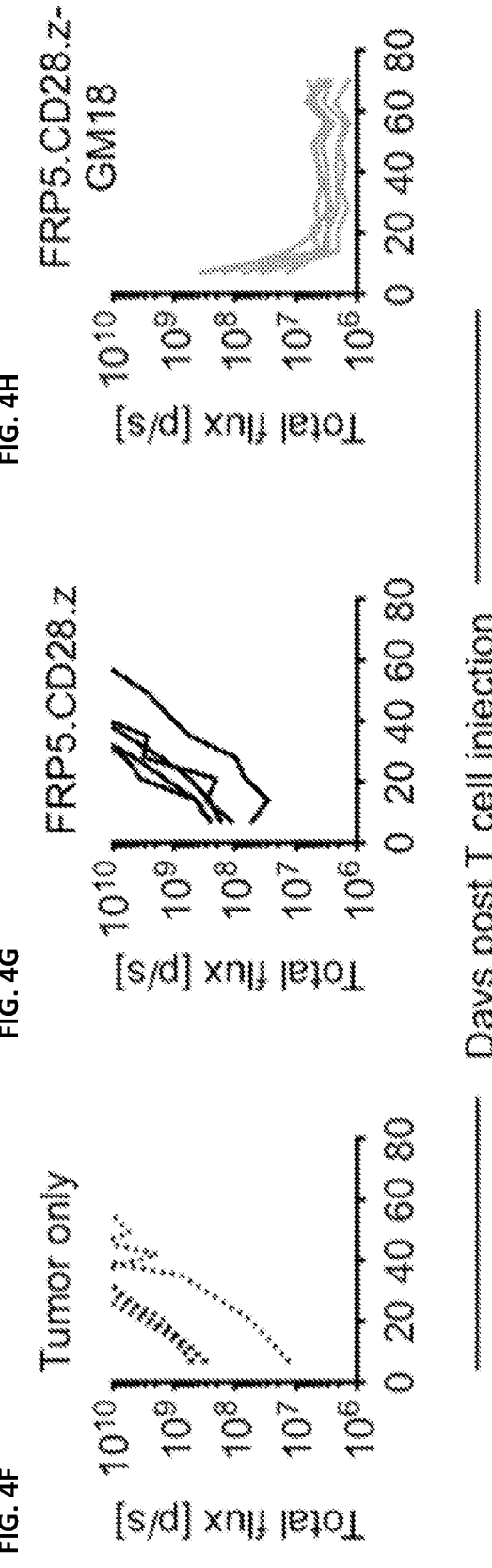

FIGS. 4A-4H demonstrate GM18 expression endows HER2-CAR T cells with enhanced anti-tumor activity. FIG. 4A is a schematic of a retroviral vector encoding the HER2-CAR (hereinafter referred to as FRP5 or FRP5.CD28.z). FIG. 4B shows the transduction efficiency measured by FACS via detection of the GM-CSFR α chain (CD116) versus CAR detection via F(ab')₂ staining. NT: non-transduced. FIG. 4C shows expansion of FRP5 (circle, dotted line) and FRP5-GM (squares, solid line) CAR T cells with or without IL-15 after weekly serial coculture with LM7 tumors cells at a 2:1 E:T ratio. FIG. 4D is a schematic of the experimental design of the in vivo study. FIG. 4E is a plot showing overall survival of mice (n=5 each group). In FIGS. 4F-4H, tumor growth was tracked over time by bioluminescence imaging by IVIS weekly, shown quantitatively (total flux [p/s], n=5 each group).

Figure 5B:
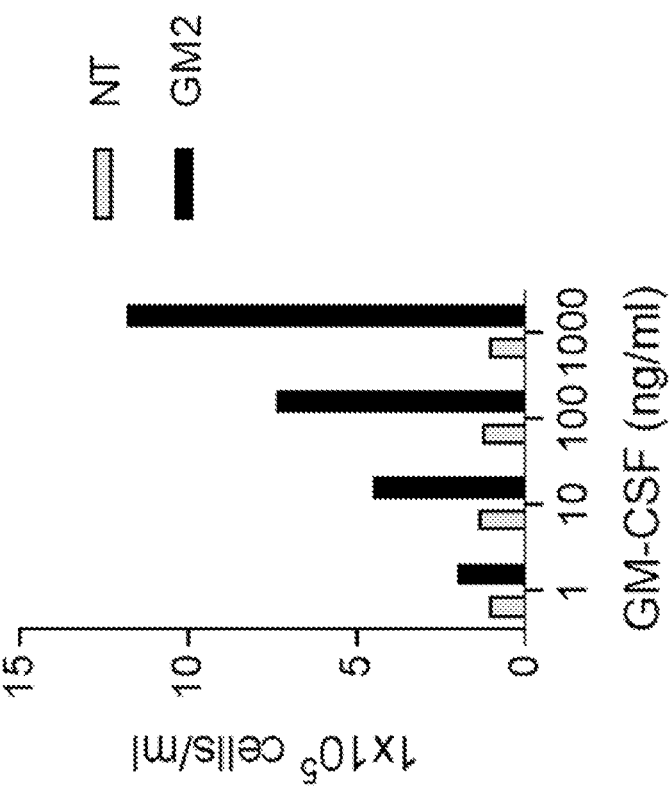
Figure 5A:
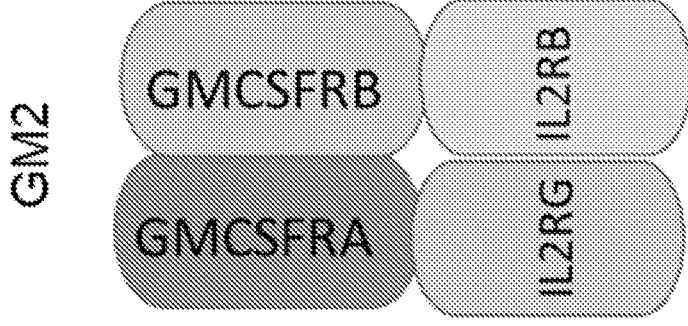
Figures 5C, 5D:
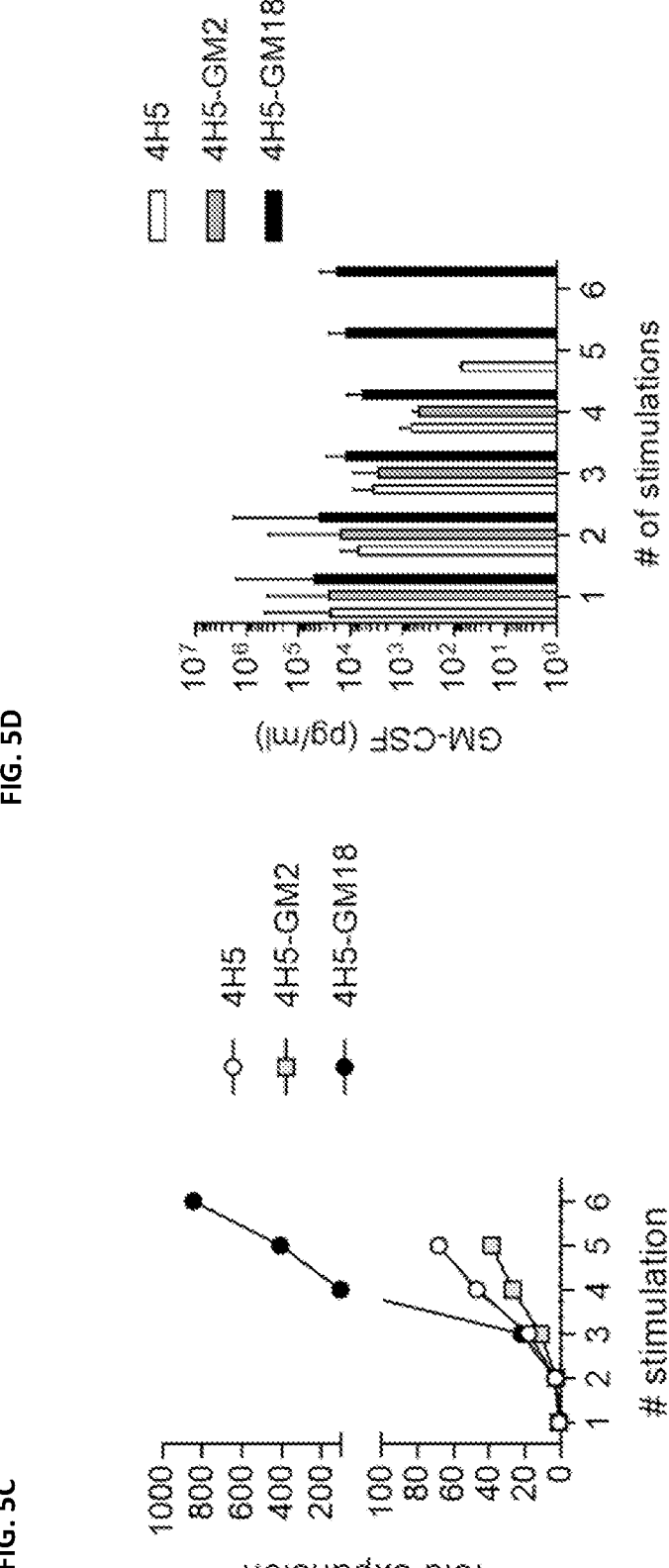

FIGS. 5A-5D compares the benefit of GM18 expression in CAR T cells with expression of a previous published GM-CSF:IL-2 switch receptor (GM2, See Hum Gene Ther. 1999; 10(12):1941-51). FIG. 5A shows the scheme of the GM2 receptor. FIG. 5B demonstrates that the GM2-expressing T cells expand in response to exogenous GM-CSF documenting that GM2 is functional. FIG. 5C compares the expansion of EphA2-CAR (4H5)-GM2, EphA2-CAR (4H5)-GM18, and unmodified EphA2-CAR T cells in a serial coculture assay with EphA2-positive tumor cells. FIG. 5D demonstrates GM-CSF production after each stimulation with tumor cells in the serial coculture assay.

FIGS. 6A-6B show the nucleotide sequence of the GM18 receptor (SEQ ID NO: 24). FIG. 6C shows the amino acid sequence of the GM18 receptor (SEQ ID NO: 23).

Figure 7D:
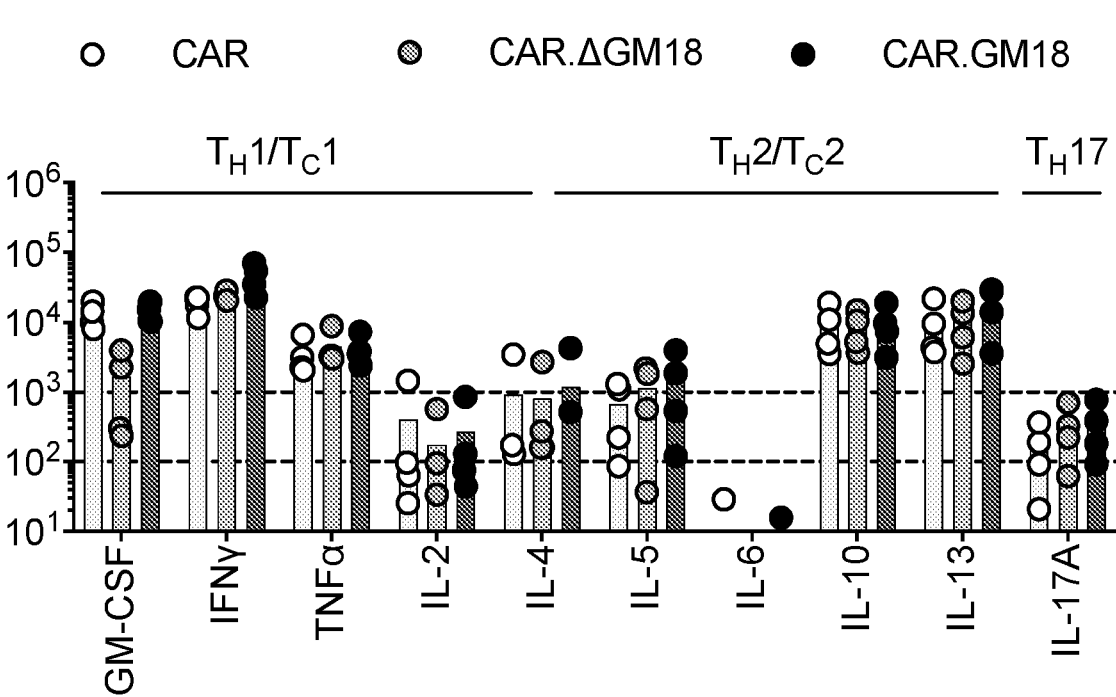
Figure 7E:
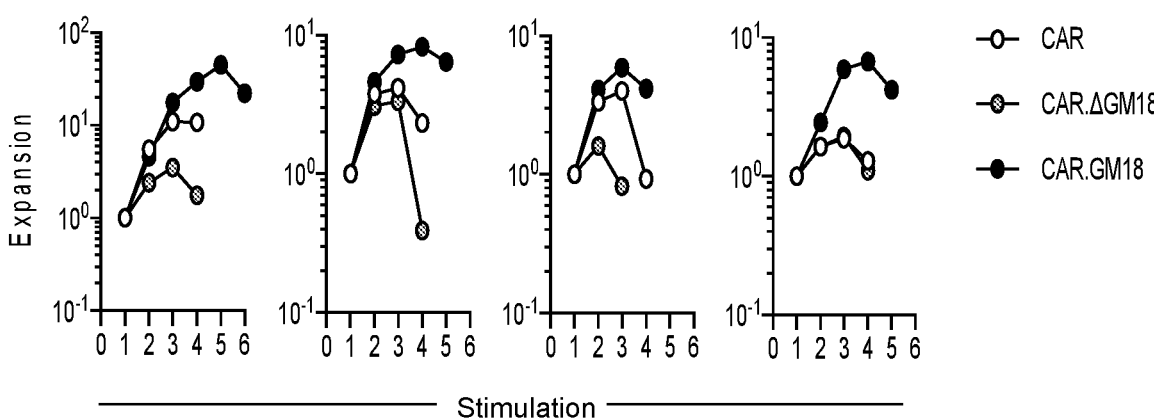

FIGS. 7A-7E demonstrate that truncating the intracellular signaling domains of GM18 abolishes its functional benefits in EphA2-CAR T-cells. FIG. 7A shows a schematic of ΔGM18 construct. GM: GM-CSF receptor; 18: IL-18 receptor; ec: extracellular domain, and TM*: transmembrane domain+10 amino acids of intracellular domain. FIG. 7B shows colorimetric detection of NFκB activity in GM-CSF-treated non-transduced (NT), GM18 transduced (GM18) or GM^stop transduced (ΔGM18) Ramos-Blue reporter cells, 2-way ANOVA, ****p<0.0001, ns: not significant. FIG. 7C shows transduction efficiency of EphA2-CAR, GM18, or AGM18 in human T-cells (N=3 different donors) prior to sorting as measured by flow analysis for the GM-CSFR alpha chain (anti-CD116) and CAR (anti-CD19). FIG. 7D shows cytokine production by sorted CAR T-cells after one stimulation with A673 tumor cells at 2:1 E:T ratio measured by multiplex analysis, N=4 different donors. FIG. 7E shows sorted CAR T-cell expansion following serial coculture with fresh A673 tumor cells weekly. Fold expansion of CAR, CAR.ΔGM18, and CAR.GM18 T-cells, N=4 different donors graphed individually.

Figure 8A:
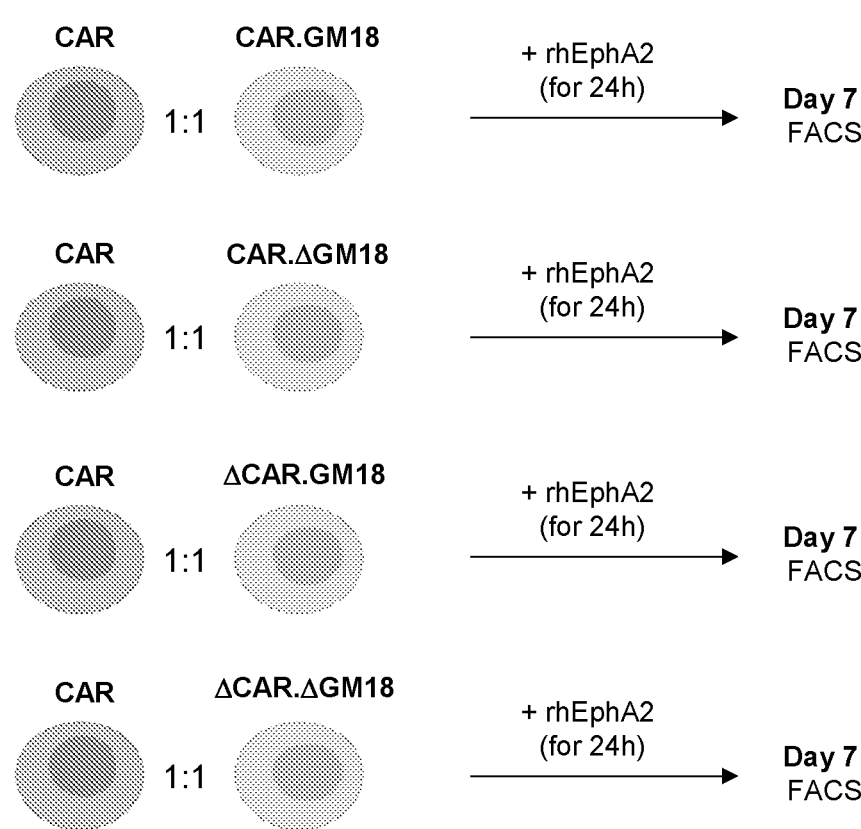
Figure 8B:
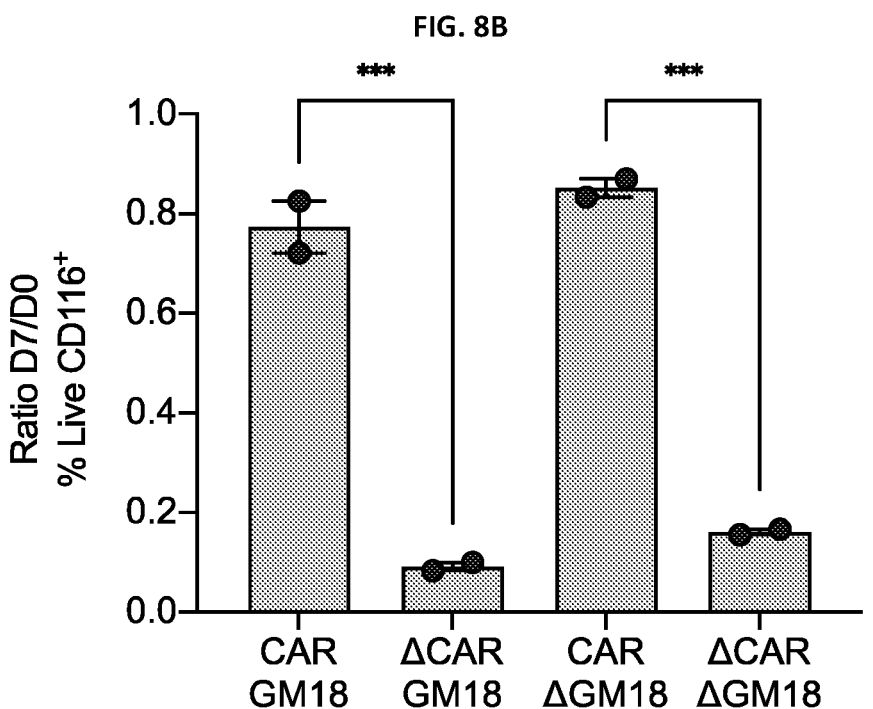

FIGS. 8A-8B demonstrate that expansion of CAR.GM18 T-cells is not induced by activated bystander CAR T cells. FIG. 8A illustrates the experimental setup: Sorted EphA2-CAR T-cells were combined with either CAR.GM18, CAR.ΔGM18, delta (Δ)-CAR.GM18, or ΔCAR.ΔGM18 at a 1:1 ratio and stimulated with recombinant hEphA2 protein (200 ng per 1×10⁶ cells) for 24 hours without exogenous cytokines and cultured for 7 days. FIG. 8B shows the ratio of CAR+CD116+ cells acquired at day 0 and day 7. N=2 different donors, mean and +/−SEM is shown, 2-way ANOVA, ***p<0.001.

Figures 9A, 9B:
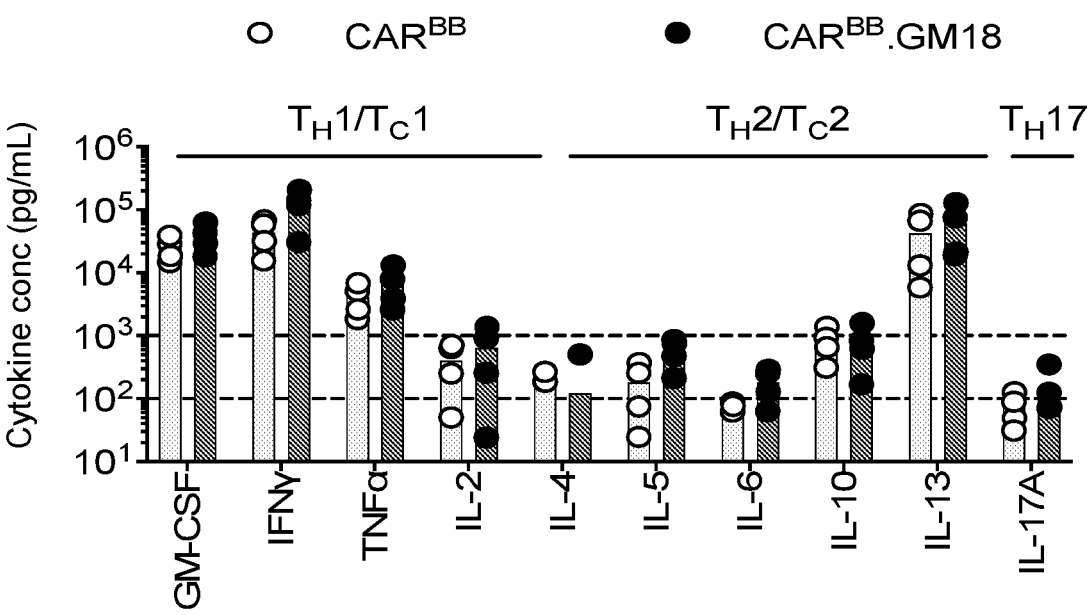
Figure 9C:
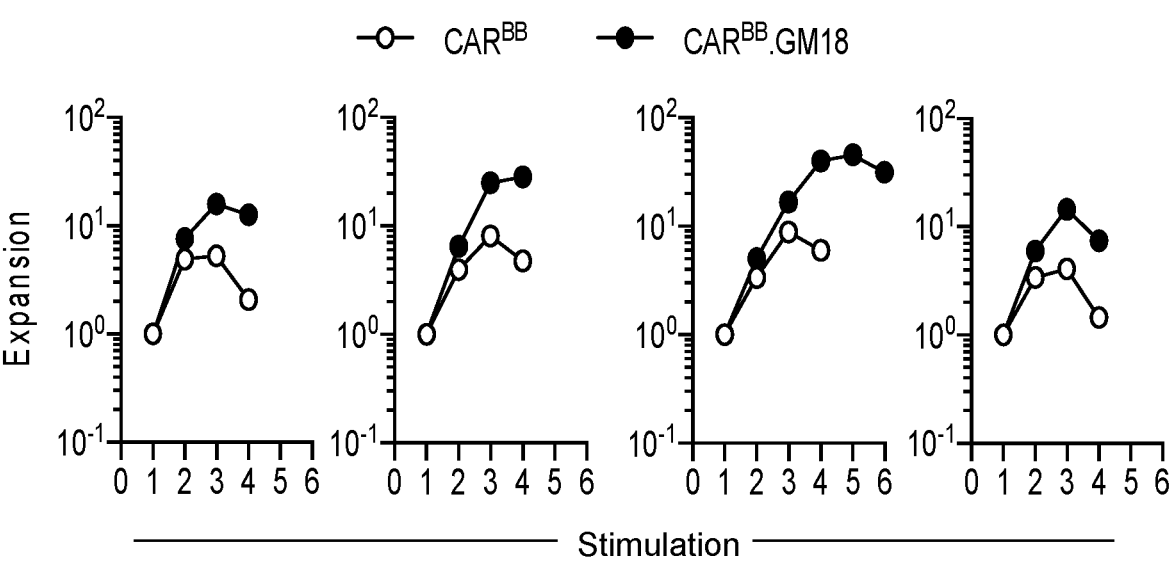
Figure 9D:
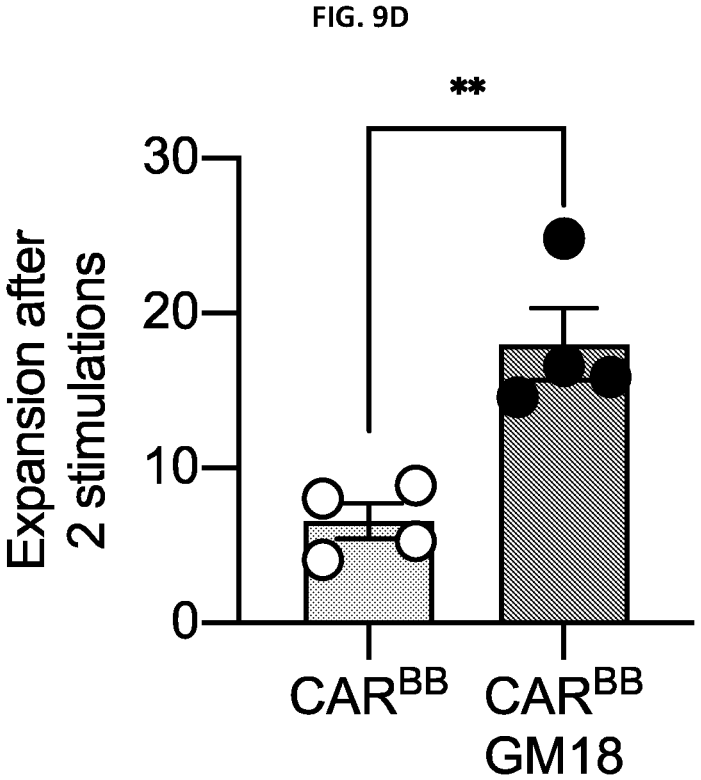

FIGS. 9A-9D demonstrate that GM18 improves effector function in vitro of EphA2-CAR T-cells with 4-1BB costimulatory domain. FIG. 9A shows transduction efficiency of 4-1BB EphA2-CAR (CAR^BB) and GM18 in human T-cells (N=4 different donors) prior to sorting as measured by flow analysis for the GM-CSFR alpha chain (anti-CD116) and CAR (anti-CD19). FIG. 9B shows cytokine production by sorted CAR T-cells after one stimulation with A673 tumor cells at 2:1 E:T ratio measured by multiplex analysis, N=4 different donors. FIG. 9C shows sorted CAR T-cell expansion following serial coculture with fresh A673 tumor cells weekly. Fold expansion of CAR^BB and CAR^BB.GM18 T-cells; N=4 different donors graphed individually. FIG. 9D shows summary data of expansion of CAR^BB and CAR^BB.GM18 T-cells after 2 stimulations, **p<0.01, paired T-test.

FIGS. 10A-10C demonstrate that GM18 T-cells do not display alloreactivity independent of EphA2-CAR activation in vivo. FIG. 10A shows the experimental setup: NSG mice were injected with 2×10⁶ A673 cells s.c. followed by i.v. injection of 3×10⁵ CAR T-cells on day 7. Tumors were measured weekly by calipers. FIG. 10B shows the tumor volume of untreated (N=6), non-transduced (NT) (N=5), GM18 (N=5), ΔCAR (N=4), ΔCAR.GM18 (N=5), and EphA2-CAR.GM18 (N=5) T-cell treated mice. FIG. 10C shows a Kaplan-Meier survival curve; **p<0.01; Log-rank (Mantel-Cox) test.

DETAILED DESCRIPTION

This invention is based on a surprising and unexpected discovery that a self-sustaining cytokine receptor could improve the efficacy of therapeutic immune cells (e.g., CAR T cells) in the tumor microenvironment (TME).

One cytokine that is produced by immune cells upon stimulation and is present in the TME is the myeloid cytokine granulocyte-macrophage colony-stimulating factor (GM-CSF). Based on this biology, an exemplary chimeric cytokine switch receptor was designed that can bind GM-CSF, but signal intracellularly through IL-18 receptor endodomains. This exemplary switch receptor is herein referred to as GM18. As demonstrated in the Examples section below, this switch receptor encoded by a retroviral vector was transduced into CAR T cells targeting different solid tumor antigens. In vitro, GM18-expressing CAR T cells (CAR-GM18 T cells) initially killed tumor cells to the same degree as unmodified CAR T cells, but displayed greater expansion when repeatedly challenged with tumor cells over time. In vivo, CAR-GM18 T cells exhibited enhanced antitumor activity compared to unmodified CAR T cells in NSG models of osteosarcoma (LM7) and Ewing sarcoma (A673), leading to improved survival. This coincided with greater expansion and persistence of CAR-GM18 T cells. The results demonstrate the GM18 cytokine switch receptor as an advantageous modification of CAR T cells for the immunotherapy of solid tumors.

In fact, most immune cells (for example but not limited to, αβ TCR T cells, γδ T cells, iNKT cells, NK cells) express GM-CSF upon activation. Accordingly, this invention has broad applicability in immunotherapy.

In addition to GM-CSF being produced by immune cells, GM-CSF could also be provided separately to enhance the function of GM18-expressing immune cells. Examples include, but not limited to, the i) injection of the FDA-approved GM-CSF drug Sargramostin (Leukine™) or ii) the use of nonviral or viral vectors to express GM-CSF (e.g. FDA-approved GM-CSF expressing oncolytic virus talimogene laherparepvec [TVEC, Imlygic™]) to enhance the function of GM18-expressing immune cells. These drugs could be given before, with, or after the infusion of GM18-expressing immune cells to patients.

Definitions

The term "chimeric cytokine receptor" as used herein refers to an engineered receptor comprising a cytokine binding portion from one receptor linked to an intracellular signaling portion from a different receptor.

The terms "T cell" and "T lymphocyte" are interchangeable and used synonymously herein. As used herein, T-cell includes thymocytes, naive T lymphocytes, immature T lymphocytes, mature T lymphocytes, resting T lymphocytes, or activated T lymphocytes. A T-cell can be a T helper (Th) cell, for example a T helper 1 (Th1) or a T helper 2 (Th2) cell. The T-cell can be a helper T-cell (HTL; CD4+ T-cell) CD4+ T-cell, a cytotoxic T-cell (CTL; CD8+ T-cell), a tumor infiltrating cytotoxic T-cell (TIL; CD8+ T-cell), CD4+CD8+ T-cell, or any other subset of T-cells. Other illustrative populations of T-cells suitable for use in particular embodiments include naive T-cells and memory T-cells. Also included are "NKT cells", which refer to a specialized population of T-cells that express a semi-invariant αβ T-cell receptor, but also express a variety of molecular markers that are typically associated with NK cells, such as NK1.1. NKT cells include NK1.1+ and NK1.1−, as well as CD4+, CD4−, CD8+ and CD8− cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T-cells (γδ T-cells)," which refer to a specialized population that to a small subset of T-cells possessing a distinct TCR on their surface, and unlike the majority of T-cells in which the TCR is composed of two glycoprotein chains designated α- and β-TCR chains, the TCR in γδ T-cells is made up of a γ-chain and a δ-chain. γδ T-cells can play a role in immunosurveillance and immunoregulation, and were found to be an important source of IL-17 and to induce robust CD8+ cytotoxic T-cell response. Also included are "regulatory T-cells" or "Tregs" refers to T-cells that suppress an abnormal or excessive immune response and play a role in immune tolerance. Tregs cells are typically transcription factor Foxp3-positive CD4+ T cells and can also include transcription factor Foxp3-negative regulatory T-cells that are IL-10-producing CD4+ T cells.

The terms "natural killer cell" and "NK cell" are used interchangeable and used synonymously herein. As used herein, NK cell refers to a differentiated lymphocyte with a CD 16+ CD56+ and/or CD57+ TCR-phenotype. NKs are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

As used herein, the term "antigen" refers to any agent (e.g., protein, peptide, polysaccharide, glycoprotein, glycolipid, nucleic acid, portions thereof, or combinations thereof) molecule capable of being bound by a T-cell receptor. An antigen is also able to provoke an immune response. An example of an immune response may involve, without limitation, antibody production, or the activation of specific immunologically competent cells, or both. A skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components, organisms, subunits of proteins/ antigens, killed or inactivated whole cells or lysates.

The term "chimeric antigen receptor" or "CAR" as used herein is defined as a cell-surface receptor comprising an extracellular target-binding domain, a transmembrane domain, and a cytoplasmic domain comprising a lymphocyte activation domain and optionally at least one co-stimulatory signaling domain, all in a combination that is not naturally found together on a single protein. This particularly includes receptors wherein the extracellular domain and the cytoplasmic domain are not naturally found together on a single receptor protein. The chimeric antigen receptors described herein are intended for use with, for example, lymphocytes such as T-cells and natural killer (NK) cells.

The term "antigen-binding domain" refers to a target-specific binding element that may be any ligand that binds to the antigen of interest or a polypeptide or fragment thereof, wherein the ligand is either naturally derived or synthetic. Examples of antigen-binding domains include, but are not limited to, antibodies; polypeptides derived from antibodies, such as, for example, single chain variable fragments (scFv), Fab, Fab', F(ab')₂, and Fv fragments; polypeptides derived from T-cell receptors, such as, for example, TCR variable domains; secreted factors (e.g., cytokines, growth factors) that can be artificially fused to signaling domains (e.g., "zytokines"); and any ligand or receptor fragment (e.g., CD27, NKG2D) that binds to the antigen of interest. Combinatorial libraries could also be used to identify peptides binding with high affinity to the therapeutic target.

Terms "antibody" and "antibodies" refer to monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), intrabodies, minibodies, diabodies and anti-idiotypic (anti-Id) antibodies (including, e.g., anti-Id antibodies to antigen-specific TCR), and epitope-binding fragments of any of the above. The terms "antibody" and "antibodies" also refer to covalent diabodies such as those disclosed in U.S. Pat. Appl. Pub. 2007/0004909 and Ig-DARTS such as those disclosed in U.S. Pat. Appl. Pub. 2009/0060910. Antibodies useful as a TCR-binding molecule include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgM1, IgM2, IgA1 and IgA2) or subclass.

The term "host cell" means any cell that contains a heterologous nucleic acid. The heterologous nucleic acid can be a vector (e.g., an expression vector). For example, a host cell can be a cell from any organism that is selected, modified, transformed, grown, used or manipulated in any way, for the production of a substance by the cell, for example the expression by the cell of a gene, a DNA or RNA sequence, a protein or an enzyme. An appropriate host may be determined. For example, the host cell may be selected based on the vector backbone and the desired result. By way of example, a plasmid or cosmid can be introduced into a prokaryote host cell for replication of several types of vectors. Bacterial cells such as, but not limited to DH5α, JM109, and KCB, SURE® Competent Cells, and SOLO-PACK Gold Cells, can be used as host cells for vector replication and/or expression. Additionally, bacterial cells such as *E. coli* LE392 could be used as host cells for phage viruses. Eukaryotic cells that can be used as host cells include, but are not limited to yeast (e.g., YPH499, YPH500 and YPH501), insects and mammals. Examples of mammalian eukaryotic host cells for replication and/or expression of a vector include, but are not limited to, HeLa, NIH3T3, Jurkat, 293, COS, CHO, Saos, and PC12. In certain embodiments, the host cell is autologous. In certain embodiments, the host cell is allogenic.

Host cells of the present disclosure include immune cells (e.g., T-cells and natural killer cells) that contain the DNA or RNA sequences encoding the chimeric cytokine receptor and express the chimeric cytokine receptor on the cell surface. Host cells may be used for enhancing immune cell activity (e.g., effector function), treatment of tumors, and treatment of autoimmune disease.

The terms "activation" or "stimulation" means to induce a change in their biologic state by which the cells (e.g., T-cells and NK cells) express activation markers, produce cytokines, proliferate and/or become cytotoxic to target cells. All these changes can be produced by primary stimulatory signals. Co-stimulatory signals can amplify the magnitude of the primary signals and suppress cell death following initial stimulation resulting in a more durable activation state and thus a higher cytotoxic capacity. A "co-stimulatory signal" refers to a signal, which in combination with a primary signal, such as TCR/CD3 ligation, leads to T-cell and/or NK cell proliferation and/or upregulation or downregulation of key molecules.

The term "proliferation" refers to an increase in cell division, either symmetric or asymmetric division of cells.

The term "differentiation" refers to a method of decreasing the potency or proliferation of a cell or moving the cell to a more developmentally restricted state.

The terms "express" and "expression" mean allowing or causing the information in a gene or DNA sequence to become produced, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or transmembrane.

The term "transfection" means the introduction of a "foreign" (i.e., extrinsic or extracellular) nucleic acid into a cell using recombinant DNA technology. The term "genetic modification" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences operably linked to polynucleotide encoding the chimeric cytokine receptor, such as start, stop, promoter, signal, secretion, or other sequences used by a cell's genetic machinery. The gene or sequence may include nonfunctional sequences or sequences with no known function. A host cell that receives and expresses introduced DNA or RNA has been "genetically engineered." The DNA or RNA introduced to a host cell can come from any source, including cells of the same genus or species as the host cell, or from a different genus or species.

The term "transduction" means the introduction of a foreign nucleic acid into a cell using a viral vector.

The terms "genetically modified" or "genetically engineered" refers to the addition of extra genetic material in the form of DNA or RNA into a cell.

As used herein, the term "derivative" or "variant" in the context of proteins or polypeptides (e.g., chimeric cytokine receptor constructs or domains thereof) refer to: (a) a polypeptide that has at least 40%, 45%, 50%, 55%, 60%, 65%, 70%, 75%, 80%, 85%, 90%, 95%, 98% or 99% sequence identity to the polypeptide it is a derivative or variant of; (b) a polypeptide encoded by a nucleotide sequence that has at least 40%, 45%, 50%, 55%, 60%, 65%, 70%, 75%, 80%, 85%, 90%, 95%, 98% or 99% sequence identity to a nucleotide sequence encoding the polypeptide it is a derivative or variant of; (c) a polypeptide that contains 1, 2, 3, 4, 5, 6, 7, 8, 9, 10, 11, 12, 13, 14, 15, 16, 17, 18, 19, 20 or more amino acid mutations (i.e., additions, deletions and/or substitutions) relative to the polypeptide it is a derivative or variant of; (d) a polypeptide encoded by nucleic acids can hybridize under high, moderate or typical stringency hybridization conditions to nucleic acids encoding the polypeptide it is a derivative or variant of; (e) a polypeptide encoded by a nucleotide sequence that can hybridize under high, moderate or typical stringency hybridization conditions to a nucleotide sequence encoding a fragment of the polypeptide, it is a derivative or variant of, of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids; or (f) a fragment of the polypeptide it is a derivative or variant of.

Percent sequence identity can be determined using any method known to one of skill in the art. In a specific embodiment, the percent identity is determined using the "Best Fit" or "Gap" program of the Sequence Analysis Software Package (Version 10; Genetics Computer Group, Inc., University of Wisconsin Biotechnology Center, Madison, Wisconsin). Information regarding hybridization conditions (e.g., high, moderate, and typical stringency conditions) have been described, see, e.g., U.S. Patent Application Publication No. US 2005/0048549 (e.g., paragraphs 72-73).

The terms "vector", "cloning vector" and "expression vector" mean the vehicle by which a DNA or RNA sequence (e.g., a foreign gene) can be introduced into a host cell, so as to genetically modify the host and promote expression (e.g., transcription and translation) of the introduced sequence. Vectors include plasmids, synthesized RNA and DNA molecules, phages, viruses, etc. In certain embodiments, the vector is a viral vector such as, but not limited to, viral vector is an adenoviral, adeno-associated, alphaviral, herpes, lentiviral, retroviral, or vaccinia vector.

The term "regulatory element" refers to any cis-acting genetic element that controls some aspect of the expression of nucleic acid sequences. In some embodiments, the term "promoter" comprises essentially the minimal sequences required to initiate transcription. In some embodiments, the term "promoter" includes the sequences to start transcription, and in addition, also include sequences that can upregulate or downregulate transcription, commonly termed "enhancer elements" and "repressor elements", respectively.

As used herein, the term "operatively linked," and similar phrases, when used in reference to nucleic acids or amino acids, refer to the operational linkage of nucleic acid sequences or amino acid sequence, respectively, placed in functional relationships with each other. For example, an operatively linked promoter, enhancer elements, open reading frame, 5' and 3' UTR, and terminator sequences result in the accurate production of a nucleic acid molecule (e.g., RNA). In some embodiments, operatively linked nucleic acid elements result in the transcription of an open reading frame and ultimately the production of a polypeptide (i.e., expression of the open reading frame). As another example, an operatively linked peptide is one in which the functional domains are placed with appropriate distance from each other to impart the intended function of each domain.

By "enhance" or "promote," or "increase" or "expand" or "improve" refers generally to the ability of a composition contemplated herein to produce, elicit, or cause a greater physiological response (i.e., downstream effects) compared to the response caused by either vehicle or a control molecule/composition. A measurable physiological response may include an increase in immune cell expansion, activation, effector function, persistence, and/or an increase in tumor cell death killing ability, among others apparent from the understanding in the art and the description herein. In certain embodiments, an "increased" or "enhanced" amount can be a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. In certain embodiments, a "decrease" or "reduced" amount can be a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The term "protein" is used herein encompasses all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

The terms "nucleic acid", "nucleotide", and "polynucleotide" encompass both DNA and RNA unless specified otherwise. By a "nucleic acid sequence" or "nucleotide sequence" is meant the nucleic acid sequence encoding an amino acid, the term may also refer to the nucleic acid sequence including the portion coding for any amino acids added as an artifact of cloning, including any amino acids coded for by linkers.

The terms "patient", "individual", "subject", and "animal" are used interchangeably herein and refer to mammals,

15

16

Chimeric Cytokine Receptors including, without limitation, human and veterinary animals (e.g., cats, dogs, cows, horses, sheep, pigs, etc.) and experimental animal models. In a preferred embodiment, the subject is a human.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

Singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

If aspects of the disclosure are described as "comprising" a feature, or versions there of (e.g., comprise), embodiments also are contemplated "consisting of" or "consisting essentially of" the feature.

The practice of the present disclosure employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al. eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Protocols in Microbiology, John Wiley and Sons, Inc.: Hoboken, NJ; Coligan et al. eds. (2005) Current Protocols in Protein Science, John Wiley and Sons, Inc.: Hoboken, NJ; and Enna et al. eds. (2005) Current Protocols in Pharmacology, John Wiley and Sons, Inc.: Hoboken, NJ Additional techniques are explained, e.g., in U.S. Pat. No. 7,912,698 and U.S. Patent Appl. Pub. Nos. 2011/0202322 and 2011/0307437.

The technology illustratively described herein suitably may be practiced in the absence of any element(s) not specifically disclosed herein.

The terms and expressions which have been employed are used as terms of description and not of limitation, and use of such terms and expressions do not exclude any equivalents of the features shown and described or portions thereof, and various modifications are possible within the scope of the technology claimed.

In certain aspects, the present disclosure provides chimeric cytokine receptors that can be activated in a tumor microenvironment.

In one aspect provided herein is a polynucleotide encoding a chimeric cytokine receptor, said chimeric cytokine receptor comprising an extracellular domain of granulocyte-macrophage colony-stimulating factor (GM-CSF) receptor, or a functional portion thereof, a transmembrane domain, and an intracellular domain of interleukin-18 receptor (IL-18) receptor, or a functional portion thereof.

In another aspect provided herein is a chimeric cytokine receptor encoded by the polynucleotide described herein. The chimeric cytokine receptor comprises an extracellular domain of granulocyte-macrophage colony-stimulating factor (GM-CSF) receptor, or a functional portion thereof, a transmembrane domain, and an intracellular domain of interleukin-18 receptor (IL-18) receptor, or a functional portion thereof.

In one embodiment, the chimeric cytokine receptor comprises i. a first polypeptide comprising an extracellular region of GM-CSF receptor α chain, or a functional portion thereof, a first transmembrane region, and an intracellular region of IL-18 receptor α chain, or a functional portion thereof; and ii. a second polypeptide comprising an extracellular region of GM-CSF receptor β chain, or a functional portion thereof, a second transmembrane region, and an intracellular region of IL-18 receptor β chain, or a functional portion thereof.

In another embodiment, the chimeric cytokine receptor comprises i. a first polypeptide comprising an extracellular region of GM-CSF receptor α chain, or a functional portion thereof, a first transmembrane region, and an intracellular region of IL-18 receptor β chain, or a functional portion thereof; and ii. a second polypeptide comprising an extracellular region of GM-CSF receptor β chain, or a functional portion thereof, a second transmembrane region, and an intracellular region of IL-18 receptor α chain, or a functional portion thereof.

In some embodiments, the GM-CSF receptor α chain described herein is human GM-CSF receptor subunit α (UniProtKB identifier P15509), or a homolog or variant thereof.

In some embodiments, the GM-CSF receptor β chain described herein is human cytokine receptor common subunit β isoform 2 (UniProtKB identifier P32927-2), or a homolog or variant thereof.

In some embodiments, the IL-18 receptor α chain described herein is human interleukin-18 receptor 1 (UniProtKB identifier Q13478), or a homolog or variant thereof.

In some embodiments, the IL-18 receptor β chain described herein is human IL-18 receptor accessory protein (UniProtKB identifier O95256), or a homolog or variant thereof.

In various embodiments, the chimeric cytokine receptor comprises an intracellular domain that is not an intracellular domain of interleukin-2 receptor (IL-2) receptor.

In some embodiments, the chimeric cytokine receptor comprises a functional portion of the extracellular domain of the GM-CSF receptor. A functional portion of extracellular domain of the GM-CSF receptor may comprise one or more of the following regions and/or residues: 1) domains 1 and 2 of GM-CSF receptor α chain, particularly loop residues 241 to 251 (RTYQKLSYLDF (SEQ ID NO: 52)) and 299 to 305 (ADVRILN (SEQ ID NO: 53)); 2) E-F loop (residues 100 to 107) (CQSFVVTD (SEQ ID NO: 54)) of GM-CSF receptor β chain domain 1 and the B-C (residues 360 to 369) (TMKMRYEHID (SEQ ID NO: 55)) and F-G (residues 417 to 423) (SRTGYNG (SEQ ID NO: 56)) loops of GM-CSF receptor β chain domain 4; 3) residues 231 (T), 232 (T), 259 (R), 266-270 (TENLL (SEQ ID NO: 57)), and 280-286 (RYNFPSS (SEQ ID NO: 58)) of GM-CSF receptor α chain and residues 350 (D), 353 (S), 366-369 (EHID (SEQ ID NO: 59)), 389-400 (ETLQNAHSMALP (SEQ ID NO: 60)), and 418 (R) of GM-CSF receptor β chain; and 4) residues 344-365 (SLNVTKDGDSYSLRWET (SEQ ID NO: 61)) and 427-438 (EWSEARSWDTES (SEQ ID NO: 62)) of GM-CSF receptor β chain. See e.g., Hansen et al., (2008) *Cell*. August 8; 134(3):496-507 and Hercus et al., (2009) *Blood*. August 13; 114(7):1289-98, both incorporated by reference in their entirety for all purposes. In some embodiments, a functional portion of the extracellular region of GM-CSF receptor α chain comprises one or more of the following regions and/or residues: domains 1 and/or 2 (e.g., loop residues 241 to 251 (RTYQKLSYLDF (SEQ ID NO: 52)) and 299 to 305 (ADVRILN (SEQ ID NO: 53)) of GM-CSF receptor α chain, residues 231 (T), 232 (T), 259 (R), 266-270 (TENLL (SEQ ID NO: 57)), and/or 280-286 (RYNFPSS (SEQ ID NO: 58)) of the GM-CSF receptor α chain. In some embodiments, a functional portion of the extracellular region of GM-CSF receptor β chain comprises one or more of the following regions and/or residues: E-F loop (residues 100 to 107) (CQSFVVTD (SEQ ID NO: 54)) of GM-CSF receptor β chain domain 1, B-C (residues 360 to 369) (TMKMRYEHID (SEQ ID NO: 55)) and/or F-G (residues 417 to 423) (SRTGYNG (SEQ ID NO: 56)) loops of GM-CSF receptor β chain domain 4, residues 350 (D), 353 (S), 366-369 (EHID (SEQ ID NO: 59)), 389-400 (ETLQNAHSMALP (SEQ ID NO: 60)), and 418 (R), and/or residues 344-365 (SLNVTKDGDSYSLRWET (SEQ ID NO: 61)) and 427-438 (EWSEARSWDTES (SEQ ID NO: 62)) of GM-CSF receptor β chain. All the mentioned amino acids are included in SEQ ID NO: 1 of the extracellular domain of the GM-CSF receptor α chain, and SEQ ID NO: 7 of the extracellular domain of the GM-CSF receptor β chain.

In some embodiments, the extracellular region of GM-CSF receptor α chain comprises the amino acid sequence set forth in SEQ ID NO: 1, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 1. In certain embodiments, the nucleotide sequence that encodes the extracellular region of GM-CSF receptor α chain comprises the nucleotide sequence that encodes the amino acid sequence of SEQ ID NO: 1, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 1. In certain embodiments, the nucleotide sequence that encodes the extracellular region of GM-CSF receptor α chain comprises the nucleotide sequence set forth in SEQ ID NO: 2, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 2. In certain embodiments, the extracellular region of GM-CSF receptor α chain comprises the amino acid sequence set forth in SEQ ID NO: 1. In certain embodiments, the nucleotide sequence that encodes the extracellular region of GM-CSF receptor α chain comprises the nucleotide sequence set forth in SEQ ID NO: 2.

In some embodiments, the intracellular region of IL-18 receptor α chain comprises the amino acid sequence set forth in SEQ ID NO: 5, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 5. In certain embodiments, the nucleotide sequence that encodes the intracellular region of IL-18 receptor α chain comprises the nucleotide sequence that encodes the amino acid sequence of SEQ ID NO: 5, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 5. In certain embodiments, the nucleotide sequence that encodes the intracellular region of IL-18 receptor α chain comprises the nucleotide sequence set forth in SEQ ID NO: 6, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 6. In certain embodiments, the intracellular region of IL-18 receptor α chain comprises the amino acid sequence set forth in SEQ ID NO: 5. In certain embodiments, the nucleotide sequence that encodes the intracellular region of IL-18 receptor α chain comprises the nucleotide sequence set forth in SEQ ID NO: 6.

In some embodiments, the extracellular region of GM-CSF receptor β chain comprises the amino acid sequence set forth in SEQ ID NO: 7, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 7. In certain embodiments, the nucleotide sequence that encodes the extracellular region of GM-CSF receptor β chain comprises the nucleotide sequence that encodes the amino acid sequence of SEQ ID NO: 7, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 7. In certain embodiments, the nucleotide sequence that encodes the extracellular region of GM-CSF receptor β chain comprises the nucleotide sequence set forth in SEQ ID NO: 8, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 8. In certain embodiments, the extracellular region of GM-CSF receptor β chain comprises the amino acid sequence set forth in SEQ ID NO: 7. In certain embodiments, the nucleotide sequence that encodes the extracellular region of GM-CSF receptor β chain comprises the nucleotide sequence set forth in SEQ ID NO: 8.

In some embodiments, the intracellular region of IL-18 receptor β chain comprises the amino acid sequence set forth in SEQ ID NO: 11, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 11. In certain embodiments, the nucleotide sequence that encodes the intracellular region of IL-18 receptor β chain comprises the nucleotide sequence that encodes the amino acid sequence of SEQ ID NO: 11, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 11. In certain embodiments, the nucleotide sequence that encodes the intracellular region of IL-18 receptor β chain comprises the nucleotide sequence set forth in SEQ ID NO: 12, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 12. In certain embodiments, the intracellular region of IL-18 receptor β chain comprises the amino acid sequence set forth in SEQ ID NO: 11. In certain embodiments, the nucleotide sequence that encodes the intracellular region of IL-18 receptor β chain comprises the nucleotide sequence set forth in SEQ ID NO: 12.

In some embodiments, the chimeric cytokine receptor comprises a functional portion of the intracellular region of IL-18 receptor α chain and/or β chain which is capable of activating MyD88 signaling.

In certain aspects, the chimeric cytokine receptor of the present disclosure comprise a transmembrane domain, fused in frame or operably linked between the extracellular domain and the intracellular domain. In some embodiments, the first and the second polypeptide may each comprise a transmembrane region, fused in frame or operably linked between the extracellular region and the intracellular region.

The transmembrane domain may be derived from the protein contributing to the extracellular domain (e.g., GM-CSF receptor), the protein contributing to the intracellular domain (e.g., IL-18 receptor), or by a totally different protein. In some instances, the transmembrane domain can be selected or modified by amino acid substitution, deletions, or insertions to minimize interactions with other members of the chimeric cytokine receptor. In some instances, the transmembrane domain can be selected or modified by amino acid substitution, deletions, or insertions to avoid-binding of proteins naturally associated with the transmembrane domain. In certain embodiments, the trans-membrane domain includes additional amino acids to allow for flexibility and/or optimal distance between the domains connected to the transmembrane domain.

The transmembrane domain may be derived either from a natural or from a synthetic source. Where the source is natural, the domain may be derived from any membrane-bound or transmembrane protein. Non-limiting examples of transmembrane domains of particular use in this disclosure may be derived from (i.e. comprise at least the transmem-brane region(s) of) the α, β or ζ chain of the T-cell receptor, CD28, CD3 epsilon, CD45, CD4, CD5, CD8, CD8α, CD9, CD16, CD22, CD33, CD37, CD40, CD64, CD80, CD86, CD134, CD137, CD154. Alternatively, the transmembrane domain may be synthetic, in which case it will comprise predominantly hydrophobic residues such as leucine and valine. For example, a triplet of phenylalanine, tryptophan and/or valine can be found at each end of a synthetic transmembrane domain.

In certain embodiments, it will be desirable to utilize the transmembrane domain of the ζ, η or FcεR1γ chains which contain a cysteine residue capable of disulfide bonding, so that the resulting chimeric protein will be able to form disulfide linked dimers with itself, or with unmodified versions of the ζ,η or FcεR1γ chains or related proteins. In some instances, the transmembrane domain will be selected or modified by amino acid substitution to avoid-binding of such domains to the transmembrane domains of the same or different surface membrane proteins to minimize interactions with other members of the receptor complex. In other cases, it will be desirable to employ the transmembrane domain of ζ, η or FcεR1γ and –β, MB1 (Igα), B29 or CD3-γ, ζ, or η, in order to retain physical association with other members of the receptor complex.

In some embodiments, at least one of the transmembrane regions is derived from the transmembrane domain of IL-18 receptor.

In some embodiments, the first transmembrane region comprises a transmembrane region of IL-18 receptor α chain. In some embodiments, the second transmembrane region comprises a transmembrane region of IL-18 receptor β chain.

In some embodiments, the first transmembrane region comprises a transmembrane region of IL-18 receptor β chain. In some embodiments, the second transmembrane region comprises a transmembrane region of IL-18 receptor α chain.

In some embodiments, the transmembrane domains of the GM18 receptor could be derived from other cytokines, for example but not limited to GM-CSF receptor, common gamma cytokine receptors (e.g., IL-2, IL-7, IL-15), or Th2 cytokine receptors (e.g., IL-4, IL-15).

In some embodiments, the transmembrane region of IL-18 receptor α chain comprises the amino acid sequence set forth in SEQ ID NO: 3, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 3. In certain embodiments, the nucleotide sequence that encodes the transmembrane region of IL-18 receptor α chain comprises the nucleotide sequence that encodes the amino acid sequence of SEQ ID NO: 3, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 3. In certain embodiments, the nucleotide sequence that encodes the transmembrane region of IL-18 receptor α chain comprises the nucleotide sequence set forth in SEQ ID NO: 4, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 4. In certain embodiments, the transmembrane region of IL-18 receptor α chain comprises the amino acid sequence set forth in SEQ ID NO: 3. In certain embodiments, the nucleo-tide sequence that encodes the transmembrane region of IL-18 receptor α chain comprises the nucleotide sequence set forth in SEQ ID NO: 4.

In some embodiments, the transmembrane region of IL-18 receptor β chain comprises the amino acid sequence set forth in SEQ ID NO: 9, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 9. In certain embodiments, the nucleotide sequence that encodes the transmembrane region of IL-18 receptor β chain comprises the nucleotide sequence that encodes the amino acid sequence of SEQ ID NO: 9, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 9. In certain embodiments, the nucleotide sequence that encodes the transmembrane region of IL-18 receptor β chain comprises the nucleotide sequence set forth in SEQ ID NO: 10, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 10. In certain embodiments, the transmembrane region of IL-18 receptor β chain comprises the amino acid sequence set forth in SEQ ID NO: 9. In certain embodiments, the nucleotide sequence that encodes the transmembrane region of IL-18 receptor β chain comprises the nucleotide sequence set forth in SEQ ID NO: 10.

In certain embodiments, at least one of the transmembrane regions is derived from the transmembrane domain of GM-CSF receptor.

In some embodiments, the transmembrane region of GM-CSF receptor α chain comprises the amino acid sequence set forth in SEQ ID NO: 48, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 48. In certain embodiments, the nucleotide sequence that encodes the transmembrane region of GM-CSF receptor α chain comprises the nucleotide sequence that encodes the amino acid sequence of SEQ ID NO: 48, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 48. In certain embodiments, the nucleotide sequence that encodes the transmembrane region of GM-CSF receptor α chain comprises the nucleotide sequence set forth in SEQ ID NO: 49, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 49. In certain embodiments, the transmembrane region of GM-CSF receptor α chain comprises the amino acid sequence set forth in SEQ ID NO: 48. In certain embodiments, the nucleotide sequence that encodes the transmembrane region of GM-CSF receptor α chain comprises the nucleotide sequence set forth in SEQ ID NO: 49.

In some embodiments, the transmembrane region of GM-CSF receptor β chain comprises the amino acid sequence set forth in SEQ ID NO: 50, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 50. In certain embodiments, the nucleotide sequence that encodes the transmembrane region of GM-CSF receptor β chain comprises the nucleotide sequence that encodes the amino acid sequence of SEQ ID NO: 50, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 50. In certain embodiments, the nucleotide sequence that encodes the transmembrane region of GM-CSF receptor β chain comprises the nucleotide sequence set forth in SEQ ID NO: 51, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 51. In certain embodiments, the transmembrane region of GM-CSF receptor β chain comprises the amino acid sequence set forth in SEQ ID NO: 50. In certain embodiments, the nucleotide sequence that encodes the transmembrane region of GM-CSF receptor β chain comprises the nucleotide sequence set forth in SEQ ID NO: 51.

In certain embodiments, the polynucleotide encoding a chimeric cytokine receptor further comprises at least one leader sequence. The leader sequence may be positioned at the amino-terminus of the extracellular domain. The leader sequence may be optionally cleaved from the extracellular domain during cellular processing and localization of the chimeric cytokine receptor to the cellular membrane. The leader sequence may be included in the first and/or the second polypeptide. In some embodiments, both the first and the second polypeptide comprise a leader sequence. In certain embodiments the first and second polypeptides comprise the same leader sequence. In certain embodiments, the first and second polypeptides comprise different leader sequences.

In some embodiments, the first polypeptide further comprises a first leader sequence.

In some embodiments, the first leader sequence is derived from a leader sequence of GM-CSF receptor α chain. In some embodiments, the leader sequence of GM-CSF receptor α chain comprises the amino acid sequence set forth in SEQ ID NO: 13, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 13. In certain embodiments, the nucleotide sequence that encodes the leader sequence of GM-CSF receptor α chain comprises the nucleotide sequence that encodes the amino acid sequence of SEQ ID NO: 13, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 13. In certain embodiments, the nucleotide sequence that encodes the leader sequence of GM-CSF receptor α chain comprises the nucleotide sequence set forth in SEQ ID NO: 14, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 14. In certain embodiments, the leader sequence of GM-CSF receptor α chain comprises the amino acid sequence set forth in SEQ ID NO: 13. In certain embodiments, the nucleotide sequence that encodes the leader sequence of GM-CSF receptor α chain comprises the nucleotide sequence set forth in SEQ ID NO: 14.

In some embodiments, the second polypeptide further comprises a second leader sequence.

In some embodiments, the second leader sequence is derived from a leader sequence of GM-CSF receptor β chain. In some embodiments, the leader sequence of GM-CSF receptor β chain comprises the amino acid sequence set forth in SEQ ID NO: 15, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 15. In certain embodiments, the nucleotide sequence that encodes the leader sequence of GM-CSF receptor β chain comprises the nucleotide sequence that encodes the amino acid sequence of SEQ ID NO: 15, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 15. In certain embodiments, the nucleotide sequence that encodes the leader sequence of GM-CSF receptor β chain comprises the nucleotide sequence set forth in SEQ ID NO: 16, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 16. In certain embodiments, the leader sequence of GM-CSF receptor β chain comprises the amino acid sequence set forth in SEQ ID NO: 15. In certain embodiments, the nucleotide sequence that encodes the leader sequence of GM-CSF receptor β chain comprises the nucleotide sequence set forth in SEQ ID NO: 16.

Additional leader sequences may include those derived from human immunoglobulin heavy chain variable region or CD8α. In some embodiments, the first and/or the second leader sequence may comprise or consist essentially of the amino acid sequence set forth in SEQ ID NOs: 44 or 46 or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NOs: 44 or 46. In certain embodiments, the nucleotide sequence encoding the first and/or the second leader sequence may comprise or consist essentially of the nucleotide sequence that encodes the amino acid sequence of SEQ ID NOs: 44 or 46, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 44 or 46. In certain embodiments, the nucleotide sequence encoding the first and/or the second leader sequence may comprise or consist essentially of the sequence set forth in SEQ ID NO: 45 or 47, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NOs: 45 or 47. In certain embodiments, the first and/or the second leader sequence may comprise or consist essentially of the amino acid sequence of SEQ ID NO: 44 or 46. In certain embodiments, the nucleotide sequence encoding the first and/or the second leader sequence may comprise or consist essentially of the nucleotide sequence set forth in SEQ ID NOs: 45 or 47.

In some embodiments, the first polypeptide comprises the amino acid sequence set forth in SEQ ID NO: 17, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 17. In certain embodiments, the nucleotide sequence that encodes the first polypeptide comprises the nucleotide sequence that encodes the amino acid sequence of SEQ ID NO: 17, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 17. In certain embodiments, the nucleotide sequence that encodes the first polypeptide comprises the nucleotide sequence set forth in SEQ ID NO: 18, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 18. In certain embodiments, the first polypeptide comprises the amino acid sequence set forth in SEQ ID NO: 17. In certain embodiments, the nucleotide sequence that encodes the first polypeptide comprises the nucleotide sequence set forth in SEQ ID NO: 18.

In some embodiments, the second polypeptide comprises the amino acid sequence set forth in SEQ ID NO: 19, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 19. In certain embodiments, the nucleotide sequence that encodes the second polypeptide comprises the nucleotide sequence that encodes the amino acid sequence of SEQ ID NO: 19, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 19. In certain embodiments, the nucleotide sequence that encodes the second polypeptide comprises the nucleotide sequence set forth in SEQ ID NO: 20, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 20. In certain embodiments, the second polypeptide comprises the amino acid sequence set forth in SEQ ID NO: 19. In certain embodiments, the nucleotide sequence that encodes the second polypeptide comprises the nucleotide sequence set forth in SEQ ID NO: 20.

In some embodiments, the sequence encoding the first polypeptide is on a separate polynucleotide sequence than the second sequence encoding the second polypeptide sequence.

In some embodiments, the sequence encoding the first polypeptide is operably linked to the sequence encoding a second polypeptide via a sequence encoding a self-cleaving peptide or an internal ribosome entry site (IRES).

In some embodiments, the self-cleaving peptide is a 2A peptide. Non-limiting examples of self-cleaving peptide sequences includes Thoseaasigna virus 2A (T2A; AEGRGSLLTCGDVEENPGP, SEQ ID NO: 30, EGRGSLLTCGDVEENPGP, SEQ ID NO: 31, or GSGEGRGSLLTCGDVEENPGP, SEQ ID NO: 21); the foot and mouth disease virus (FMDV) 2A sequence (F2A; GSGSRVTELLYRMKRAETYCPRPLLAIHPTEAR-HKQKIVAPVKQLLNFDLLKLAGDV ESNPGP, SEQ ID NO: 32), Sponge (Amphimedon queenslandica) 2A sequence (LLCFLLLLLSGDVELNPGP, SEQ ID NO: 33; or HHFMFLLLLLAGDIELNPGP, SEQ ID NO: 34); acorn worm 2A sequence (Saccoglossus kowalevskii) (WFLVLLSFILSGDIEVNPGP, SEQ ID NO: 35); amphi-oxus (Branchiostoma floridae) 2A sequence (KN-CAMYMLLLSGDVETNPGP, SEQ ID NO: 36; or MVISQLMLKLAGDVEENPGP, SEQ ID NO: 37); porcine teschovirus-1 2A sequence (P2A; GSGATNFSLLKQAGD-VEENPGP, SEQ ID NO: 38); and equine rhinitis A virus 2A sequence (E2A; GSGQCTNYALLKLAGDVESNPGP, SEQ ID NO: 39). In some embodiments, the separation sequence is a naturally occurring or synthetic sequence. In certain embodiments, the separation sequence includes the 2A consensus sequence D-X-E-X-NPGP (SEQ ID NO: 40), in which X is any amino acid residue.

In some embodiments, the self-cleaving 2A peptide comprises the amino acid sequence set forth in SEQ ID NO: 21, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 21. In certain embodiments, the nucleotide sequence that encodes the self-cleaving 2A peptide comprises the nucleotide sequence that encodes the amino acid sequence of SEQ ID NO: 21, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 21. In certain embodiments, the nucleotide sequence that encodes the self-cleaving 2A peptide comprises the nucleotide sequence set forth in SEQ ID NO: 22, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 22. In certain embodiments, the self-cleaving 2A peptide comprises the amino acid sequence set forth in SEQ ID NO: 21. In certain embodiments, the nucleotide sequence that encodes the self-cleaving 2A peptide comprises the nucleotide sequence set forth in SEQ ID NO: 22.

Alternatively, an internal ribosome entry site (IRES) may be used to link the first polypeptide and the second polypeptide. IRES is an RNA element that allows for translation initiation in a cap-independent manner. IRES can link two coding sequences in one bicistronic vector and allow the translation of both proteins in cells.

In some embodiments, the chimeric cytokine receptor comprises the amino acid sequence set forth in SEQ ID NO: 23, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 23. In certain embodiments, the nucleotide sequence that encodes the chimeric cytokine receptor comprises the nucleotide sequence that encodes the amino acid sequence of SEQ ID NO: 23, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 23. In certain embodiments, the nucleotide sequence that encodes the chimeric cytokine receptor comprises the nucleotide sequence set forth in SEQ ID NO: 24, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 24. In certain embodiments, the chimeric cytokine receptor comprises the amino acid sequence set forth in SEQ ID NO: 23. In certain embodiments, the nucleotide sequence that encodes the chimeric cytokine receptor comprises the nucleotide sequence set forth in SEQ ID NO: 24.

In some embodiments, the polynucleotide encoding the chimeric cytokine receptor further comprises a polymerase regulatory region (Pol region). In some embodiments, the Pol region comprises the nucleotide sequence of SEQ ID NO: 25, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 25.

In some embodiments, the polynucleotide encoding the chimeric cytokine receptor comprises the nucleotide sequence that encodes the amino acid sequence of SEQ ID NO: 41, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 41.

In addition to the chimeric cytokine receptor construct, the polynucleotide may further comprise at least one additional gene that encodes an additional peptide. Examples of additional genes can include a transduced host cell selection marker, an in vivo tracking marker, a cytokine, a suicide gene, or some other functional gene. In certain embodiments, the functional additional gene can induce the expression of another molecule. In certain embodiments, the functional additional gene can increase the safety of the chimeric cytokine receptor. For example, the chimeric cytokine receptor construct may comprise an additional gene which is truncated CD19 (tCD19). The tCD19 can be used as a tag. Expression of tCD19 may also help determine transduction efficiency.

Non-limiting examples of classes of additional genes that can be used to increase the effector function of the modified host cells, include (a) secretable cytokines (e.g., but not limited to, GM-CSF, IL-7, IL-12, IL-15, IL-18), (b) membrane bound cytokines (e.g., but not limited to, IL-15), (c) other chimeric cytokine receptors (e.g., but not limited to, IL-2/IL-7, IL-4/IL-7), (d) constitutive active cytokine receptors (e.g., but not limited to, C7R), (e) dominant negative receptors (DNR; e.g., but not limited to TGFRII DNR), (f) ligands of costimulatory molecules (e.g., but not limited to, CD80, 4-1BBL), (g) nuclear factor of activated T-cells (NFATs) (e.g., NFATc1, NFATc2, NFATc3, NFATc4, and NFAT5), (h) antibodies, including fragments thereof and bispecific antibodies (e.g., but not limited to, bispecific T-cell engagers (BiTEs)), (i) chimeric antigen receptors (CARs), or (j) safety switches or suicide genes (e.g., CD20, truncated EGFR or HER2, inducible caspase 9 molecules).

In certain embodiments, the chimeric cytokine receptor construct may comprise an additional gene that encodes GM-CSF. The expression of exogenous GM-CSF may further enhance the function of the host cells expressing the chimeric cytokine receptor of the present disclosure.

In certain embodiments, the functional additional gene is a suicide gene. A suicide gene is a recombinant gene that will cause the host cell that the gene is expressed in to undergo programmed cell death or antibody mediated clearance at a desired time. Suicide genes can function to increase the safety of the chimeric cytokine receptor. In another embodiment, the additional gene is an inducible suicide gene. Non-limiting examples of suicide genes include i) molecules that are expressed on the cell surface and can be targeted with a clinical grade monoclonal antibody including CD20, EGFR or a fragment thereof, HER2 or a fragment thereof, and ii) inducible suicide genes (e.g., but not limited to inducible caspase 9 (see Straathof et al. (2005) *Blood.* 105(11): 4247-4254; US Publ. No. 2011/0286980, each of which are incorporated herein by reference in their entirety for all purposes)).

In certain aspects, chimeric cytokine receptors of the present disclosure may be regulated by a safety switch. As used herein, the term "safety switch" refers to any mechanism that is capable of removing or inhibiting the effect of a chimeric cytokine receptor from a system (e.g., a culture or a subject). Safety switches can function to increase the safety of the chimeric cytokine receptor.

The function of the safety switch may be inducible. Non-limiting examples of safety switches include (a) molecules that are expressed on the cell surface and can be targeted with a clinical grade monoclonal antibody including CD20, EGFR or a fragment thereof, HER2 or a fragment thereof, and (b) inducible suicide genes (e.g., but not limited to herpes simplex virus thymidine kinase (HSV-TK) and inducible caspase 9 (see Straathof et al. (2005) *Blood.* 105(11): 4247-4254; US Publ. No. 2011/0286980, each of which are incorporated herein by reference in their entirety for all purposes).

In some embodiments, the safety switch is a CD20 polypeptide. Expression of human CD20 on the cell surface presents an attractive strategy for a safety switch. The inventors and others have shown that cells that express CD20 can be rapidly eliminated with the FDA approved monoclonal antibody rituximab through complement-mediated cytotoxicity and antibody-dependent cell-mediated cytotoxicity (see e.g., Griffioen, M., et al. *Haematologica* 94, 1316-1320 (2009), which is incorporated herein by reference in its entirety for all purposes). Rituximab is an anti-CD20 monoclonal antibody that has been FDA approved for Chronic Lymphocytic Leukemia (CLL) and Non-Hodgkin's Lymphoma (NHL), among others (Storz, U. *MAbs* 6, 820-837 (2014), which is incorporated herein by reference in its entirety for all purposes). The CD20 safety switch is non-immunogenic and can function as a reporter/selection marker in addition to a safety switch (Bonifant, C. L., et al. *Mol Ther* 24, 1615-1626 (2016); van Loenen, M. M., et al. *Gene Ther* 20, 861-867 (2013); each of which is incorporated herein by reference in its entirety for all purposes).

In certain embodiments, the chimeric cytokine receptor comprises at least one additional gene (i.e., a second gene). In certain embodiments, the chimeric cytokine receptor comprises one second gene. In other embodiments, the chimeric cytokine receptor comprises two additional genes (i.e., a third gene). In yet another embodiment, the chimeric cytokine receptor comprises three additional genes (i.e., a fourth gene). In certain embodiments, the additional genes are separated from each other and the chimeric cytokine receptor construct. For example, they may be separated by 2A sequences and/or an internal ribosomal entry sites (IRES) as described above. In certain examples, the chimeric cytokine receptor can be at any position of the polynucleotide chain.

In various embodiments, the polynucleotide encoding the chimeric cytokine receptor is a DNA molecule.

In various embodiments, the polynucleotide encoding the chimeric cytokine receptor is a RNA molecule.

Vectors

The present disclosure provides recombinant vectors comprising a polynucleotide encoding a chimeric cytokine receptor. Such recombinant vectors may comprise polynucleotides encoding the proteins disclosed above. In certain embodiments, the polynucleotide is operatively linked to at least one regulatory element for expression of the chimeric cytokine receptor.

In certain embodiments, recombinant vectors of the disclosure comprise the nucleotide sequence of SEQ ID NO: 24, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 24. In certain embodiments, recombinant vectors comprise a nucleotide sequence that encodes the amino acid sequence of SEQ ID NO: 23, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 23.

In certain embodiments, the vector is a viral vector. In certain embodiments, the viral vector can be, but is not limited to, a retroviral vector, an adenoviral vector, an adeno-associated virus vector, an alphaviral vector, a herpes virus vector, a baculoviral vector and a vaccinia virus vector.

In some embodiments, the viral vector is a retroviral vector.

In some embodiments, the vector is a non-viral vector. Non-viral vectors suitable for use in this invention include but are not limited to minicircle plasmids, transposon systems (e.g. Sleeping Beauty, piggyBac), or single or double stranded DNA molecules that are used as templates for homology directed repair (HDR) based gene editing.

In certain embodiments, the polynucleotide encoding the chimeric cytokine receptor is operably linked to at least a regulatory element. The regulatory element can be capable of mediating expression of the chimeric cytokine receptor in the host cell. Regulatory elements include, but are not limited to, promoters, enhancers, initiation sites, polyadenylation (polyA) tails, IRES elements, response elements, and termination signals. In certain embodiments, the regulatory element regulates chimeric cytokine receptor expression. In certain embodiments, the regulatory element increased the expression of the chimeric cytokine receptor. In certain embodiments, the regulatory element increased the expression of the chimeric cytokine receptor once the host cell is activated. In certain embodiments, the regulatory element decreases expression of the chimeric cytokine receptor. In certain embodiments, the regulatory element decreases expression of the chimeric cytokine receptor once the host cell is activated.

In one embodiment, the polynucleotide encoding the chimeric cytokine receptor is operably linked to a polymerase regulatory region (Pol region). In some embodiments, the Pol region comprises the nucleotide sequence of SEQ ID NO: 25, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 25.

In certain embodiments, recombinant vectors of the disclosure comprise the nucleotide sequence of SEQ ID NO: 41, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 41.

Modified Host Cells

In another aspect, provided herein is an isolated host cell comprising a chimeric cytokine receptor described herein.

In one aspect, provided herein is an isolated host cell comprising the polynucleotide encoding a chimeric cytokine receptor described herein or the recombinant vector described herein.

In some embodiments, the host cell further expresses a molecule that is capable of binding to a target antigen, such as chimeric antigen receptor (CAR), an antigen specific T cell receptor (TCR) or a bispecific antibody.

CARs are primarily comprised of 1) an antigen-binding domain, such as but not limited to a single-chain variable fragment (scFv) derived from an antigen-specific monoclonal antibody, and 2) a lymphocyte activation domain, such as but not limited to the ζ-chain from the T-cell receptor CD3. These two regions are fused together via a transmembrane domain. A hinge domain is usually required to provide more flexibility and accessibility between the antigen-binding domain and the transmembrane domain. Upon transduction, the lymphocyte expresses the CAR on its surface, and upon contact and ligation with the target antigen, it signals through the lymphocyte activation domain (e.g., CD3ζ chain) inducing cytotoxicity and cellular activation.

CAR constructs may also include co-stimulatory polypeptides to boost the CAR-induced immune response. Non-limiting examples of costimulatory domains include, those derived from 4-1BB (CD137), CD28, CD40, ICOS, CD134 (OX-40), BTLA, CD27, CD30, GITR, CD226, CD79A, MyD88, CD40 and HVEM. The most commonly used co-stimulating molecules include CD28 and 4-1BB, which promotes both T-cell proliferation and cell survival. Another example of co-stimulatory domains is a MyD88/CD40 molecule that can be used with or without the use of a separate dimerization agent. Additional CAR constructs may also include three signaling domains (e.g., CD3ζ, CD28, and 4-1BB), which further improves lymphocyte cell survival and efficacy.

The choice of antigen-binding domain depends upon the type and number of antigens that define the surface of a target cell. For example, the antigen-binding domain may be chosen to recognize an antigen that acts as a cell surface marker on target cells associated with a particular disease state. In certain embodiments, the CARs can be genetically modified to target a tumor antigen of interest by way of engineering a desired antigen-binding domain that specifically binds to an antigen (e.g., on a tumor cell).

T cell receptor (TCR) is a molecule typically found on the surface of T cells, or T lymphocytes, that is responsible for recognizing fragments of antigen as peptides bound to major histocompatibility complex (MHC) molecules. In some embodiments, the isolated host cell comprising a chimeric cytokine receptor described herein expresses an antigen specific TCR. The antigen specific TCR may be endogenously or transgenically expressed. The antigen specific TCR may be an αβ TCR. In some embodiments, the antigen specific T cell receptor specifically binds a tumor antigen.

Bispecific antibodies are antibodies that can simultaneously bind two separate and unique antigens or two different epitopes of the same antigen. In some embodiments, the isolated host cell comprising a chimeric cytokine receptor described herein expresses and secretes a bispecific antibody. By way of example and not limitation, the bispecific antibody may be a bispecific T-cell engager (BiTE), a dual affinity retargeting (DART) antibody, or a bispecific antibody that redirect other immune cells (for example, but not limited to macrophages, NK cells) to kill tumor cells. In some embodiments, the bispecific antibody specifically binds a tumor antigen.

Non-limiting examples of tumor antigens that can be targeted by the modified host cells include carbonic anhydrase EX, alpha-fetoprotein, A3, antigen specific for A33 antibody, Ba 733, BrE3-antigen, CA125, CD1, CD1a, CD3, CD5, CD15, CD16, CD19, CD20, CD21, CD22, CD23, CD25, CD30, CD33, CD38, CD45, CD74, CD79a, CD80, CD123, CD138, colon-specific antigen-p (CSAp), CEA (CEACAM5), CEACAM6, CSAp, EGFR, EGP-I, EGP-2, Ep-CAM, EphA1, EphA2, EphA3, EphA4, EphA5, EphA6, EphA7, EphA8, EphA10, EphB1, EphB2, EphB3, EphB4, EphB6, Flt-I, Flt-3, folate receptor, HLA-DR, human chorionic gonadotropin (HCG) and its subunits, HER2, hypoxia inducible factor (HIF-I), Ia, IL-2, IL-6, IL-8, interleukin 13 receptor α2 (IL13Rα2), insulin growth factor-1 (IGF-I), KC4-antigen, KS-1-antigen, KS1-4, Le-Y, macrophage inhibition factor (MIF), MAGE, MUC1, MUC2, MUC3, MUC4, NCA66, NCA95, NCA90, antigen specific for PAM-4 antibody, placental growth factor, p53, prostatic acid phosphatase, PSA, PSMA, RS5, S100, TAC, TAG-72, tenascin, TRAIL receptors, Tn antigen, Thomson-Friedenreich antigens, tumor necrosis antigens, VEGF, and fibronectin-EDB (oncofetal fibronectin, FN-EDB, EDB).

Additional antigens that may be targeted by the modified host cells described herein include interleukin-13 receptor subunit alpha-2 (IL-13Ra2), A kinase anchor protein 4 (AKAP-4), adrenoceptor beta 3 (ADRB3), anaplastic lymphoma kinase (ALK), immunoglobulin lambda-like polypeptide 1 (IGLL1), androgen receptor, angiopoietin-binding cell surface receptor 2 (Tie 2), B7H3 (CD276), bone marrow stromal cell antigen 2 (BST2), carbonic anhydrase IX (CAIX), CCCTC-binding factor (Zinc Finger Protein)-like (BORIS), CD171, CD179a, CD24, CD300 molecule-like family member f (CD300LF), CD38, CD44v6, CD72, CD79a, CD79b, CD97, chromosome X open reading frame 61 (CXORF61), claudin 6 (CLDN6), CS-1 (CD2 subset 1, CRACC, SLAMF7, CD319, or 19A24), C-type lectin domain family 12 member A (CLEC12A), C-type lectin-like molecule-1 (CLL-1), Cyclin B 1, Cytochrome P450 1B 1 (CYP1B 1), EGF-like module-containing mucin-like hormone receptor-like 2 (EMR2), epidermal growth factor receptor (EGFR), ERG (transmembrane protease, serine 2 (TMPRSS2) ETS fusion gene), ETS translocation-variant gene 6, located on chromosome 12p (ETV6-AML), Fc fragment of IgA receptor (FCAR), Fc receptor-like 5 (FCRL5), Fms-like tyrosine kinase 3 (FLT3), Folate receptor beta, Fos-related antigen 1, Fucosyl GM1, G protein-coupled receptor 20 (GPR20), G protein-coupled receptor class C group 5, member D (GPRC5D), ganglioside GD3, ganglioside GM3, glycoceramide (GloboH), Glypican-3 (GPC3), Hepatitis A virus cellular receptor 1 (HAVCR1), hexasaccharide portion of globoH, high molecular weight-melanoma-associated antigen (HMWMAA), human Telomerase reverse transcriptase (hTERT), interleukin 11 receptor alpha (IL-11Ra), KIT (CD117), leukocyte-associated immunoglobulin-like receptor 1 (LAIR1), leukocyte immunoglobulin-like receptor subfamily A member 2 (LILRA2), Lewis(Y) antigen, lymphocyte antigen 6 complex, locus K 9 (LY6K), lymphocyte antigen 75 (LY75), lymphocyte-specific protein tyrosine kinase (LCK), mammary gland differentiation antigen (NY-BR-1), melanoma cancer testis antigen-1 (MAD-CT-1), melanoma cancer testis antigen-2 (MAD-CT-2), melanoma inhibitor of apoptosis (ML-IAP), mucin 1, cell surface associated (MUC1), N-acetyl glucosaminyl-transferase V (NA17), neural cell adhesion molecule (NCAM), o-acetyl-GD2 ganglioside (OAcGD2), olfactory receptor 51E2 (OR51E2), p53 mutant, paired box protein Pax-3 (PAX3), paired box protein Pax-5 (PAX5), pannexin 3 (PANX3), placenta-specific 1 (PLAC1), platelet-derived growth factor receptor beta (PDGFR-beta), Polysialic acid, proacrosin binding protein sp32 (OY-TES 1), prostate stem cell antigen (PSCA), Protease Serine 21 (PRSS21), Proteasome (Prosome, Macropain) Subunit, Beta Type, 9 (LMP2), Ras Homolog Family Member C (RhoC), sarcoma translocation breakpoints, sialyl Lewis adhesion molecule (sLe), sperm protein 17 (SPA17), squamous cell carcinoma antigen recognized by T cells 3 (SART3), stage-specific embryonic antigen-4 (SSEA-4), synovial sarcoma, X breakpoint 2 (SSX2), TCR gamma alternate reading frame protein (TARP), TGS5, thyroid stimulating hormone receptor (TSHR), Tn antigen (Tn Ag), tumor endothelial marker 1 (TEM1/CD248), tumor endothelial marker 7-related (TEM7R), uroplakin 2 (UPK2), vascular endothelial growth factor receptor 2 (VEGFR2), v-myc avian myelocytomatosis viral oncogene neuroblastoma derived homolog (MYCN), Wilms tumor protein (WT1), and X Antigen Family, Member 1A (XAGE1), or a fragment or variant thereof.

In one embodiment, the host cell comprising a chimeric cytokine receptor of the present disclosure comprises a CAR comprising an extracellular antigen-binding domain that specifically binds human epidermal growth factor receptor 2 (HER2). The HER2 CAR may comprises the amino acid sequence of SEQ ID NO: 26, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 26. In certain embodiments, the nucleotide sequence that encodes the HER2 CAR comprises the nucleotide sequence that encodes the amino acid sequence of SEQ ID NO: 26, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 26. In certain embodiments, the nucleotide sequence that encodes the HER2 CAR comprises the nucleotide sequence set forth in SEQ ID NO: 27, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 27. In certain embodiments, the HER2 CAR comprises the amino acid sequence set forth in SEQ ID NO: 26. In certain embodiments, the nucleotide sequence that encodes the HER2 CAR comprises the nucleotide sequence set forth in SEQ ID NO: 27.

In one embodiment, the host cell comprising a chimeric cytokine receptor of the present disclosure comprises an extracellular antigen-binding domain that specifically binds ephrin type-A receptor 2 (EphA2). The EphA2 CAR may comprises the amino acid sequence of SEQ ID NO: 28, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 28. In certain embodiments, the nucleotide sequence that encodes the EphA2 CAR comprises the nucleotide sequence that encodes the amino acid sequence of SEQ ID NO: 28, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 28. In certain embodiments, the nucleotide sequence that encodes the EphA2 CAR comprises the nucleotide sequence set forth in SEQ ID NO: 29, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 29. In certain embodiments, the EphA2 CAR comprises the amino acid sequence set forth in SEQ ID NO: 28. In certain embodiments, the nucleotide sequence that encodes the EphA2 CAR comprises the nucleotide sequence set forth in SEQ ID NO: 29.

In some embodiments, the nucleotide sequence encoding a CAR is operably linked to at least a regulatory element. The regulatory element can be capable of mediating expression of the CAR in the host cell. Regulatory elements include, but are not limited to, promoters, enhancers, initiation sites, polyadenylation (polyA) tails, IRES elements, response elements, and termination signals. In certain embodiments, the regulatory element regulates CAR expression. In certain embodiments, the regulatory element increased the expression of the CAR. In certain embodiments, the regulatory element increased the expression of the CAR once the host cell is activated. In certain embodiments, the regulatory element decreases expression of the CAR. In certain embodiments, the regulatory element decreases expression of the CAR once the host cell is activated.

In some embodiments, the nucleotide sequence encoding a CAR further comprises a polymerase regulatory region (Pol region). In some embodiments, the Pol region comprises the nucleotide sequence of SEQ ID NO: 25, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 25.

In one embodiment, the nucleotide sequence that encodes the HER2 CAR comprises the nucleotide sequence set forth in SEQ ID NO: 42, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 42.

In one embodiment, the nucleotide sequence that encodes the EphA2 CAR comprises the nucleotide sequence set forth in SEQ ID NO: 43, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 43.

In various embodiments, the host cell is an immune cell. The host cell may be any immune cell that expresses GM-CSF upon activation. In some embodiments, the immune cell may be a T-cell or a natural killer (NK) cell.

In various embodiments, the host cell is a T-cell. T-cells may include, but are not limited to, thymocytes, naive T lymphocytes, immature T lymphocytes, mature T lymphocytes, resting T lymphocytes, or activated T lymphocytes. A T-cell can be a T helper (Th) cell, for example a T helper 1 (Th1) or a T helper 2 (Th2) cell. The T-cell can be a helper T-cell (HTL; CD4+ T-cell) CD4+ T-cell, a cytotoxic T-cell (CTL; CD8+ T-cell), a tumor infiltrating cytotoxic T-cell (TIL; CD8+ T-cell), CD4+ CD8+ T-cell, or any other subset of T-cells. Other illustrative populations of T-cells suitable for use in particular embodiments include naive T-cells memory T-cells, and NKT cells.

In some embodiments, the T-cell is selected from a CD8+ T-cell, a CD4+ T-cell, a cytotoxic T-cell, an αβ T-cell receptor (TCR) T-cell, a natural killer T (NKT) cell, a γδ T-cell, a memory T-cell, a T-helper cell, and a regulatory T-cell (Treg).

In various embodiments, the host cell is a NK cell. NK cell refers to a differentiated lymphocyte with a CD3– CD16+, CD3– CD56+, CD16+ CD56+ and/or CD57+ TCR- phenotype.

In various embodiments, the host cell has been activated and/or expanded ex vivo.

In various embodiments, the host cell is an allogeneic cell. In various embodiments, the host cell is an autologous cell.

In some embodiments, the host cell is isolated from a subject having a tumor. In some embodiments, the tumor can be found within, but not limited to, breast tissue, prostate tissue, bladder tissue, oral and/or dental tissue, head and/or neck tissue, stomach tissue, liver tissue, colorectal tissue, lung tissue, brain tissue, ovary, cervix, esophagus, skin, lymph nodes, and/or bone. In some embodiments, the tumor is a cancer. In some embodiments, the cancer can be, but not limited to, breast cancer, prostate cancer, stomach cancer, ovary cancer, uterine serous endometrial carcinoma, uterine cervix cancer, bladder cancer, oral squamous cell carcinoma, head and/or neck squamous cell carcinoma, sarcoma, esophagus cancer, colorectal cancer, lung cancer, brain tumors, skin cancer, melanoma, bone, pediatric solid tumors and brain tumors, and/or lymphoma.

In certain embodiments, the host cell is isolated from a subject having a tumor, wherein one or more cells of the tumor cells express HER2. Non-limiting examples of tumors that express HER2 include brain, breast, stomach, ovary, uterine serous endometrial carcinoma, colon, bladder, lung, uterine cervix, head and neck, sarcoma, bone tumors, and esophagus cancer.

In certain embodiments, the host cell is isolated from a subject having a tumor, wherein one or more cells of the tumor cells express EphA2. Non-limiting examples of tumors that express EphA2 include breast, prostate, urinary bladder, skin, lung, ovary, sarcoma, bone tumors or brain cancer.

In some embodiments, the host cell is derived from a blood, marrow, tissue, or a tumor sample.

In certain aspects, the present disclosure provides a method of generating an isolated host cell described herein. The method includes genetically modifying the host cell with a polynucleotide or a recombinant vector that encodes a chimeric cytokine receptor described herein. The method may further comprise genetically modifying the host cell to express a chimeric antigen receptor (CAR), an antigen specific T cell receptor (TCR) and/or a bispecific antibody. In some embodiments, the genetic modifying step is conducted via viral gene delivery. In some embodiments, the genetic modifying step is conducted via non-viral gene delivery. In some embodiments, the genetically modifying step is conducted ex vivo. In some embodiments, the method further comprises activation and/or expansion of the host cell ex vivo before, after and/or during said genetic modification.

Isolation/Enrichment

The host cells may be autologous/autogeneic ("self") or non-autologous ("non-self," e.g., allogeneic, syngeneic or xenogeneic). In certain embodiments, the host cells are obtained from a mammalian subject. In other embodiments, the host cells are obtained from a primate subject. In certain embodiments, the host cells are obtained from a human subject.

Lymphocytes can be obtained from sources such as, but not limited to, peripheral blood mononuclear cells, bone marrow, lymph nodes tissue, cord blood, thymus issue, tissue from a site of infection, ascites, pleural effusion, spleen tissue, and tumors. Lymphocytes may also be generated by differentiation of stem cells. In certain embodiments, lymphocytes can be obtained from blood collected from a subject using techniques generally known to the skilled person, such as sedimentation, e.g., FICOLL™ separation.

In certain embodiments, cells from the circulating blood of a subject are obtained by apheresis. An apheresis device typically contains lymphocytes, including T-cells, monocytes, granulocytes, B cells, other nucleated white blood cells, red blood cells, and platelets. In certain embodiments, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations. A washing step may be accomplished by methods known to those in the art, such as, but not limited to, using a semiautomated flowthrough centrifuge (e.g., Cobe 2991 cell processor, or the Baxter CytoMate). After washing, the cells may be resuspended in a variety of biocompatible buffers, cell culture medias, or other saline solution with or without buffer.

In certain embodiments, host cells can be isolated from peripheral blood mononuclear cells (PBMCs) by lysing the red blood cells and depleting the monocytes. As an example, the cells can be sorted by centrifugation through a PER- COLL™ gradient. In certain embodiments, after isolation of PBMC, both cytotoxic and helper T lymphocytes can be sorted into naive, memory, and effector T-cell subpopulations either before or after activation, expansion, and/or genetic modification.

In certain embodiments, T lymphocytes can be enriched. For example, a specific subpopulation of T lymphocytes, expressing one or more markers such as, but not limited to, CD3, CD4, CD8, CD14, CD15, CD16, CD19, CD27, CD28, CD34, CD36, CD45RA, CD45RO, CD56, CD62, CD62L, CD122, CD123, CD127, CD235a, CCR7, HLA-DR or a combination thereof using either positive or negative selection techniques. In certain embodiments, the T lymphocytes for use in the compositions of the disclosure do not express or do not substantially express one or more of the following markers: CD57, CD244, CD160, PD-1, CTLA4, TIM3, and LAG3.

In certain embodiments, NK cells can be enriched. For example, a specific subpopulation of T lymphocytes, expressing one or more markers such as, but not limited to, CD2, CD16, CD56, CD57, CD94, CD122 or a combination thereof using either positive or negative selection techniques.

Stimulation/Activation

In order to reach sufficient therapeutic doses of host cell compositions, host cells are often subjected to one or more rounds of stimulation/activation. In certain embodiments, a method of producing host cells for administration to a subject comprises stimulating the host cells to become activated in the presence of one or more stimulatory signals or agents (e.g., compound, small molecule, e.g., small organic molecule, nucleic acid, polypeptide, or a fragment, isoform, variant, analog, or derivative thereof). In certain embodiments, a method of producing host cells for administration to a subject comprises stimulating the host cells to become activated and to proliferate in the presence of one or more stimulatory signals or agents.

Host cells (e.g., T lymphocytes and NK cells) can be activated by inducing a change in their biologic state by which the cells express activation markers, produce cytokines, proliferate and/or become cytotoxic to target cells. All these changes can be produced by primary stimulatory signals. Co-stimulatory signals amplify the magnitude of the primary signals and suppress cell death following initial stimulation resulting in a more durable activation state and thus a higher cytotoxic capacity.

T cells can be activated generally using methods as described, for example, in U.S. Pat. Nos. 6,352,694; 6,534, 055; 6,905,680; 6,692,964; 5,858,358; 6,887,466; 6,905, 681; 7,144,575; 7,067,318; 7,172,869; 7,232,566; 7,175, 843; 5,883,223; 6,905,874; 6,797,514; and 6,867,041, each of which is incorporated herein by reference in its entirety.

In certain embodiments, the T-cell based host cells can be activated by binding to an agent that activates CD3ζ.

In other embodiments, a CD2-binding agent may be used to provide a primary stimulation signal to the T-cells. For example, and not by limitation, CD2 agents include, but are not limited to, CD2 ligands and anti-CD2 antibodies, e.g., the Tl 1.3 antibody in combination with the Tl 1.1 or Tl 1.2 antibody (Meuer, S. C. et al. (1984) Cell 36:897-906) and the 9.6 antibody (which recognizes the same epitope as TI 1.1) in combination with the 9-1 antibody (Yang, S. Y. et al. (1986) J. Immunol. 137:1097-1100). Other antibodies which bind to the same epitopes as any of the above described antibodies can also be used.

In certain embodiments, the host cells are activated by administering phorbol myristate acetate (PMA) and ionomycine. In certain embodiments, the host cells are activated by administering an appropriate antigen that induces activation and then expansion. In certain embodiments, PMA, ionomycin, and/or appropriate antigen are administered with CD3 induce activation and/or expansion.

In general, the activating agents used in the present disclosure includes, but is not limited to, an antibody, a fragment thereof and a proteinaceous binding molecule with antibody-like functions. Examples of (recombinant) antibody fragments are Fab fragments, Fv fragments, single-chain Fv fragments (scFv), a divalent antibody fragment such as an (Fab)2'-fragment, diabodies, triabodies (Iliades, P., et al., FEBS Lett (1997) 409, 437-441), decabodies (Stone, E., et al., Journal of Immunological Methods (2007) 318, 88-94) and other domain antibodies (Holt, L. J., et al., Trends Biotechnol. (2003), 21, 11, 484-490). The divalent antibody fragment may be an (Fab)2'-fragment, or a divalent single-chain Fv fragment while the monovalent antibody fragment may be selected from the group consisting of a Fab fragment, a Fv fragment, and a single-chain Fv fragment (scFv).

In certain embodiments, one or more binding sites of the CD3ζ agents may be a bivalent proteinaceous artificial binding molecule such as a dimeric lipocalin mutein (i.e., duocalin). In certain embodiments the receptor binding reagent may have a single second binding site, (i.e., monovalent). Examples of monovalent agents include, but are not limited to, a monovalent antibody fragment, a proteinaceous binding molecule with antibody-like binding properties or an MHC molecule. Examples of monovalent antibody fragments include, but are not limited to a Fab fragment, a Fv fragment, and a single-chain Fv fragment (scFv), including a divalent single-chain Fv fragment.

The agent that specifically binds CD3 includes, but is not limited to, an anti-CD3-antibody, a divalent antibody fragment of an anti-CD3 antibody, a monovalent antibody fragment of an anti-CD3-antibody, and a proteinaceous CD3-binding molecule with antibody-like binding properties. A proteinaceous CD3-binding molecule with antibody-like binding properties can be an aptamer, a mutein based on a polypeptide of the lipocalin family, a glubody, a protein based on the ankyrin scaffold, a protein based on the crystalline scaffold, an adnectin, and an avimer. It also can be coupled to a bead.

In certain embodiments, the activating agent (e.g., CD3-binding agents) can be present in a concentration of about 0.1 to about 10 µg/ml. In certain embodiments, the activating agent (e.g., CD3-binding agents) can be present in a concentration of about 0.2 µg/ml to about 9 µg/ml, about 0.3 µg/ml to about 8 µg/ml, about 0.4 µg/ml to about 7 µg/ml, about 0.5 µg/ml to about 6 µg/ml, about 0.6 µg/ml to about 5 µg/ml, about 0.7 µg/ml to about 4 µg/ml, about 0.8 µg/ml to about 3 µg/ml, or about 0.9 µg/ml to about 2 µg/ml. In certain embodiments, the activating agent (e.g., CD3-binding agents) is administered at a concentration of about 0.1 µg/ml, about 0.2 µg/ml, about 0.3 µg/ml, about 0.4 µg/ml, about 0.5 µg/ml, about 0.6 µg/ml, about 0.7 µg/ml, about 0.8 µM, about 0.9 µg/ml, about 1 µg/ml, about 2 µg/ml, about 3 µg/ml, about 4 µM, about 5 µg/ml, about 6 µg/ml, about 7 µg/ml, about 8 µg/ml, about 9 µg/ml, or about 10 µg/ml. In certain embodiments, the CD3-binding agents can be present in a concentration of 1 µg/ml.

NK cells can be activated generally using methods as described, for example, in U.S. Pat. Nos. 7,803,376, 6,949, 520, 6,693,086, 8,834,900, 9,404,083, 9,464,274, 7,435,596, 8,026,097, 8,877,182; U.S. Patent Applications US2004/ 0058445, US2007/0160578, US2013/0011376, US2015/

0118207, US2015/0037887; and PCT Patent Application WO2016/122147, each of which is incorporated herein by reference in its entirety.

In certain embodiments, the NK based host cells can be activated by, for example and not limitation, inhibition of inhibitory receptors on NK cells (e.g., KIR2DL1, KIR2DL2/ 3, KIR2DL4, KIR2DL5A, KIR2DL5B, KIR3DL1, KIR3DL2, KIR3DL3, LILRB1, NKG2A, NKG2C, NKG2E or LILRB5 receptor).

In certain embodiments, the NK based host cells can be activated by, for example and not limitation, feeder cells (e.g., native K562 cells or K562 cells that are genetically modified to express 4-1BBL and cytokines such as IL15 or IL21).

In other embodiments, interferons or macrophage-derived cytokines can be used to activate NK cells. For example and not limitation, such interferons include but are not limited to interferon alpha and interferon gamma, and such cytokines include but are not limited to IL-15, IL-2, IL-21.

In certain embodiments, the NK activating agent can be present in a concentration of about 0.1 to about 10 µg/ml. In certain embodiments, the NK activating agent can be present in a concentration of about 0.2 µg/ml to about 9 µg/ml, about 0.3 µg/ml to about 8 µg/ml, about 0.4 µg/ml to about 7 µg/ml, about 0.5 µg/ml to about 6 µg/ml, about 0.6 µg/ml to about 5 µg/ml, about 0.7 µg/ml to about 4 µg/ml, about 0.8 µg/ml to about 3 µg/ml, or about 0.9 µg/ml to about 2 µg/ml. In certain embodiments, the NK activating agent is administered at a concentration of about 0.1 µg/ml, about 0.2 µg/ml, about 0.3 µg/ml, about 0.4 µg/ml, about 0.5 µg/ml, about 0.6 µg/ml, about 0.7 µg/ml, about 0.8 µg/ml, about 0.9 µg/ml, about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, or about 10 µg/ml. In certain embodiments, the NK activating agent can be present in a concentration of 1 µg/ml.

In certain embodiments, the activating agent is attached to a solid support such as, but not limited to, a bead, an absorbent polymer present in culture plate or well or other matrices such as, but not limited to, Sepharose or glass; may be expressed (such as in native or recombinant forms) on cell surface of natural or recombinant cell line by means known to those skilled in the art.

Polynucleotide Transfer

In certain embodiments, the host cells are genetically modified to express a chimeric cytokine receptor described above. In certain embodiments, the host cells are further genetically modified to express a CAR, TCR or bispecific antibody described above. The host cells can be genetically modified after stimulation/activation. In certain embodiments, the host cells are modified within 12 hours, 16 hours, 24 hours, 36 hours, or 48 hours of stimulation/activation. In certain embodiments, the cells are modified within 16 to 24 hours after stimulation/activation. In certain embodiments, the host cells are modified within 24 hours.

In order to genetically modify the host cell to express the chimeric cytokine receptor or other related molecule (e.g., CAR, TCR or bispecific antibody), the polynucleotide construct must be transferred into the host cell. Polynucleotide transfer may be via viral or non-viral gene methods. Suitable methods for polynucleotide delivery for use with the current methods include any method known by those of skill in the art, by which a polynucleotide can be introduced into an organelle, cell, tissue or organism.

In some embodiments, polynucleotides are transferred to the cell in a non-viral vector. Non-viral vectors suitable for use in this invention include but are not limited to minicircle plasmids, transposon systems (e.g. Sleeping Beauty, piggy-Bac), or single or double stranded DNA molecules that are used as templates for homology directed repair (HDR) based gene editing.

Nucleic acid vaccines can be used to transfer polynucleotides into the host cells. Such vaccines include, but are not limited to non-viral polynucleotide vectors, "naked" DNA and RNA, and viral vectors. Methods of genetically modifying cells with these vaccines, and for optimizing the expression of genes included in these vaccines are known to those of skill in the art.

In certain embodiments, the host cells can be genetically modified by methods ordinarily used by one of skill in the art. In certain embodiments, the host cells can be transduced via retroviral transduction. References describing retroviral transduction of genes are Anderson et al., U.S. Pat. No. 5,399,346; Mann et al., Cell 33:153 (1983); Temin et al., U.S. Pat. No. 4,650,764; Temin et al., U.S. Pat. No. 4,980, 289; Markowitz et al., J. Virol. 62:1120 (1988); Temin et al., U.S. Pat. No. 5,124,263; International Patent Publication No. WO 95/07358, published Mar. 16, 1995, by Dougherty et al.; and Kuo et al., Blood 82:845 (1993), each of which is incorporated herein by reference in its entirety.

One method of genetic modification includes ex vivo modification. Various methods are available for transfecting cells and tissues removed from a subject via ex vivo modification. For example, retroviral gene transfer in vitro can be used to genetically modified cells removed from the subject and the cell transferred back into the subject. See e.g., Wilson et al., Science, 244:1344-1346, 1989 and Nabel et al., Science, 244(4910):1342-1344, 1989, both of which are incorporated herein by reference in their entity. In certain embodiments, the host cells may be removed from the subject and transfected ex vivo using the polynucleotides (e.g., expression vectors) of the disclosure. In certain embodiments, the host cells obtained from the subject can be transfected or transduced with the polynucleotides (e.g., expression vectors) of the disclosure and then administered back to the subject.

Another method of gene transfer includes injection. In certain embodiments, a cell or a polynucleotide or viral vector may be delivered to a cell, tissue, or organism via one or more injections (e.g., a needle injection). Non-limiting methods of injection include injection of a composition (e.g., a saline based composition). Polynucleotides can also be introduced by direct microinjection. Non-limiting sites of injection include, subcutaneous, intradermal, intramuscular, intranodal (allows for direct delivery of antigen to lymphoid tissues). intravenous, intraprotatic, intratumor, intralymphatic (allows direct administration of DCs) and intraperitoneal. It is understood that proper site of injection preparation is necessary (e.g., shaving of the site of injection to observe proper needle placement).

Electroporation is another method of polynucleotide delivery. See e.g., Potter et al., (1984) Proc. Nat'l Acad. Sci. USA, 81, 7161-7165 and Tur-Kaspa et al., (1986) Mol. Cell Biol., 6, 716-718, both of which are incorporated herein in their entirety for all purposes. Electroporation involves the exposure of a suspension of cells and DNA to a high-voltage electric discharge. In certain embodiments, cell wall-degrading enzymes, such as pectin-degrading enzymes, can be employed to render the host cells more susceptible to genetic modification by electroporation than untreated cells. See e.g., U.S. Pat. No. 5,384,253, incorporated herein by reference in its entirety for all purposes.

In vivo electroporation involves a basic injection technique in which a vector is injected intradermally in a subject.

Electrodes then apply electrical pulses to the intradermal site causing the cells localized there (e.g., resident dermal dendritic cells), to take up the vector. These tumor antigen-expressing dendritic cells activated by local inflammation can then migrate to lymph-nodes.

Methods of electroporation for use with this invention include, for example, Sardesai, N. Y., and Weiner, D. B., Current Opinion in Immunotherapy 23:421-9 (2011) and Ferraro, B. et al., Human Vaccines 7:120-127 (2011), both of which are hereby incorporated by reference herein in their entirety for all purposes.

Additional methods of polynucleotide transfer include liposome-mediated transfection (e.g., polynucleotide entrapped in a lipid complex suspended in an excess of aqueous solution. See e.g., Ghosh and Bachhawat, (1991) In: Liver Diseases, Targeted Diagnosis and Therapy Using Specific Receptors and Ligands. pp. 87-104). Also contemplated is a polynucleotide complexed with Lipofectamine, or Superfect); DEAE-dextran (e.g., a polynucleotide is delivered into a cell using DEAE-dextran followed by polyethylene glycol. See e.g., Gopal, T. V., Mol Cell Biol. 1985 May; 5(5):1188-90); calcium phosphate (e.g., polynucleotide is introduced to the cells using calcium phosphate precipitation. See e.g., Graham and van der Eb, (1973) Virology, 52, 456-467; Chen and Okayama, Mol. Cell Biol., 7(8):2745-2752, 1987), and Rippe et al., Mol. Cell Biol., 10:689-695, 1990); sonication loading (introduction of a polynucleotide by direct sonic loading. See e.g., Fechheimer et al., (1987) Proc. Nat'l Acad. Sci. USA, 84, 8463-8467); microprojectile bombardment (e.g., one or more particles may be coated with at least one polynucleotide and delivered into cells by a propelling force. See e.g., U.S. Pat. Nos. 5,550,318; 5,538,880; 5,610,042; and PCT Application WO 94/09699; Klein et al., (1987) Nature, 327, 70-73, Yang et al., (1990) Proc. Nat'l Acad. Sci. USA, 87, 9568-9572); and receptor-mediated transfection (e.g., selective uptake of macromolecules by receptor-mediated endocytosis that will be occurring in a target cell using cell type-specific distribution of various receptors. See e.g., Wu and Wu, (1987) J. Biol. Chem., 262, 4429-4432; Wagner et al., Proc. Natl. Acad. Sci. USA, 87(9):3410-3414, 1990; Perales et al., Proc. Natl. Acad. Sci. USA, 91:4086-4090, 1994; Myers, EPO 0273085; Wu and Wu, Adv. Drug Delivery Rev., 12:159-167, 1993; Nicolau et al., (1987) Methods Enzymol., 149, 157-176), each reference cited here is incorporated by reference in their entirety for all purposes.

In further embodiments, host cells are genetically modified using gene editing with homology-directed repair (HDR). Homology-directed repair (HDR) is a mechanism used by cells to repair double strand DNA breaks. In HDR, a donor polynucleotide with homology to the site of the double strand DNA break is used as a template to repair the cleaved DNA sequence, resulting in the transfer of genetic information from the donor polynucleotide to the DNA. As such, new nucleic acid material may be inserted or copied into a target DNA cleavage site. Double strand DNA breaks in host cells may be induced by a site-specific nuclease. The term "site-specific nuclease" as used herein refers to a nuclease capable of specifically recognizing and cleaving a nucleic acid (DNA or RNA) sequence. Suitable site-specific nucleases for use in the present invention include, but are not limited to, RNA-guided endonuclease (e.g., CRISPR-associated (Cas) proteins), zinc finger nuclease, a TALEN nuclease, or mega-TALEN nuclease. For example, a site-specific nuclease (e.g., a Cas9+ guide RNA) capable of inducing a double strand break in a target DNA sequence is introduced to a host cell, along with a donor polynucleotide encoding a chimeric cytokine receptor of the present disclosure and optionally an additional protein (e.g., CAR, TCR or bispecific antibody).

Expansion/Proliferation

After the host cells are activated and transduced, the cells are cultured to proliferate. T-cells may be cultured for at least 1, 2, 3, 4, 5, 6, or 7 days, at least 2 weeks, at least 1, 2, 3, 4, 5, or 6 months or more with 1, 2, 3, 4, 5, 6, 7, 8, 9, or 10 or more rounds of expansion.

Agents that can be used for the expansion of T-cells can include interleukins, such as IL-2, IL-7, IL-15, or IL-21 (see for example Cornish et al. 2006, Blood. 108(2):600-8, Bazdar and Sieg, 2007, Journal of Virology, 2007, 81(22): 12670-12674, Battalia et al, 2013, Immunology, 139(1):109-120). Other illustrative examples for agents that may be used for the expansion of T-cells are agents that bind to CD8, CD45 or CD90, such as αCD8, αCD45 or αCD90 antibodies. Illustrative examples of T-cell population including antigen-specific T-cells, T helper cells, cytotoxic T-cells, memory T-cell (an illustrative example of memory T-cells are CD62L|CD8| specific central memory T-cells) or regulatory T-cells (an illustrative example of Treg are CD4+CD25+CD45RA+ Treg cells).

Additional agents that can be used to expand T lymphocytes includes methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety.

In certain embodiments, the agent(s) used for expansion (e.g., IL-2) are administered at about 20 units/ml to about 200 units/ml. In certain embodiments, the agent(s) used for expansion (e.g., IL-2) are administered at about 25 units/ml to about 190 units/ml, about 30 units/ml to about 180 units/ml, about 35 units/ml to about 170 units/ml, about 40 units/ml to about 160 units/ml, about 45 units/ml to about 150 units/ml, about 50 units/ml to about 140 units/ml, about 55 units/ml to about 130 units/ml, about 60 units/ml to about 120 units/ml, about 65 units/ml to about 110 units/ml, about 70 units/ml to about 100 units/ml, about 75 units/ml to about 95 units/ml, or about 80 units/ml to about 90 units/ml. In certain embodiments, the agent(s) used for expansion (e.g., IL-2) are administered at about 20 units/ml, about 25 units/ml, about 30 units/ml, 35 units/ml, 40 units/ml, 45 units/ml, about 50 units/ml, about 55 units/ml, about 60 units/ml, about 65 units/ml, about 70 units/ml, about 75 units/ml, about 80 units/ml, about 85 units/ml, about 90 units/ml, about 95 units/ml, about 100 units/ml, about 105 units/ml, about 110 units/ml, about 115 units/ml, about 120 units/ml, about 125 units/ml, about 130 units/ml, about 135 units/ml, about 140 units/ml, about 145 units/ml, about 150 units/ml, about 155 units/ml, about 160 units/ml, about 165 units/ml, about 170 units/ml, about 175 units/ml, about 180 units/ml, about 185 units/ml, about 190 units/ml, about 195 units/ml, or about 200 units/ml. In certain embodiments, the agent(s) used for expansion (e.g., IL-2) are administered at about 5 mg/ml to about 10 ng/ml. In certain embodiments, the agent(s) used for expansion (e.g., IL-2) are administered at about 5.5 ng/ml to about 9.5 ng/ml, about 6 ng/ml to about 9 ng/ml, about 6.5 ng/ml to about 8.5 ng/ml, or about 7 ng/ml to about 8 ng/ml. In certain embodiments, the agent(s) used for expansion (e.g., IL-2) are administered at about 5 ng/ml, 6 ng/ml, 7 ng/ml, 8 ng/ml, 9, ng/ml, or 10 ng/ml.

After the host cells are activated and transduced, the cells are cultured to proliferate. NK cells may be cultured for at least 1, 2, 3, 4, 5, 6, or 7 days, at least 2 weeks, at least 1, 2, 3, 4, 5, or 6 months or more with 1, 2, 3, 4, 5, 6, 7, 8, 9, or 10 or more rounds of expansion.

Agents that can be used for the expansion of natural killer cells can include agents that bind to CD16 or CD56, such as for example αCD16 or αCD56 antibodies. In certain embodiments, the binding agent includes antibodies (see for example Hoshino et al, Blood. 1991 Dec. 15; 78(12):3232-40.). Other agents that may be used for expansion of NK cells may be IL-15 (see for example Vitale et al. 2002. The Anatomical Record. 266:87-92, which is hereby incorporated by reference in its entirety for all purposes).

Conditions appropriate for T-cell culture include an appropriate media (e.g., Minimal Essential Media (MEM), RPMI Media 1640, Lonza RPMI 1640, Advanced RPMI, Clicks, AIM-V, DMEM, a-MEM, F-12, TexMACS, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion).

Examples of other additives for host cell expansion include, but are not limited to, surfactant, piasmanate, pH buffers such as HEPES, and reducing agents such as N-acetyl-cysteine and 2-mercaptoethanol, Antibiotics (e.g., penicillin and streptomycin), are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In certain embodiments, host cells of the present disclosure may be modified such that the expression of an endogenous TCR, MHC molecule, or other immunogenic molecule is decreased or eliminated. When allogeneic cells are used, rejection of the therapeutic cells may be a concern as it may cause serious complications such as the graft-versus-host disease (GvHD). Although not wishing to be bound by theory, immunogenic molecules (e.g., endogenous TCRs and/or MHC molecules) are typically expressed on the cell surface and are involved in self vs non-self discrimination. Decreasing or eliminating the expression of such molecules may reduce or eliminate the ability of the therapeutic cells to cause GvHD.

In certain embodiments, expression of an endogenous TCR in the host cells is decreased or eliminated. In a particular embodiment, expression of an endogenous TCR (e.g., a(3 TCR) in the host cells is decreased or eliminated. Expression of the endogenous TCR may be decreased or eliminated by disrupting the TRAC locus, TCR beta constant locus, and/or CD3 locus. In certain embodiments, expression of an endogenous TCR may be decreased or eliminated by disrupting one or more of the TRAC, TRBC1, TRBC2, CD3E, CD3G, and/or CD3D locus.

In certain embodiments, expression of one or more endogenous MHC molecules in the host cells is decreased or eliminated. Modified MHC molecule may be an MHC class I or class II molecule. In certain embodiments, expression of an endogenous MHC molecule may be decreased or eliminated by disrupting one or more of the MHC, β2M, TAP1, TAP2, CIITA, RFX5, RFXAP and/or RFXANK locus.

Expression of an endogenous TCR, an MHC molecule, and/or any other immunogenic molecule in the host cell can be disrupted using genome editing techniques such as Clustered regularly interspaced short palindromic repeats (CRISPR)/Cas, zinc finger nucleases (ZFNs), transcription activator-like effector nucleases (TALENs), and Meganucleases. These genome editing methods may disrupt a target gene by entirely knocking out all of its output or partially knocking down its expression. In a particular embodiment, expression of the endogenous TCR, an MHC molecule and/or any other immunogenic molecule in the host cell is disrupted using the CRISPR/Cas technique.

Pharmaceutical Compositions

In some embodiments, the compositions comprise one or more polypeptides of the chimeric cytokine receptor and other related molecules (e.g., CARs, TCRs or bispecific antibodies), polynucleotides, vectors comprising same, and cell compositions, as disclosed herein. Compositions of the present disclosure include, but are not limited to pharmaceutical compositions.

In one aspect, the present disclosure provides a pharmaceutical composition comprising a polynucleotide or a recombinant vector encoding a chimeric cytokine receptor described herein, and a pharmaceutically accepted carrier and/or excipient.

In another aspect, the present disclosure provides pharmaceutical composition comprising the modified host cells comprising a chimeric cytokine receptor described herein and a pharmaceutically acceptable carrier and/or excipient.

Examples of pharmaceutical carriers include but are not limited to sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

Compositions comprising modified host cells disclosed herein may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Compositions comprising modified host cells disclosed herein may comprise one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose.

In some embodiments, the compositions are formulated for parenteral administration, e.g., intravascular (intravenous or intraarterial), intraperitoneal, intratumoral, intraventricular, intrapleural or intramuscular administration. The parenteral preparation can be enclosed in ampoules, disposable syringes or multiple dose vials made of glass or plastic. An injectable pharmaceutical composition is preferably sterile. In some embodiments, the composition is reconstituted from a lyophilized preparation prior to administration.

In some embodiments, the modified host cells may be mixed with substances that adhere or penetrate then prior to their administration, e.g., but not limited to, nanoparticles.

Therapeutic Methods

In one aspect, the present disclosure provides a method of enhancing effector function of an immune cell, comprising genetically modifying the cell with the polynucleotide or the recombinant vector encoding a chimeric cytokine receptor. In some embodiments, the immune cell expresses a chimeric antigen receptor (CAR), an antigen specific T cell receptor (TCR) and/or a bispecific antibody. In some embodiments, the immune cell expresses GM-C SF upon activation.

In some embodiments, the effector function is one or more of expansion, persistence, and/or tumor killing activity.

The terms "expand" or "expansion" when used in relation to an immune cell refer to the ability of the immune cell to undergo cellular proliferation (i.e., to increase the number of cells). The terms used herein encompass both in vivo and in vitro immune cell expansion.

The terms "persist" or "persistence" when used in relation to an immune cell refer to the ability of the immune cell (and/or its progenies) to be maintained in a recipient (e.g., a subject) for a period of time. The terms used herein encompass both in vivo and in vitro immune cell persistence.

The term "tumor killing activity" as used herein refers to the ability of an immune cell to inhibit tumor growth and/or to kill the tumor cells (e.g., cancer cells).

In one aspect, the present disclosure provides a method of treating a disease comprising administering to the subject an effective amount of the host cell comprising a chimeric cytokine receptor described herein, or the pharmaceutical composition comprising the host cells. In some embodiments, the disease is cancer. In some embodiments, the cancer is a solid tumor.

In one aspect, the present disclosure provides a method for treating a tumor in a subject in need thereof. A therapeutically effective amount of the modified host cells comprising a chimeric cytokine receptor described herein or the pharmaceutical composition comprising the host cells is administered to the subject.

The term "tumor" refers to a benign or malignant abnormal growth of tissue. The term "tumor" includes cancer. Examples of tumors are, but not limited to, the soft tissue tumors (e.g., lymphomas), and tumors of the blood and blood-forming organs (e.g., leukemias), and solid tumors, which is one that grows in an anatomical site outside the bloodstream (e.g., carcinomas). Examples of cancer include, but are not limited to, carcinoma, lymphoma, blastoma, sarcoma (e.g., osteosarcoma or rhabdomyosarcoma), and leukemia or lymphoid malignancies. More particular examples of such cancers include squamous cell cancer (e.g., epithelial squamous cell cancer), adenosquamous cell carcinoma, lung cancer (e.g., including small-cell lung cancer, non-small cell lung cancer, adenocarcinoma of the lung, squamous carcinoma of the lung), cancer of the peritoneum, hepatocellular cancer, gastric or stomach cancer (e.g., including gastrointestinal cancer, pancreatic cancer), cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, primary or metastatic melanoma, multiple myeloma and B-cell lymphoma, non-Hodgkin's lymphoma, Hodgkin's lymphoma, brain (e.g., high grade glioma, diffuse pontine glioma, ependymoma, neuroblastoma, or glioblastoma), as well as head and neck cancer, and associated metastases. Additional examples of tumors can be found in The Merck Manual of Diagnosis and Therapy, 19th Edition, § on Hematology and Oncology, published by Merck Sharp & Dohme Corp., 2011 (ISBN 978-0-911910-19-3); The Merck Manual of Diagnosis and Therapy, 20th Edition, § on Hematology and Oncology, published by Merck Sharp & Dohme Corp., 2018 (ISBN 978-0-911-91042-1) (2018 digital online edition at interne website of Merck Manuals); and SEER Program Coding and Staging Manual 2016, each of which are incorporated by reference in their entirety for all purposes.

In some embodiments, the cancer being treated by methods of the present invention is a HER2 positive cancer. In some embodiments, the HER2 positive cancer is brain, breast, stomach, ovary, uterine serous endometrial carcinoma, colon, bladder, lung, uterine cervix, head and neck, sarcoma, bone tumors, or esophagus cancer.

In some embodiments, the cancer being treated by methods of the present invention is a EphA2 positive cancer. In some embodiments, the EphA2 positive cancer is breast, prostate, urinary bladder, skin, lung, ovary, sarcoma, bone tumors or brain cancer.

In some embodiments, the therapeutic method of the present disclosure includes one or more of the following steps: a) isolating immune cells (e.g., T cells or NK cells) from the subject or donor; b) modifying immune cells (e.g., T cells or NK cells) ex vivo with the polynucleotide or the recombinant vector encoding a chimeric cytokine receptor described herein; c) optionally modifying the immune cells (e.g., T cells or NK cells) ex vivo to express a chimeric antigen receptor (CAR), an antigen specific T cell receptor (TCR) and/or a bispecific antibody, said CAR, TCR or bispecific antibody specifically binds an antigen associated with said disease; d) optionally, expanding and/or activating the modified the immune cells (e.g., T cells or NK cells) before, after and/or during step b) or c); and e) introducing a therapeutically effective amount of the modified immune cells (e.g., T cells or NK cells) into the subject. In some embodiments, the immune cells express GR-CSF upon activation. In some embodiments, the immune cell is an TCR T cell, a γδ T cell, or an iNKT cell.

In some embodiments, the modified host cell is an autologous cell. In some embodiments, the modified host cell is an allogeneic cell. In cases where the host cell is isolated from a donor, the method may further include a method to prevent graft vs host disease (GVHD) and the host cell rejection.

In some embodiments, the modified host cells may also express a CD20 polypeptide as a safety switch. Accordingly, the method may further include administering an anti-CD20 antibody to the subject for removal of the isolated host cells. The anti-CD20 antibody is administered in an amount effective for sufficient removal of the isolated host cells from the subject. In some embodiments, the anti-CD20 antibody is administered in an amount effective for removal of more than 50% of the isolated host cells from the subject. For example, the anti-CD20 antibody may be administered in an amount effective for removal of more than 55%, more than 60%, more than 65%, more than 70%, more than 75%, more than 80%, more than 85%, more than 90%, more than 95%, more than 98%, more than 99%, or about 100% of the isolated host cells from the subject. The anti-CD20 antibody may be administered in an amount effective for removal of about 50% to about 70%, about 60% to about 80%, about 70% to about 90%, or about 80% to about 100% of the isolated host cells from the subject.

Non-limiting examples of anti-CD20 antibodies that can be used for removal the isolated host cells include Rituximab, Ibritumomab tiuxetan, Tositumomab, Ofatumumab, Ocrelizumab, TRU-015, Veltuzumab, AME-133v, PRO131921, and Obinutuzumab. In some embodiments, the anti-CD20 antibody is Rituximab.

In some embodiments of any of the therapeutic methods described above, the composition is administered in a therapeutically effective amount. The dosages of the composition administered in the methods of the invention will vary widely, depending upon the subject's physical parameters, the frequency of administration, the manner of administration, the clearance rate, and the like. The initial dose may be larger, and might be followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve in vivo persistence of modified host cells. It is also contemplated that a variety of doses will be effective to improve in vivo effector function of modified host cells.

In some embodiments, composition comprising the modified host cells manufactured by the methods described herein may be administered at a dosage of $10^2$ to $10^{10}$ cells/kg body weight, $10^5$ to $10^9$ cells/kg body weight, $10^5$ to $10^8$ cells/kg body weight, $10^5$ to $10^7$ cells/kg body weight, $10^7$ to $10^9$ cells/kg body weight, or $10^7$ to $10^8$ cells/kg body weight, including all integer values within those ranges. The number of modified host cells will depend on the therapeutic use for which the composition is intended for.

Modified host cells may be administered multiple times at dosages listed above. The modified host cells may be allogeneic, syngeneic, xenogeneic, or autologous to the patient undergoing therapy.

The compositions and methods described in the present disclosure may be utilized in conjunction with other types of therapy for tumors, such as chemotherapy, surgery, radiation, gene therapy, and so forth.

It is also contemplated that when used to treat various diseases/disorders, the compositions and methods of the present disclosure can be utilized with other therapeutic methods/agents suitable for the same or similar diseases/disorders. Such other therapeutic methods/agents can be co-administered (simultaneously or sequentially) to generate additive or synergistic effects. Suitable therapeutically effective dosages for each agent may be lowered due to the additive action or synergy.

In some embodiments of any of the above therapeutic methods, the method further comprises administering to the subject one or more additional compounds selected from the group consisting of immuno-suppressives, biologicals, probiotics, prebiotics, and cytokines (e.g., GM-CSF, IFN or IL-2).

In some embodiments, the method described herein further comprises providing exogenous GM-CSF, in addition to the GM-CSF produced by the immune cells, to enhance the function of immune cells expressing a chimeric cytokine receptor of the present disclosure. Exogenous GM-CSF may be provided by, for example and not limitation, i) injection of the FDA-approved GM-CSF drug Sargramostin (Leukine™) or ii) the use of nonviral or viral vectors to express GM-CSF (e.g., FDA-approved GM-CSF expressing oncolytic virus talimogene laherparepvec [TVEC, Imlygic™]). These drugs could be given before, with, or after the administration (e.g., infusion) of the immune cells expressing a chimeric cytokine receptor of the present disclosure to patients.

As a non-limiting example, the invention can be combined with other therapies that block inflammation (e.g., via blockage of IL1, INFα/β, IL6, TNF, IL23, etc.).

The methods and compositions of the invention can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 4-1BB, OX40, etc.). The methods of the invention can be also combined with other treatments that possess the ability to modulate NKT function or stability, including but not limited to CD1d, CD1d-fusion proteins, CD1d dimers or larger polymers of CD1d either unloaded or loaded with antigens, CD1d-chimeric antigen receptors (CD1d-CAR), or any other of the five known CD1 isomers existing in humans (CD1a, CD1b, CD1c, CD1e). The methods of the invention can also be combined with other treatments such as midostaurin, enasidenib, or a combination thereof.

Therapeutic methods of the invention can be combined with additional immunotherapies and therapies. For example, when used for treating tumors, the compositions of the invention can be used in combination with conventional therapies, such as, e.g., surgery, radiotherapy, chemotherapy or combinations thereof, depending on type of the tumor, patient condition, other health issues, and a variety of factors. In certain aspects, other therapeutic agents useful for combination tumor therapy with the inhibitors of the invention include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In one embodiment, the modified host cells of the invention can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

Non-limiting examples of chemotherapeutic compounds which can be used in combination treatments of the present disclosure include, for example, aminoglutethimide, amsacrine, anastrozole, asparaginase, azacitidine, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, decitabine, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, for example, following groups: anti-metabolites/anti-tumor agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In various embodiments of the methods described herein, the subject is a human. The subject may be a juvenile or an adult, of any age or sex.

In accordance with the present invention there may be numerous tools and techniques within the skill of the art, such as those commonly used in molecular biology, pharmacology, and microbiology. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al. eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Protocols in Microbiology, John Wiley and Sons, Inc.: Hoboken, NJ; Coligan et al. eds. (2005) Current Protocols in Protein Science, John Wiley and Sons, Inc.: Hoboken, NJ; and Enna et al. eds. (2005) Current Protocols in Pharmacology, John Wiley and Sons, Inc.: Hoboken, NJ.

EXAMPLES

The following examples are provided to further describe some of the embodiments disclosed herein. The examples are intended to illustrate, not to limit, the disclosed embodiments.

Example 1. Generation of Chimeric GM-CSF:IL-18 Switch Receptor (GM18)

Figures 1A, 1B:
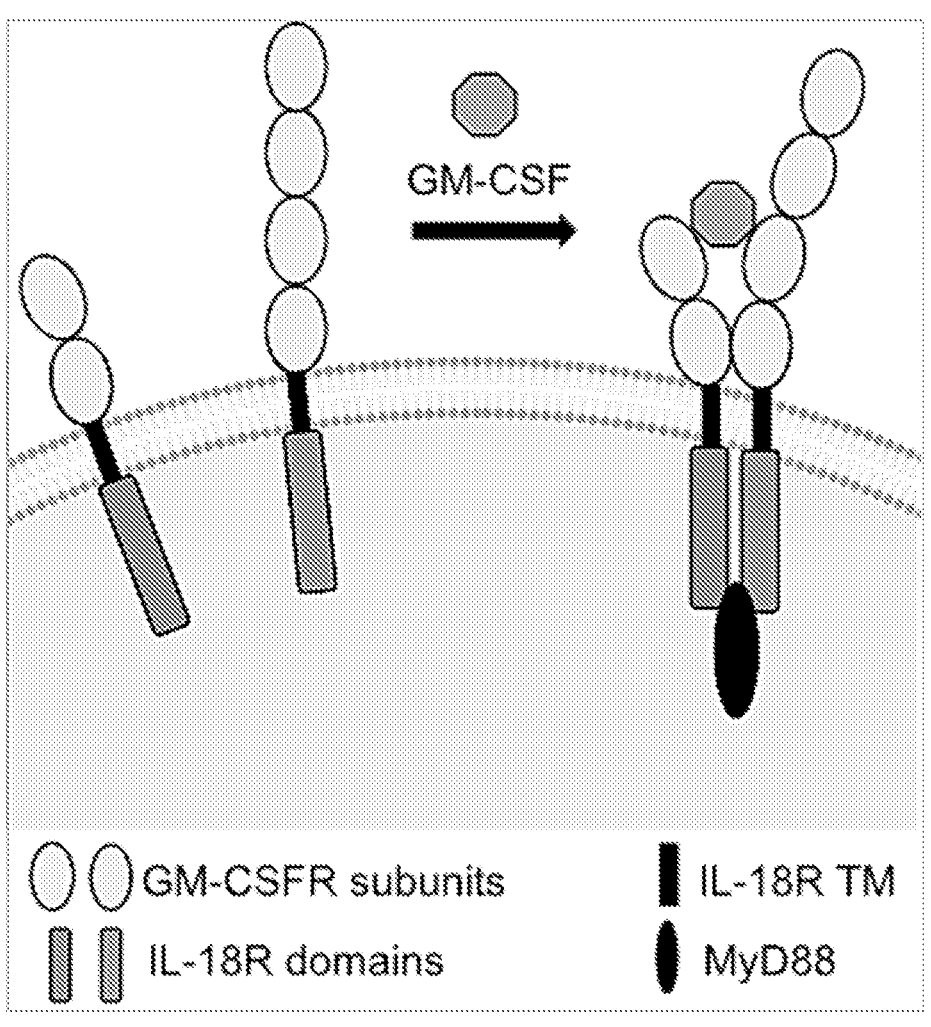
FIGS. 1A-1D demonstrate the generation of an exemplary chimeric GM-CSF:IL-18 switch receptor (GM18).
Figure 1C:
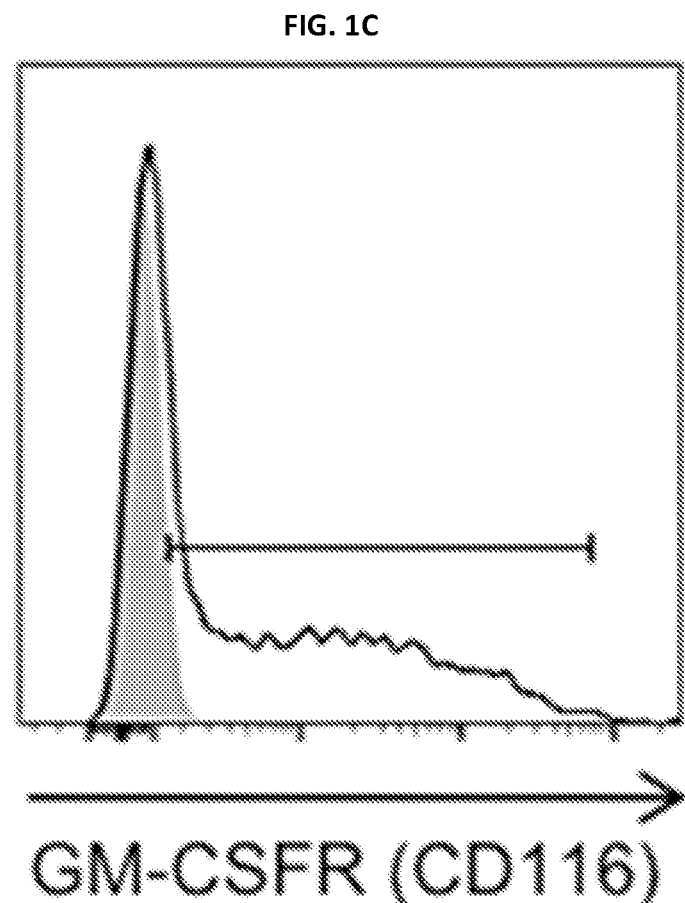
Figure 1D:
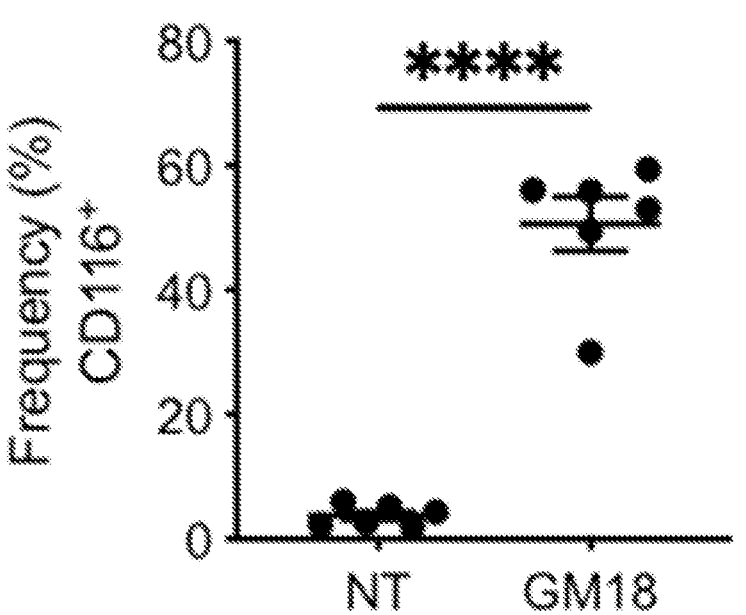

A retroviral vector was generated that contains a chimeric GM-CSF:IL-18 receptor (GM18). The design of GM18 is illustrated in FIG. 1A. Specifically, the extracellular domain of granulocyte-macrophage colony-stimulating factor receptor (GM-CSFR) α chain was fused to the transmembrane and intracellular domain of interleukin-18 receptor (IL-18R) α chain, and the extracellular domain of GM-CSFR β chain was fused to the transmembrane and intracellular domain of IL-18R β chain. Next, a retroviral vector was generated which encodes the chimeric receptor α and β subunits connected by a 2A sequence (FIG. 1B). Activated T cells were transduced, and expression of both subunits was confirmed by FACS analysis (FIGS. 1C-1D). Transduction efficiency was measured 4-7 days following transduction by FACS via detection of the GM-CSFR α chain (CD116).

Example 2. GM18-Expressing CAR T Cells Exhibit Greater Expansion, Persistence, and Glycolytic Activity In Vitro To evaluate if expression of GM18 confers an advantage to CART cells, T cells were generated which express a second generation EphA2-CAR and GM18 (4H5-GM18). A schematic of the retroviral vector encoding the EphA2-CAR is shown in FIG. 2A. The amino acid sequence and the nucleotide sequence of EphA2-CAR are set forth in SEQ ID Nos 28 and 29, respectively. Expression of EphA2-CAR and GM18 by the T cells was confirmed by FACS via detection of the GM-CSFR α chain (CD116) versus CAR detection via CD19 (FIG. 2B). An MTS assay was performed after 24 hour coculture of EphA2+ tumor cells (A673) with 4H5 versus 4H5-GM18 (black) CAR T cells, or a non-functional CAR (4H5.Δ, gray) mixed at the indicated effector to target cell (E:T) ratio shown in FIG. 2C. FIG. 2C shows the percentage of viable A673 cells in each culture condition.

Unmodified or modified CAR T cells were stimulated every 3 days with EphA2+ tumor cells (A673). While CAR-GM18 T cells continued to expand with repeat stimulations, CAR T cells did not (FIG. 2D). The experiments were performed with or without IL-15 after weekly serial coculture with A673 tumors cells at a 2:1 E:T ratio.

Cytokine Multiplex analysis was performed on supernatant from serial cocultures collected 48 hours after addition of fresh tumor cells. Levels of IFN-gamma without or with exogenous IL-15 were measured and results are presented in FIGS. 2E-2F. Levels of GM-CSF without or with exogenous IL-15 were measured and results are presented in FIGS. 2G-2H.

4H5 and 4H5-GM18 CAR T cells were analyzed by Seahorse flux analysis prior to restimulation at 12 days post transduction. Cells were subjected to the mitochondrial stress test per manufacturer instructions, and display extracellular acidification rate (ECAR, FIG. 2I) and maximal respiratory capacity (OCR, FIG. 2J).

Glucose transporter Glut-1 was measured on 4H5 and 4H5-GM18 CAR T cells by FACS analysis following 48 hours restimulation with recombinant EphA2 protein (rEphA2) or unstimulated (−). Results are presented in FIG. 2K for 4H5 (black) and 4H5-GM18 (gray) CART cells. Frequency is the percentage of live $CAR^P$ cells that express Glut-1.

Example 3. GM18-Expressing CAR T Cells Exhibit Enhanced Expansion, Persistence, and Tumor Killing In Vivo NSG mice were injected subcutaneously (s.c.) with $2 \times 10^6$ A673 tumor cells in matrigel. After 7 days, $1 \times 10^5$ EphA2-ffLuc (4H5.CD28.z) or EphA2-GM18-ffLuc CART cells (4H5.CD28.z-GM18) were injected intravenously in sterile PBS. A schematic of the experimental design is shown in FIG. 3A.

Tumor growth was tracked over time by caliper measurements. Tumor growth in the tumor only group, 4H5.CD28.z treatment group, and the 4H5.CD28.z-GM18 treatment group are shown in FIGS. 3B-3D, respectively. Bioluminescence imaging by IVIS was performed weekly to track T cell expansion. Results are presented in FIG. 3E. Survival of mice from each group is plotted in FIG. 3F. The data demonstrate that GM18-expressing CAR T cells exhibit enhanced expansion, persistence, and tumor killing in vivo.

Example 4. GM18 Expression Endows HER2-CAR T Cells with Enhanced Anti-Tumor Activity To evaluate if expression of GM18 confers an advantage to other CART cells, T cells were generated which express a second generation HER2-CAR and GM18 (FRP5-GM18). A schematic of the retroviral vector encoding the HER2-CAR is shown in FIG. 4A. The amino acid sequence and the nucleotide sequence of HER2-CAR are set forth in SEQ ID Nos 26 and 27, respectively. Expression of HER2-CAR and GM18 by the T cells was confirmed by FACS via detection of the GM-CSFR α chain (CD116) versus CAR detection via $F(ab')_2$ staining (FIG. 4B). Expansion of FRP5 and FRP5-GM18 CAR T cells was evaluated with or without IL-15 after weekly serial coculture with LM7 tumors cells at a 2:1 E:T ratio. Results are shown in FIG. 4C.

FRP5-GM18 CAR T cells were also evaluated in vivo. NSG mice were injected intraperitoneally (i.p.) with $1 \times 10^6$ LM7-ffLuc tumor cells in sterile PBS. After 7 days, $3 \times 10^5$ HER2 (FRP5.CD28.z) or HER2-GM18 CAR T cells (FRP5.CD28.z-GM18) were injected intravenously in sterile PBS. Survival of mice from each group is plotted in FIG. 4E. Tumor growth was tracked over time by bioluminescence imaging by IVIS weekly. Results for the tumor only group, FRP5.CD28.z treatment group, and FRP5.CD28.z-GM18 treatment group are presented in FIG. 4F-4H, respectively.

Example 5. Only GM18 and Not GM2 Improves the Effector Function of CAR T Cells A chimeric GM-CSF:IL-2 receptor (GM2) was designed and generated similarly as described in Example 1, the receiver scheme is shown in FIG. 5A. The functionality of GM2 was confirmed by incubating GM2-expressing T cells (GM2 T cells) or non-transduced (NT) T cells with exogenous GM-CSF at increasing concentration of GM-CSF. After 8 days, cells were counted and as shown in FIG. 5B only GM2 T cells expanded, documenting functionality of the receptor. The benefit of expressing GM2 and GM18 was then compared directly in EphA2-CAR (4H5) T cells using a serial coculture assay with A673 tumor cells as outlined in Example 2 with the only difference that T cells were restimulated every 3 instead of every 7 days. FIG. 5C demonstrates that 4H5-GM18 T cells expand to a greater extent than 4H5-GM2 and unmodified T cells, particular after the $3^{rd}$ stimulation. In addition, 4H5-GM18 T cells sustained GM-CSF production after each tumor cell stimulation in contrast to 4H5-GM2 and unmodified T cells. Results are shown in FIG. 5D. Thus, only GM18 endows CAR T cells with enhanced antitumor activity in contrast to GM2.

Example 6. Expression of Functional CAR and GM18 is Critical for the Observed Benefit In Vitro To provide further evidence that the observed benefit on expression of a functional GM18 receptor, a nonfunctional GM18 receptor (ΔGM18) was generated with no cytoplasmic signaling domains (FIG. 7A). ΔGM18 did not activate the MyD88 signaling pathway and, while it did not interfere with cytokine production of EphA2-CAR T cells, it did not enhance their ability to expand in repeat stimulation assays (FIGS. 7B-7E). Next, the question whether expression of both molecules in T-cells are required was explored using the ΔGM18 receptor and ΔCAR. CAR T-cells were mixed at a ratio of 1:1 with either CAR.GM18, CAR.ΔGM18, ΔCAR.GM18, or ΔCAR.ΔGM18 T-cells. This admixture of T-cells was then stimulated for 24 hours with recombinant protein, and cultured for 7 days prior to performing FACS analysis to determine the percentage of the respective CAR T-cell populations. While the percentage of CAR.GM18 and CAR.ΔGM18 T-cells remained stable, there was a significant decline for ΔCAR.GM18 and ΔCAR.ΔGM18 T cells, demonstrating that CAR activation is critical and bystander activation is very unlikely (FIGS. 8A, 8B). Finally, to explore if the benefit of GM18 could be extended to CARs with a 4-1BB costimulatory domain, EphA2-CAR.4-1BBz T-cells (CAR$^{BB}$ T-cells) were transduced with GM18 cells (FIG. 9A). CAR$^{BB}$.GM18 T-cells were functional as judged by cytokine production, and had a significant greater ability to expand than CAR$^{BB}$ T-cells in a repeat stimulation assay (FIGS. 9B-9D).

Example 7. Expression of Functional CAR and GM18 is Critical for Observed Benefit In Vivo Example 3 demonstrates that EphA2-CAR.GM18 CAR T-cells have potent antitumor activity in vivo. This Example confirms that the expression of a functional CAR and GM18 is critical for the observed benefit. A673-bearing mice received on day 7 one single intravenous (i.v.) dose of non-transduced T-cells, GM18 T-cells, ΔCAR T-cells, ΔCAR.GM18 T-cells, or CAR.GM18 T-cells, mice that received only tumor cells served as controls. Only CAR.GM18 T cells had significant antitumor activity resulting in a survival advantage (FIGS. 10A-10C), demonstrating that the expression of a functional CAR and GM18 is critical for the observed benefit.

Materials and Methods

The following materials and methods are used in the Examples described above.

Tumor Cell Lines

A673 (Ewing sarcoma) was purchased from the American Type Culture Collection (ATCC), and the LM7 (osteosarcoma) cell line was provided by Dr. Eugenie Kleinerman (MD Anderson Cancer Center, Houston, TX). Cell lines were authenticated by the ATCC human STR profiling cell authentication service. The generation of LM7 cells, genetically modified to express an enhanced green fluorescent protein firefly luciferase molecule (LM7.GFP.ffLuc) was previously described (Ahmed N et al., Mol Ther 2009; 17(10):1779-87). Cell lines were maintained and expanded in DMEM (GE Healthcare Life Sciences HyClone Laboratories) supplemented with 10% fetal bovine serum (FBS; GE Healthcare Life Sciences HyClone Laboratories) and 2 mM Glutamax (Invitrogen).

Generation of Retroviral Vectors

The generation of SFG retroviral vectors encoding EphA2-CAR-2A-tCD19, EphA2-ΔCAR-2A-tCD19, or HER2-CAR have previously been described (Yi Z et al. Mol Ther Methods Clin Dev 2018; 9:70-80; Ahmed N et al. Mol Ther 2009; 17(10):1779-87). The SFG retroviral vector encoding GM18 was generated by synthesizing gene fragments (Thermo Fisher Scientific) and In-Fusion cloning (Takara Bio). It consists of i) the GM-CSFRβ isoform 2 extracellular domain ending with amino acids MW, ii) the transmembrane domain and intracellular domain of the IL18-Rβ chain starting with amino acids GV (omitting the $2^{nd}$ V), iii) a T2A sequence, iv) the GM-CSFRα extracellular domain ending with amino acids DG, and v) the transmembrane domain and intracellular domain of the IL-18Rα chain starting with amino acids MI. The sequence of the final construct was verified by sequencing (Hartwell Center, St. Jude Children's Research Hospital). RD114-pseudotyped retroviral particles were generated by transient transfection of 293T-cells as previously described (Yi Z et al. Mol Ther Methods Clin Dev 2018; 9:70-80). Supernatants were collected after 48 hours, filtered, and snap frozen.

Generation of CAR and CAR.GM18 T-Cells

Human peripheral blood mononuclear cells (PBMCs) were obtained from whole blood of healthy donors under an IRB approved protocol at St. Jude Children's Research Hospital, after informed consent was obtained in accordance with the Declaration of Helsinki or from de-identified donor pheresis products of St. Jude Blood Donor Center. Retroviral transduced T-cells were generated as previously described (Yi et al., Mol Ther Methods Clin Dev 2018; 9:70-80). Briefly, PBMCs were stimulated on anti-CD3 and anti-CD28 coated plates for 48 hours. Recombinant human IL-7 (10 ng/mL, Peprotech) and IL-15 (5 ng/mL, Peprotech) were added 24 hours after initial stimulation and were maintained in culture until functional studies were performed. Cells were then seeded onto retronectin-coated (Clontech) plates with retroviral particles for 2-4 days for transduction. Non-transduced cells (NT) were prepared similarly except no retrovirus was included in the retronectin wells. CAR.GM18 and CAR.ΔGM18 cells were co-transduced with both retroviral particles in the same well. For generation of EphA2-CAR-GFP.ffLuc and EphA2-CAR.GM18-GFP.ffLuc T-cells, activated T-cells were first transduced with CAR or CAR+GM18 for 24 hours, and then transferred to GFP.ffLuc retrovirus-containing retronectin-coated plate for 3-4 days. T-cells were then expanded and sorted for functional analysis for 7-10 days post-transduction. All T-cells were cultured with RPMI-1640 supplemented with 10% FBS and 2 mM Glutamax (complete RPMI).

Repeat Stimulation Assay $1\times10^6$ (or $5\times10^5$) T-cells were cocultured in complete RPMI with $5\times10^5$ (or $1\times10^5$) tumor cells in a 24-well or 48-well tissue culture-treated plate, respectively. IL-15 (5 ng/ml) was added to HER2-CAR T-cell experiments. Cells were fed with fresh complete RPMI at 48 and 120 hours after coculture. After 7 days, T-cells were harvested, counted, and replated at the same ratio with fresh tumor cells as long as they had killed tumor cells by microscopic inspection.

Xenograft Mouse Models

All animal experiments were approved by St. Jude Children's Research Hospital Institutional Animal Care and Use Committee. Xenograft experiments were performed with 7-10 week old NOD-scid IL2Rgamma$^{null}$ (NSG) mice obtained from St. Jude Children's Research Hospital NSG colony. A673 Ewing sarcoma model: Mice received s.c. injection of $2\times10^6$ A673 cells in Matrigel (Corning) in the right flank. On day 7, mice received a single i.v. dose of $1\times10^5$ or $3\times10^5$ EphA2-CAR or EphA2-CAR.GM18 T-cells via tail vein injection. Tumor growth was measured by weekly caliper measurements. Mice were euthanized when they met physical euthanasia criteria (significant weight loss, signs of distress), when the tumor burden reached 20% of total body mass ($\geq4000$ mm$^3$), or when recommended by veterinary staff. For rechallenge experiments, mice received an additional s.c. injection of $2\times10^6$ A673 cells in the left flank between days 102 to 104 after initial tumor cell injection. LM7 osteosarcoma model: Mice were injected i.p. with $1\times10^6$ LM7.GFP.ffLuc cells, and on day 7 received a single i.v. dose of $1\times10^5$ or $3\times10^5$ HER2-CAR or HER2-CAR.GM18 T-cells via tail vein injection. Mice were euthanized when they reached our bioluminescence flux endpoint of $1\times10^{10}$ for 2 consecutive weeks, and/or the above-mentioned general euthanasia criteria.

Statistical Analysis

For all experiments, the number of biological replicates and statistical analysis used are described in the figure description. For comparison between two groups, a two-tailed t-test was used. For comparisons of three or more groups, values were log transformed as needed and analyzed by ANOVA with Dunnett's or Tukey's post-test. Survival was assessed by the log-rank test with Bonferroni adjustment for multiple comparisons. Bioluminescence imaging data were analyzed using either ANOVA or area under the curve (AUC). Statistical analyses were conducted with Prism software (GraphPad Software, San Diego, CA).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

---

The invention claimed is:

1. A polynucleotide encoding a chimeric cytokine receptor, said chimeric cytokine receptor comprising two polypeptides, each comprising an extracellular domain of granulocyte-macrophage colony-stimulating factor (GM-CSF) receptor, or a functional portion thereof, a transmembrane domain, and an intracellular domain of interleukin-18 receptor (IL-18) receptor, or a functional portion thereof, wherein the chimeric cytokine receptor improves effector function when expressed in an immune cell expressing a chimeric antigen receptor (CAR), an antigen specific T cell receptor (TCR) and/or a bispecific antibody, relative to an immune cell not expressing the chimeric cytokine receptor.

2. The polynucleotide of claim 1, wherein the chimeric cytokine receptor comprises (i) a first polypeptide comprising an extracellular region of GM-CSF receptor α chain, or a functional portion thereof, a first transmembrane region, and an intracellular region of IL-18 receptor α chain, or a functional portion thereof; and (ii) a second polypeptide comprising an extracellular region of GM-CSF receptor β chain, or a functional portion thereof, a second transmembrane region, and an intracellular region of IL-18 receptor β chain, or a functional portion thereof.

3. The polynucleotide of claim 2, wherein the extracellular region of GM-CSF receptor α chain comprises the amino acid sequence of SEQ ID NO: 1, or an amino acid sequence having at least 80% sequence identity thereof; or the sequence encoding the extracellular region of GM-CSF receptor α chain comprises the nucleotide sequence of SEQ ID NO: 2, or a nucleotide sequence having at least 80% sequence identity thereof.

4. The polynucleotide of claim 2, wherein the intracellular region of IL-18 receptor α chain comprises the amino acid sequence of SEQ ID NO: 5, or an amino acid sequence having at least 80% sequence identity thereof, or the sequence encoding the intracellular region of IL-18 receptor α chain comprises the nucleotide sequence of SEQ ID NO: 6, or a nucleotide sequence having at least 80% sequence identity thereof.

5. The polynucleotide of claim 2, wherein the extracellular region of GM-CSF receptor β chain comprises the amino acid sequence of SEQ ID NO: 7, or an amino acid sequence having at least 80% sequence identity thereof; or the sequence encoding the extracellular region of GM-CSF receptor β chain comprises the nucleotide sequence of SEQ ID NO: 8, or a nucleotide sequence having at least 80% sequence identity thereof.

6. The polynucleotide of claim 2, wherein the intracellular region of IL-18 receptor β chain comprises the amino acid sequence of SEQ ID NO: 11, or an amino acid sequence having at least 80% sequence identity thereof; or the sequence encoding the intracellular region of IL-18 receptor β chain comprises the nucleotide sequence of SEQ ID NO: 12, or a nucleotide sequence having at least 80% sequence identity thereof.

7. The polynucleotide of claim 2, wherein at least one of the transmembrane regions is derived from a transmembrane domain of IL-18 receptor or GM-CSF receptor.

8. The polynucleotide of claim 2, wherein the first transmembrane region comprises a transmembrane region of IL-18 receptor α chain.

9. The polynucleotide of claim 8, wherein the transmembrane region of IL-18 receptor α chain comprises the amino acid sequence of SEQ ID NO: 3, or an amino acid sequence having at least 80% sequence identity thereof; or the sequence encoding the transmembrane region of IL-18 receptor α chain comprises the nucleotide sequence of SEQ ID NO: 4, or a nucleotide sequence having at least 80% sequence identity thereof.

10. The polynucleotide of claim 2, wherein the second transmembrane region comprises a transmembrane region of IL-18 receptor β chain.

11. The polynucleotide of claim 10, wherein the transmembrane region of IL-18 receptor β chain comprises the amino acid sequence of SEQ ID NO: 9, or an amino acid sequence having at least 80% sequence identity thereof, or the sequence encoding the transmembrane region of IL-18 receptor β chain comprises the nucleotide sequence of SEQ ID NO: 10, or a nucleotide sequence having at least 80% sequence identity thereof.

12. The polynucleotide of claim 2, wherein the first polypeptide further comprises a first leader sequence and/or the second polypeptide further comprises a second leader sequence.

13. The polynucleotide of claim 12, wherein the first leader sequence is derived from a leader sequence of GM-CSF receptor α chain.

14. The polynucleotide of claim 12, wherein the first leader sequence comprises the amino acid sequence of SEQ ID NO: 13, SEQ ID NO: 44, or SEQ ID NO: 46, or an amino acid sequence having at least 80% sequence identity to SEQ ID NO: 13, SEQ ID NO: 44, or SEQ ID NO: 46; or the sequence encoding the first leader sequence comprises the nucleotide sequence of SEQ ID NO: 14, SEQ ID NO: 45, or SEQ ID NO: 47, or a nucleotide sequence having at least 80% sequence identity to SEQ ID NO: 14, SEQ ID NO: 45, or SEQ ID NO: 47.

15. The polynucleotide of claim 12, wherein the second leader sequence is derived from a leader sequence of GM-CSF receptor β chain.

16. The polynucleotide of claim 15, wherein the second leader sequence comprises the amino acid sequence of SEQ ID NO: 15, SEQ ID NO: 44, or SEQ ID NO: 46, or an amino acid sequence having at least 80% sequence identity to SEQ ID NO: 15, SEQ ID NO: 44, or SEQ ID NO: 46; or the nucleotide encoding the second leader sequence comprises the nucleotide sequence of SEQ ID NO: 16, SEQ ID NO: 45, or SEQ ID NO: 47, or a nucleotide sequence having at least 80% sequence identity to SEQ ID NO: 16, SEQ ID NO: 45, or SEQ ID NO: 47.

17. The polynucleotide of claim 2, wherein the first polypeptide comprises the amino acid sequence of SEQ ID NO: 17, or an amino acid sequence having at least 80% sequence identity thereof; or the sequence encoding the first polypeptide comprises the nucleotide sequence of SEQ ID NO: 18, or a nucleotide sequence having at least 80% sequence identity thereof.

18. The polynucleotide of claim 2, wherein the second polypeptide comprises the amino acid sequence of SEQ ID NO: 19, or an amino acid sequence having at least 80% sequence identity thereof; or the sequence encoding the second polypeptide comprises the nucleotide sequence of SEQ ID NO: 20, or a nucleotide sequence having at least 80% sequence identity thereof.

19. The polynucleotide of claim 2, wherein the sequence encoding the first polypeptide is operably linked to the sequence encoding a second polypeptide via a sequence encoding a self-cleaving peptide or an internal ribosomal entry site (IRES).

20. The polynucleotide of claim 19, wherein the self-cleaving peptide comprises the amino acid sequence of SEQ ID NO: 21, or an amino acid sequence having at least 80% sequence identity thereof; or the sequence encoding the self-cleaving peptide comprises the nucleotide sequence of SEQ ID NO: 22, or a nucleotide sequence having at least 80% sequence identity thereof.

21. The polynucleotide of claim 1, wherein the chimeric cytokine receptor comprises the amino acid sequence of SEQ ID NO: 23, or an amino acid sequence having at least 80% sequence identity thereof; or the polynucleotide comprises the nucleotide sequence of SEQ ID NO: 24, or a nucleotide sequence having at least 80% sequence identity thereof.

22. A recombinant vector comprising the polynucleotide of claim 1.

23. A chimeric cytokine receptor encoded by the polynucleotide of claim 1.

24. A chimeric cytokine receptor, comprising two polypeptides, each comprising an extracellular domain of granulocyte-macrophage colony-stimulating factor (GM-CSF) receptor, or a functional portion thereof, a transmembrane domain, and an intracellular domain of interleukin-18 receptor (IL-18) receptor, or a functional portion thereof, wherein the chimeric cytokine receptor improves effector function when expressed in an immune cell expressing a chimeric antigen receptor (CAR), an antigen specific T cell receptor (TCR) and/or bispecific antibody, relative to an immune cell not expressing the chimeric cytokine receptor.

25. An isolated host cell comprising the polynucleotide of claim 1.

26. A pharmaceutical composition comprising the host cell of claim 25 and a pharmaceutically acceptable carrier and/or excipient.

27. The polynucleotide of claim 1, wherein the immune cell is a T cell or NK cell.

28. The polynucleotide of claim 1, wherein the chimeric cytokine receptor comprises
(i) a first polypeptide comprising an extracellular region of GM-CSF receptor α chain, or a functional portion thereof, a first transmembrane region, and an intracellular region of IL-18 receptor β chain, or a functional portion thereof; and (ii) a second polypeptide comprising an extracellular region of GM-CSF receptor β chain, or a functional portion thereof, a second transmembrane region, and an intracellular region of IL-18 receptor α chain, or a functional portion thereof.

29. The polynucleotide of claim 28, wherein the extracellular region of GM-CSF receptor α chain comprises the amino acid sequence of SEQ ID NO: 1, or an amino acid sequence having at least 80% sequence identity thereof; or the sequence encoding the extracellular region of GM-CSF receptor α chain comprises the nucleotide sequence of SEQ ID NO: 2, or a nucleotide sequence having at least 80% sequence identity thereof.

30. The polynucleotide of claim 28, wherein the intracellular region of IL-18 receptor α chain comprises the amino acid sequence of SEQ ID NO: 5, or an amino acid sequence having at least 80% sequence identity thereof; or the sequence encoding the intracellular region of IL-18 receptor α chain comprises the nucleotide sequence of SEQ ID NO: 6, or a nucleotide sequence having at least 80% sequence identity thereof.

31. The polynucleotide of claim 28, wherein the extracellular region of GM-CSF receptor β chain comprises the amino acid sequence of SEQ ID NO: 7, or an amino acid sequence having at least 80% sequence identity thereof; or the sequence encoding the extracellular region of GM-CSF receptor β chain comprises the nucleotide sequence of SEQ ID NO: 8, or a nucleotide sequence having at least 80% sequence identity thereof.

32. The polynucleotide of claim 28, wherein the intracellular region of IL-18 receptor β chain comprises the amino acid sequence of SEQ ID NO: 11, or an amino acid sequence having at least 80% sequence identity thereof; or the sequence encoding the intracellular region of IL-18 receptor β chain comprises the nucleotide sequence of SEQ ID NO: 12, or a nucleotide sequence having at least 80% sequence identity thereof.

33. The polynucleotide of claim 28, wherein at least one of the transmembrane regions is derived from a transmembrane domain of IL-18 receptor or GM-CSF receptor.

34. The polynucleotide of claim 28, wherein the first transmembrane region comprises a transmembrane region of IL-18 receptor α chain.

35. The polynucleotide of claim 34, wherein the transmembrane region of IL-18 receptor α chain comprises the amino acid sequence of SEQ ID NO: 3, or an amino acid sequence having at least 80% sequence identity thereof; or the sequence encoding the transmembrane region of IL-18 receptor α chain comprises the nucleotide sequence of SEQ ID NO: 4, or a nucleotide sequence having at least 80% sequence identity thereof.

36. The polynucleotide of claim 28, wherein the second transmembrane region comprises a transmembrane region of IL-18 receptor β chain.

37. The polynucleotide of claim 36, wherein the transmembrane region of IL-18 receptor β chain comprises the amino acid sequence of SEQ ID NO: 9, or an amino acid sequence having at least 80% sequence identity thereof; or the sequence encoding the transmembrane region of IL-18 receptor β chain comprises the nucleotide sequence of SEQ ID NO: 10, or a nucleotide sequence having at least 80% sequence identity thereof.

38. The polynucleotide of claim 28, wherein the first polypeptide further comprises a first leader sequence and/or the second polypeptide further comprises a second leader sequence.

39. The polynucleotide of claim 38, wherein the first leader sequence is derived from a leader sequence of GM-CSF receptor α chain.

40. The polynucleotide of claim 38, wherein the first leader sequence comprises the amino acid sequence of SEQ ID NO: 13, SEQ ID NO: 44, or SEQ ID NO: 46, or an amino acid sequence having at least 80% sequence identity to SEQ ID NO: 13, SEQ ID NO: 44, or SEQ ID NO: 46; or the sequence encoding the first leader sequence comprises the nucleotide sequence of SEQ ID NO: 14, SEQ ID NO: 45, or SEQ ID NO: 47, or a nucleotide sequence having at least 80% sequence identity to SEQ ID NO: 14, SEQ ID NO: 45, or SEQ ID NO: 47.

41. The polynucleotide of claim 38, wherein the second leader sequence is derived from a leader sequence of GM-CSF receptor β chain.

42. The polynucleotide of claim 41, wherein the second leader sequence comprises the amino acid sequence of SEQ ID NO: 15, SEQ ID NO: 44, or SEQ ID NO: 46, or an amino acid sequence having at least 80% sequence identity to SEQ ID NO: 15, SEQ ID NO: 44, or SEQ ID NO: 46; or the nucleotide encoding the second leader sequence comprises the nucleotide sequence of SEQ ID NO: 16, SEQ ID NO: 45, or SEQ ID NO: 47, or a nucleotide sequence having at least 80% sequence identity to SEQ ID NO: 16, SEQ ID NO: 45, or SEQ ID NO: 47.

43. The polynucleotide of claim 28, wherein the sequence encoding the first polypeptide is operably linked to the sequence encoding a second polypeptide via a sequence encoding a self-cleaving peptide or an internal ribosomal entry site (IRES).

44. The polynucleotide of claim 43, wherein the self-cleaving peptide comprises the amino acid sequence of SEQ ID NO: 21, or an amino acid sequence having at least 80% sequence identity thereof; or the sequence encoding the self-cleaving peptide comprises the nucleotide sequence of SEQ ID NO: 22, or a nucleotide sequence having at least 80% sequence identity thereof.

\* \* \* \* \*

SEQUENCE LISTING

```
<160> NUMBER OF SEQ ID NOS: 62

<210> SEQ ID NO 1
<211> LENGTH: 298
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Lys Ser Asp Leu Arg Thr Val Ala Pro Ala Ser Ser Leu Asn Val
1               5                   10                  15

Arg Phe Asp Ser Arg Thr Met Asn Leu Ser Trp Asp Cys Gln Glu Asn
            20                  25                  30

Thr Thr Phe Ser Lys Cys Phe Leu Thr Asp Lys Lys Asn Arg Val Val
        35                  40                  45

Glu Pro Arg Leu Ser Asn Asn Glu Cys Ser Cys Thr Phe Arg Glu Ile
    50                  55                  60

Cys Leu His Glu Gly Val Thr Phe Glu Val His Val Asn Thr Ser Gln
65                  70                  75                  80

Arg Gly Phe Gln Gln Lys Leu Leu Tyr Pro Asn Ser Gly Arg Glu Gly
                85                  90                  95

Thr Ala Ala Gln Asn Phe Ser Cys Phe Ile Tyr Asn Ala Asp Leu Met
                100                 105                 110

Asn Cys Thr Trp Ala Arg Gly Pro Thr Ala Pro Arg Asp Val Gln Tyr
            115                 120                 125

Phe Leu Tyr Ile Arg Asn Ser Lys Arg Arg Arg Glu Ile Arg Cys Pro
    130                 135                 140

Tyr Tyr Ile Gln Asp Ser Gly Thr His Val Gly Cys His Leu Asp Asn
```

-continued

```
145              150              155              160

Leu Ser Gly Leu Thr Ser Arg Asn Tyr Phe Leu Val Asn Gly Thr Ser
            165              170              175

Arg Glu Ile Gly Ile Gln Phe Phe Asp Ser Leu Leu Asp Thr Lys Lys
        180              185              190

Ile Glu Arg Phe Asn Pro Pro Ser Asn Val Thr Val Arg Cys Asn Thr
        195              200              205

Thr His Cys Leu Val Arg Trp Lys Gln Pro Arg Thr Tyr Gln Lys Leu
    210              215              220

Ser Tyr Leu Asp Phe Gln Tyr Gln Leu Asp Val His Arg Lys Asn Thr
225              230              235              240

Gln Pro Gly Thr Glu Asn Leu Leu Ile Asn Val Ser Gly Asp Leu Glu
            245              250              255

Asn Arg Tyr Asn Phe Pro Ser Ser Glu Pro Arg Ala Lys His Ser Val
            260              265              270

Lys Ile Arg Ala Ala Asp Val Arg Ile Leu Asn Trp Ser Ser Trp Ser
        275              280              285

Glu Ala Ile Glu Phe Gly Ser Asp Asp Gly
    290              295
```

```
<210> SEQ ID NO 2
<211> LENGTH: 894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gagaagtccg acctgagaac agtggcccct gccagctctc tgaacgttcg cttcgacagc      60
cggaccatga acctgagctg ggactgccaa gagaacacaa ccttcagcaa gtgcttcctg     120
accgacaaga agaaccgggt cgtcgagccc agactgagca acaatgagtg ctcctgcacc     180
ttcagagaga tctgcctgca cgagggcgtg acctttgagg tgcacgtgaa cacaagccag     240
cggggctttc agcagaagct gctgtacccc aatagcggca gagagggaac cgccgctcag     300
aacttcagct gcttcatcta caacgccgac ctcatgaact gcacctgggc cagaggacct     360
accgctccta gagatgtgca gtacttcctg tacattcgga acagcaagcg gcggagagaa     420
atcaggtgcc cctactacat ccaagacagc ggcacacacg tgggctgcca cctggataat     480
ctgtctggcc tgaccagccg gaactacttc ctggtcaatg gcaccagccg cgagatcggc     540
atccagttct ttgacagcct gctggacacc aagaagatcg agcggttcaa ccctcctagc     600
aacgtgaccg tgcggtgcaa caccacacat tgtctcgtgc ggtggaagca gccccggaca     660
taccagaagc tgagctacct ggacttccag taccagctgg atgtgcaccg gaagaacacc     720
cagcctggca ccgagaacct gctgatcaat gtgtccggcg acctggaaaa ccggtacaac     780
ttccctagca gcgagcccag ggccaagcac agcgtgaaaa ttagagccgc cgatgtgcgc     840
atcctgaact ggtcctcttg gagcgaggcc atcgagtttg gatccgacga cggc          894
```

```
<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 3

Met Ile Ile Ala Val Leu Ile Leu Val Ala Val Val Cys Leu Val Thr
1               5                   10                  15

Val Cys Val Ile
            20

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atgatcattg ccgtgctgat cctggtggcc gtcgtgtgtc tggtcaccgt gtgcgtgatc         60

<210> SEQ ID NO 5
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Tyr Arg Val Asp Leu Val Leu Phe Tyr Arg His Leu Thr Arg Arg Asp
1               5                   10                  15

Glu Thr Leu Thr Asp Gly Lys Thr Tyr Asp Ala Phe Val Ser Tyr Leu
            20                  25                  30

Lys Glu Cys Arg Pro Glu Asn Gly Glu Glu His Thr Phe Ala Val Glu
        35                  40                  45

Ile Leu Pro Arg Val Leu Glu Lys His Phe Gly Tyr Lys Leu Cys Ile
    50                  55                  60

Phe Glu Arg Asp Val Val Pro Gly Gly Ala Val Val Asp Glu Ile His
65                  70                  75                  80

Ser Leu Ile Glu Lys Ser Arg Arg Leu Ile Ile Val Leu Ser Lys Ser
                85                  90                  95

Tyr Met Ser Asn Glu Val Arg Tyr Glu Leu Glu Ser Gly Leu His Glu
            100                 105                 110

Ala Leu Val Glu Arg Lys Ile Lys Ile Ile Leu Ile Glu Phe Thr Pro
        115                 120                 125

Val Thr Asp Phe Thr Phe Leu Pro Gln Ser Leu Lys Leu Leu Lys Ser
    130                 135                 140

His Arg Val Leu Lys Trp Lys Ala Asp Lys Ser Leu Ser Tyr Asn Ser
145                 150                 155                 160

Arg Phe Trp Lys Asn Leu Leu Tyr Leu Met Pro Ala Lys Thr Val Lys
                165                 170                 175

Pro Gly Arg Asp Glu Pro Glu Val Leu Pro Val Leu Ser Glu Ser
            180                 185                 190

<210> SEQ ID NO 6
<211> LENGTH: 576
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
```

-continued

```
tacagagtgg acctggtgct gttctaccgg cacctgacca gaagggacga gacactgacc      60
gacggcaaga cctacgatgc cttcgtgtcc tacctgaaag agtgcagacc cgagaacggc     120
gaggaacaca ccttcgccgt ggaaatcctg cctagagtgc tggaaaagca cttcggctac     180
aagctgtgca tcttcgagag ggacgttgtg cctggcggag ctgtggtgga tgagatccac     240
agcctgatcg agaagtccag acggctgatc atcgtgctga gcaagagcta catgagcaac     300
gaagtccgct acgagctgga aagcggactg cacgaagccc tggtggaacg gaagatcaag     360
atcatcctga ttgagttcac ccctgtgacc gacttcacat tcctgcctca gagcctgaag     420
ctgctgaagt cccacagagt gctgaagtgg aaggccgaca gagcctgag ctacaacagc      480 cggttctgga agaacctgct gtacctgatg cctgccaaga ccgtgaagcc cggcagagat     540
gaacctgagg tgctgcctgt gctgagcgag tcttaa                              576
```

<210> SEQ ID NO 7
<211> LENGTH: 433
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Trp Glu Arg Ser Leu Ala Gly Ala Glu Glu Thr Ile Pro Leu Gln Thr
1               5                   10                  15

Leu Arg Cys Tyr Asn Asp Tyr Thr Ser His Ile Thr Cys Arg Trp Ala
                20                  25                  30

Asp Thr Gln Asp Ala Gln Arg Leu Val Asn Val Thr Leu Ile Arg Arg
            35                  40                  45

Val Asn Glu Asp Leu Leu Glu Pro Val Ser Cys Asp Leu Ser Asp Asp
        50                  55                  60

Met Pro Trp Ser Ala Cys Pro His Pro Arg Cys Val Pro Arg Arg Cys
65                  70                  75                  80

Val Ile Pro Cys Gln Ser Phe Val Val Thr Asp Val Asp Tyr Phe Ser
                85                  90                  95

Phe Gln Pro Asp Arg Pro Leu Gly Thr Arg Leu Thr Val Thr Leu Thr
                100                 105                 110

Gln His Val Gln Pro Pro Glu Pro Arg Asp Leu Gln Ile Ser Thr Asp
            115                 120                 125

Gln Asp His Phe Leu Leu Thr Trp Ser Val Ala Leu Gly Ser Pro Gln
        130                 135                 140

Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
                180                 185                 190

Val Ala Arg Val Arg Thr Arg Leu Ala Pro Gly Ser Arg Leu Ser Gly
            195                 200                 205

Arg Pro Ser Lys Trp Ser Pro Glu Val Cys Trp Asp Ser Gln Pro Gly
        210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255
```

-continued

```
Ser Phe Gly Leu Phe Tyr Lys Pro Ser Pro Asp Ala Gly Ser Ala Val
            260             265             270

Leu Leu Arg Glu Glu Glu Cys Ser Pro Val Leu Arg Glu Gly Leu Gly
            275             280             285

Ser Leu His Thr Arg His His Cys Gln Ile Pro Val Pro Asp Pro Ala
            290             295             300

Thr His Gly Gln Tyr Ile Val Ser Val Gln Pro Arg Arg Ala Glu Lys
305             310             315             320

His Ile Lys Ser Ser Val Asn Ile Gln Met Ala Pro Pro Ser Leu Asn
            325             330             335

Val Thr Lys Asp Gly Asp Ser Tyr Ser Leu Arg Trp Glu Thr Met Lys
            340             345             350

Met Arg Tyr Glu His Ile Asp His Thr Phe Glu Ile Gln Tyr Arg Lys
            355             360             365

Asp Thr Ala Thr Trp Lys Asp Ser Lys Thr Glu Thr Leu Gln Asn Ala
            370             375             380

His Ser Met Ala Leu Pro Ala Leu Glu Pro Ser Thr Arg Tyr Trp Ala
385             390             395             400

Arg Val Arg Val Arg Thr Ser Arg Thr Gly Tyr Asn Gly Ile Trp Ser
            405             410             415

Glu Trp Ser Glu Ala Arg Ser Trp Asp Thr Glu Ser Val Leu Pro Met
            420             425             430

Trp
```

<210> SEQ ID NO 8
<211> LENGTH: 1299
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 8

```
tgggagagaa gtctggctgg cgccgaggaa acaatccctc tgcagaccct gcggtgctac      60
aacgactaca ccagccacat cacctgtaga tgggccgaca cacaggacgc ccagagactg     120
gtcaatgtga ccctgatcag aagagtgaac gaggacctgc tggaacccgt gtcctgtgac     180
ctgagcgacg atatgccttg gagcgcctgt cctcatccta gatgtgtgcc tcggagatgc     240
gtgatcccct gccagagctt tgtggtcacc gatgtggact acttcagctt ccagcctgac     300
agacccctgg gcaccagact gacagtgaca ctgacacagc acgtgcagcc tccagagcct     360
agggacctgc agatctctac cgaccaggac cacttcctgc tgacttggag tgtggccctg     420
ggaagccctc agtctcattg gcttagccct ggcgacctgg aattcgaggt ggtgtacaag     480
agactgcagg acagctggga agatgccgcc atcctgctga gcaataccag ccaggctaca     540 ctgggcccg aacacctgat gcctagctct acctatgtgg ccagagtgcg gacaagactg     600
gcccctggat ctagactgag cggcagacct tctaagtggt cccctgaagt ctgctgggat     660
agccagcctg gggatgaagc ccagcctcag aacctggaat gcttcttcga tggcgccgct     720
gtgctgagct gttcttggga agtgcggaaa gaggtggcca gcagcgttag cttcggcctg     780
ttctacaagc cctctccaga tgccggatct gccgtgctgc tgagagaaga ggaatgcagc     840
cccgtgctca gagaaggcct gggatctctg cacaccagac accactgtca gatccccgtg     900
cctgatcctg ccacacacgg ccagtatatc gtgtccgtgc agccaagaag ggccgagaag     960
cacatcaaga gcagcgtgaa catccagatg gcccctccaa gcctgaacgt gaccaaggac    1020
```

-continued

```
ggcgacagct acagcctgag atgggagaca atgaagatgc gctacgagca catcgaccac      1080
accttcgaga tccagtaccg gaaggatacc gccacctgga aggacagcaa gaccgagaca      1140
ctgcagaacg cccactctat ggcactgcca gctctcgagc cctccaccag atattgggcc      1200
agagtcagag tgcggaccag cagaacaggc tacaacggca tttggagcga gtggagcgaa      1260
gccagaagct gggatacaga gtctgtacta ccaatgtgg                             1299
```

```
<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Val Leu Leu Tyr Ile Leu Leu Gly Thr Ile Gly Thr Leu Val Ala
1               5                   10                  15

Val Leu Ala Ala
            20
```

```
<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggcgtgctgc tgtacatcct gctgggcaca atcggaacac tggtggctgt gctggctgcc      60
```

```
<210> SEQ ID NO 11
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Ala Leu Leu Tyr Arg His Trp Ile Glu Ile Val Leu Leu Tyr Arg
1               5                   10                  15

Thr Tyr Gln Ser Lys Asp Gln Thr Leu Gly Asp Lys Lys Asp Phe Asp
                20                  25                  30

Ala Phe Val Ser Tyr Ala Lys Trp Ser Ser Phe Pro Ser Glu Ala Thr
            35                  40                  45

Ser Ser Leu Ser Glu Glu His Leu Ala Leu Ser Leu Phe Pro Asp Val
        50                  55                  60

Leu Glu Asn Lys Tyr Gly Tyr Ser Leu Cys Leu Leu Glu Arg Asp Val
65                  70                  75                  80

Ala Pro Gly Gly Val Tyr Ala Glu Asp Ile Val Ser Ile Ile Lys Arg
                85                  90                  95

Ser Arg Arg Gly Ile Phe Ile Leu Ser Pro Asn Tyr Val Asn Gly Pro
                100                 105                 110

Ser Ile Phe Glu Leu Gln Ala Ala Val Asn Leu Ala Leu Asp Asp Gln
            115                 120                 125

Thr Leu Lys Leu Ile Leu Ile Lys Phe Cys Tyr Phe Gln Glu Pro Glu
        130                 135                 140
```

```
Ser Leu Pro His Leu Val Lys Lys Ala Leu Arg Val Leu Pro Thr Val
145                 150                 155                 160

Thr Trp Arg Gly Leu Lys Ser Val Pro Pro Asn Ser Arg Phe Trp Ala
                165                 170                 175

Lys Met Arg Tyr His Met Pro Val Lys Asn Ser Gln Gly Phe Thr Trp
            180                 185                 190

Asn Gln Leu Arg Ile Thr Ser Arg Ile Phe Gln Trp Lys Gly Leu Ser
        195                 200                 205

Arg Thr Glu Thr Thr Gly Arg Ser Ser Gln Pro Lys Glu Trp
    210                 215                 220
```

```
<210> SEQ ID NO 12
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
agcgctctgc tgtatagaca ctggatcgag atcgtcctgc tgtaccggac ctaccagagc      60
aaggatcaga ccctgggcga caagaaggac ttcgacgcct ttgtgtccta cgccaagtgg     120
tccagctttc ccagcgaggc cacaagcagc ctgagcgaag aacatctggc cctgtctctg     180
ttccccgatg tgctggaaaa caaatacggc tacagcctgt gcctgctgga aagagatgtt     240
gcccctggcg gagtgtacgc cgaggatatc gtgtccatca tcaagcggag cagacggggc     300
atcttcattc tgagccccaa ctacgtgaac ggccccagca tctttgaact gcaagccgcc     360
gtgaacctgg ctctggacga tcagacactg aagctgatcc tgatcaagtt ctgctacttc     420
caagagcctg agagcctgcc tcacctggtc aagaaagccc tgagagtgct gcctaccgtg     480
acttggagag gcctgaagtc cgtgcctcct aacagcagat tctgggccaa gatgagatac     540
cacatgcctg tgaagaacag ccagggcttc acctggaacc agctgcggat cacctccaga     600
atcttccagt ggaagggcct gagccggacc gagacaacag gcagaagcag ccagcctaaa     660
gagtgg                                                                666
```

```
<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Met Leu Leu Leu Val Thr Ser Leu Leu Leu Cys Glu Leu Pro His Pro
1               5                   10                  15

Ala Phe Leu Leu Ile Pro
            20
```

```
<210> SEQ ID NO 14
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atgctgctgc tggtcacatc tctgctgctg tgcgagctgc cccatcctgc ctttctgctg      60
```

-continued atcccc                                                                          66

```
<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Val Leu Ala Gln Gly Leu Leu Ser Met Ala Leu Leu Ala Leu Cys
1               5                   10                  15

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atggttctgg cccagggcct gctgtctatg gctctgcttg ctctgtgc                     48

<210> SEQ ID NO 17
<211> LENGTH: 531
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Leu Leu Leu Val Thr Ser Leu Leu Leu Cys Glu Leu Pro His Pro
1               5                   10                  15

Ala Phe Leu Leu Ile Pro Glu Lys Ser Asp Leu Arg Thr Val Ala Pro
                20                  25                  30

Ala Ser Ser Leu Asn Val Arg Phe Asp Ser Arg Thr Met Asn Leu Ser
            35                  40                  45

Trp Asp Cys Gln Glu Asn Thr Thr Phe Ser Lys Cys Phe Leu Thr Asp
        50                  55                  60

Lys Lys Asn Arg Val Val Glu Pro Arg Leu Ser Asn Asn Glu Cys Ser
65                  70                  75                  80

Cys Thr Phe Arg Glu Ile Cys Leu His Glu Gly Val Thr Phe Glu Val
                85                  90                  95

His Val Asn Thr Ser Gln Arg Gly Phe Gln Gln Lys Leu Leu Tyr Pro
                100                 105                 110

Asn Ser Gly Arg Glu Gly Thr Ala Ala Gln Asn Phe Ser Cys Phe Ile
            115                 120                 125

Tyr Asn Ala Asp Leu Met Asn Cys Thr Trp Ala Arg Gly Pro Thr Ala
        130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
                165                 170                 175

Gly Cys His Leu Asp Asn Leu Ser Gly Leu Thr Ser Arg Asn Tyr Phe
                180                 185                 190

Leu Val Asn Gly Thr Ser Arg Glu Ile Gly Ile Gln Phe Phe Asp Ser
            195                 200                 205
```

```
Leu Leu Asp Thr Lys Lys Ile Glu Arg Phe Asn Pro Pro Ser Asn Val
    210             215                 220

Thr Val Arg Cys Asn Thr Thr His Cys Leu Val Arg Trp Lys Gln Pro
225             230                 235                 240

Arg Thr Tyr Gln Lys Leu Ser Tyr Leu Asp Phe Gln Tyr Gln Leu Asp
            245                 250                 255

Val His Arg Lys Asn Thr Gln Pro Gly Thr Glu Asn Leu Leu Ile Asn
            260                 265                 270

Val Ser Gly Asp Leu Glu Asn Arg Tyr Asn Phe Pro Ser Ser Glu Pro
        275                 280                 285

Arg Ala Lys His Ser Val Lys Ile Arg Ala Ala Asp Val Arg Ile Leu
    290                 295                 300

Asn Trp Ser Ser Trp Ser Glu Ala Ile Glu Phe Gly Ser Asp Asp Gly
305             310                 315                 320

Met Ile Ile Ala Val Leu Ile Leu Val Ala Val Val Cys Leu Val Thr
            325                 330                 335

Val Cys Val Ile Tyr Arg Val Asp Leu Val Leu Phe Tyr Arg His Leu
            340                 345                 350

Thr Arg Arg Asp Glu Thr Leu Thr Asp Gly Lys Thr Tyr Asp Ala Phe
        355                 360                 365

Val Ser Tyr Leu Lys Glu Cys Arg Pro Glu Asn Gly Glu Glu His Thr
    370                 375                 380

Phe Ala Val Glu Ile Leu Pro Arg Val Leu Glu Lys His Phe Gly Tyr
385             390                 395                 400

Lys Leu Cys Ile Phe Glu Arg Asp Val Val Pro Gly Gly Ala Val Val
            405                 410                 415

Asp Glu Ile His Ser Leu Ile Glu Lys Ser Arg Arg Leu Ile Ile Val
            420                 425                 430

Leu Ser Lys Ser Tyr Met Ser Asn Glu Val Arg Tyr Glu Leu Glu Ser
        435                 440                 445

Gly Leu His Glu Ala Leu Val Glu Arg Lys Ile Lys Ile Ile Leu Ile
    450                 455                 460

Glu Phe Thr Pro Val Thr Asp Phe Thr Phe Leu Pro Gln Ser Leu Lys
465             470                 475                 480

Leu Leu Lys Ser His Arg Val Leu Lys Trp Lys Ala Asp Lys Ser Leu
            485                 490                 495

Ser Tyr Asn Ser Arg Phe Trp Lys Asn Leu Leu Tyr Leu Met Pro Ala
            500                 505                 510

Lys Thr Val Lys Pro Gly Arg Asp Glu Pro Glu Val Leu Pro Val Leu
        515                 520                 525

Ser Glu Ser
    530
```

```
<210> SEQ ID NO 18
<211> LENGTH: 1596
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atgctgctgc tggtcacatc tctgctgctg tgcgagctgc cccatcctgc ctttctgctg      60
atccccgaga agtccgacct gagaacagtg gcccctgcca gctctctgaa cgttcgcttc     120
```

```
gacagccgga ccatgaacct gagctgggac tgccaagaga acacaacctt cagcaagtgc      180
ttcctgaccg acaagaagaa ccgggtcgtc gagcccagac tgagcaacaa tgagtgctcc      240
tgcaccttca gagagatctg cctgcacgag ggcgtgacct ttgaggtgca cgtgaacaca      300
agccagcggg gctttcagca gaagctgctg taccccaata gcggcagaga gggaaccgcc      360
gctcagaact tcagctgctt catctacaac gccgacctca tgaactgcac ctgggccaga      420
ggacctaccg ctcctagaga tgtgcagtac ttcctgtaca ttcggaacag caagcggcgg      480
agagaaatca ggtgcccta ctacatccaa gacagcggca cacgtgggg ctgccacctg      540 gataatctgt ctggcctgac cagccggaac tacttcctgg tcaatggcac cagccgcgag      600
atcggcatcc agttctttga cagcctgctg gacaccaaga agatcgagcg gttcaaccct      660
cctagcaacg tgaccgtgcg gtgcaacacc acacattgtc tcgtgcggtg gaagcagccc      720
cggacatacc agaagctgag ctacctggac ttccagtacc agctggatgt gcaccggaag      780
aacacccagc ctggcaccga gaacctgctg atcaatgtgt ccggcgacct ggaaaaccgg      840
tacaacttcc ctagcagcga gcccagggcc aagcacagcg tgaaaattag agccgccgat      900
gtgcgcatcc tgaactggtc ctcttggagc gaggccatcg agtttggatc cgacgacggc      960
atgatcattg ccgtgctgat cctggtggcc gtcgtgtgtc tggtcaccgt gtgcgtgatc     1020
tacagagtgg acctggtgct gttctaccgg cacctgacca agagggacga gacactgacc     1080
gacggcaaga cctacgatgc cttcgtgtcc tacctgaaag agtgcagacc cgagaacggc     1140
gaggaacaca ccttcgccgt ggaaatcctg cctagagtgc tggaaaagca cttcggctac     1200
aagctgtgca tcttcgagag ggacgttgtg cctggcggag ctgtggtgga tgagatccac     1260
agcctgatcg agaagtccag acggctgatc atcgtgctga gcaagagcta catgagcaac     1320
gaagtccgct acgagctgga aagcggactg cacgaagccc tggtggaacg gaagatcaag     1380
atcatcctga ttgagttcac ccctgtgacc gacttcacat tcctgcctca gagcctgaag     1440
ctgctgaagt cccacagagt gctgaagtgg aaggccgaca gagcctgag ctacaacagc     1500 cggttctgga gaacctgct gtacctgatg cctgccaaga ccgtgaagcc cggcagagat     1560
gaacctgagg tgctgcctgt gctgagcgag tcttaa                              1596
```

```
<210> SEQ ID NO 19
<211> LENGTH: 691
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Val Leu Ala Gln Gly Leu Leu Ser Met Ala Leu Leu Ala Leu Cys
1               5                   10                  15

Trp Glu Arg Ser Leu Ala Gly Ala Glu Glu Thr Ile Pro Leu Gln Thr
            20                  25                  30

Leu Arg Cys Tyr Asn Asp Tyr Thr Ser His Ile Thr Cys Arg Trp Ala
        35                  40                  45

Asp Thr Gln Asp Ala Gln Arg Leu Val Asn Val Thr Leu Ile Arg Arg
    50                  55                  60

Val Asn Glu Asp Leu Leu Glu Pro Val Ser Cys Asp Leu Ser Asp Asp
65                  70                  75                  80

Met Pro Trp Ser Ala Cys Pro His Pro Arg Cys Val Pro Arg Arg Cys
                85                  90                  95
```

-continued

```
Val Ile Pro Cys Gln Ser Phe Val Val Thr Asp Val Asp Tyr Phe Ser
            100                 105                 110

Phe Gln Pro Asp Arg Pro Leu Gly Thr Arg Leu Thr Val Thr Leu Thr
            115                 120                 125

Gln His Val Gln Pro Pro Glu Pro Arg Asp Leu Gln Ile Ser Thr Asp
        130                 135                 140

Gln Asp His Phe Leu Leu Thr Trp Ser Val Ala Leu Gly Ser Pro Gln
145                 150                 155                 160

Ser His Trp Leu Ser Pro Gly Asp Leu Glu Phe Glu Val Val Tyr Lys
                165                 170                 175

Arg Leu Gln Asp Ser Trp Glu Asp Ala Ala Ile Leu Leu Ser Asn Thr
            180                 185                 190

Ser Gln Ala Thr Leu Gly Pro Glu His Leu Met Pro Ser Ser Thr Tyr
            195                 200                 205

Val Ala Arg Val Arg Thr Arg Leu Ala Pro Gly Ser Arg Leu Ser Gly
        210                 215                 220

Arg Pro Ser Lys Trp Ser Pro Glu Val Cys Trp Asp Ser Gln Pro Gly
225                 230                 235                 240

Asp Glu Ala Gln Pro Gln Asn Leu Glu Cys Phe Phe Asp Gly Ala Ala
            245                 250                 255

Val Leu Ser Cys Ser Trp Glu Val Arg Lys Glu Val Ala Ser Ser Val
            260                 265                 270

Ser Phe Gly Leu Phe Tyr Lys Pro Ser Pro Asp Ala Gly Ser Ala Val
            275                 280                 285

Leu Leu Arg Glu Glu Glu Cys Ser Pro Val Leu Arg Glu Gly Leu Gly
        290                 295                 300

Ser Leu His Thr Arg His His Cys Gln Ile Pro Val Pro Asp Pro Ala
305                 310                 315                 320

Thr His Gly Gln Tyr Ile Val Ser Val Gln Pro Arg Arg Ala Glu Lys
                325                 330                 335

His Ile Lys Ser Ser Val Asn Ile Gln Met Ala Pro Pro Ser Leu Asn
            340                 345                 350

Val Thr Lys Asp Gly Asp Ser Tyr Ser Leu Arg Trp Glu Thr Met Lys
            355                 360                 365

Met Arg Tyr Glu His Ile Asp His Thr Phe Glu Ile Gln Tyr Arg Lys
        370                 375                 380

Asp Thr Ala Thr Trp Lys Asp Ser Lys Thr Glu Thr Leu Gln Asn Ala
385                 390                 395                 400

His Ser Met Ala Leu Pro Ala Leu Glu Pro Ser Thr Arg Tyr Trp Ala
                405                 410                 415

Arg Val Arg Val Arg Thr Ser Arg Thr Gly Tyr Asn Gly Ile Trp Ser
            420                 425                 430

Glu Trp Ser Glu Ala Arg Ser Trp Asp Thr Glu Ser Val Leu Pro Met
            435                 440                 445

Trp Gly Val Leu Leu Tyr Ile Leu Leu Gly Thr Ile Gly Thr Leu Val
        450                 455                 460

Ala Val Leu Ala Ala Ser Ala Leu Leu Tyr Arg His Trp Ile Glu Ile
465                 470                 475                 480

Val Leu Leu Tyr Arg Thr Tyr Gln Ser Lys Asp Gln Thr Leu Gly Asp
                485                 490                 495

Lys Lys Asp Phe Asp Ala Phe Val Ser Tyr Ala Lys Trp Ser Ser Phe
            500                 505                 510

Pro Ser Glu Ala Thr Ser Ser Leu Ser Glu Glu His Leu Ala Leu Ser
```

-continued

```
              515               520               525
Leu Phe Pro Asp Val Leu Glu Asn Lys Tyr Gly Tyr Ser Leu Cys Leu
        530               535               540
Leu Glu Arg Asp Val Ala Pro Gly Gly Val Tyr Ala Glu Asp Ile Val
545               550               555               560
Ser Ile Ile Lys Arg Ser Arg Arg Gly Ile Phe Ile Leu Ser Pro Asn
                565               570               575
Tyr Val Asn Gly Pro Ser Ile Phe Glu Leu Gln Ala Ala Val Asn Leu
            580               585               590
Ala Leu Asp Asp Gln Thr Leu Lys Leu Ile Leu Ile Lys Phe Cys Tyr
        595               600               605
Phe Gln Glu Pro Glu Ser Leu Pro His Leu Val Lys Lys Ala Leu Arg
    610               615               620
Val Leu Pro Thr Val Thr Trp Arg Gly Leu Lys Ser Val Pro Pro Asn
625               630               635               640
Ser Arg Phe Trp Ala Lys Met Arg Tyr His Met Pro Val Lys Asn Ser
                645               650               655
Gln Gly Phe Thr Trp Asn Gln Leu Arg Ile Thr Ser Arg Ile Phe Gln
            660               665               670
Trp Lys Gly Leu Ser Arg Thr Glu Thr Thr Gly Arg Ser Ser Gln Pro
        675               680               685
Lys Glu Trp
    690
```

<210> SEQ ID NO 20
<211> LENGTH: 2073
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
atggttctgg cccagggcct gctgtctatg gctctgcttg ctctgtgctg ggagagaagt      60
ctggctggcg ccgaggaaac aatccctctg cagaccctgc ggtgctacaa cgactacacc     120
agccacatca cctgtagatg ggccgacaca caggacgccc agagactggt caatgtgacc     180
ctgatcagaa gagtgaacga ggacctgctg aacccgtgt cctgtgacct gagcgacgat      240
atgccttgga gcgcctgtcc tcatcctaga tgtgtgcctc ggagatgcgt gatccctgc      300 cagagctttg tggtcaccga tgtggactac ttcagcttcc agcctgacag accccctgggc     360 accagactga cagtgacact gacacagcac gtgcagcctc cagagcctag ggacctgcag     420
atctctaccg accaggacca cttcctgctg acttggagtg tggccctggg aagccctcag     480
tctcattggc ttagccctgg cgacctggaa ttcgaggtgg tgtacaagag actgcaggac     540
agctgggaag atgccgccat cctgctgagc aataccagcc aggctacact gggcccccgaa     600 cacctgatgc ctagctctac ctatgtggcc agagtgcgga caagactggc ccctggatct     660
agactgagcg gcagaccttc taagtggtcc cctgaagtct gctgggatag ccagcctggg     720
gatgaagccc agcctcagaa cctggaatgc ttcttcgatg cgccgctgt gctgagctgt      780 tcttgggaag tgcggaaaga ggtggccagc agcgttagct tcggcctgtt ctacaagccc     840
tctccagatg ccggatctgc cgtgctgctg agagaagagg aatgcagccc cgtgctcaga     900
gaaggcctgg atctctgca caccagacac cactgtcaga tccccgtgcc tgatcctgcc      960
acacacggcc agtatatcgt gtccgtgcag ccaagaaggg ccgagaagca catcaagagc    1020
```

-continued

```
agcgtgaaca tccagatggc ccctccaagc ctgaacgtga ccaaggacgg cgacagctac      1080
agcctgagat gggagacaat gaagatgcgc tacgagcaca tcgaccacac cttcgagatc      1140
cagtaccgga aggataccgc cacctggaag gacagcaaga ccgagacact gcagaacgcc      1200
cactctatgg cactgccagc tctcgagccc tccaccagat attgggccag agtcagagtg      1260
cggaccagca gaacaggcta caacggcatt tggagcgagt ggagcgaagc cagaagctgg      1320
gatacagagt ctgtactacc aatgtggggc gtgctgctgt acatcctgct gggcacaatc      1380
ggaacactgg tggctgtgct ggctgccagc gctctgctgt atagacactg gatcgagatc      1440
gtcctgctgt accggaccta ccagagcaag gatcagaccc tgggcgacaa gaaggacttc      1500
gacgcctttg tgtcctacgc caagtggtcc agctttccca gcgaggccac aagcagcctg      1560
agcgaagaac atctggccct gtctctgttc cccgatgtgc tggaaaacaa atacggctac      1620
agcctgtgcc tgctggaaag agatgttgcc cctggcggag tgtacgccga ggatatcgtg      1680
tccatcatca gcggagcag acggggcatc ttcattctga gccccaacta cgtgaacggc       1740
cccagcatct ttgaactgca gccgccgtg aacctggctc tggacgatca gacactgaag       1800
ctgatcctga tcaagttctg ctacttccaa gagcctgaga gcctgcctca cctggtcaag      1860
aaagccctga gagtgctgcc taccgtgact tggagaggcc tgaagtccgt gcctcctaac      1920
agcagattct gggccaagat gagataccac atgcctgtga agaacagcca gggcttcacc      1980
tggaaccagc tgcggatcac ctccagaatc ttccagtgga agggcctgag ccggaccgag      2040
acaacaggca gaagcagcca gcctaaagag tgg                                    2073
```

```
<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ser Gly Glu Gly Arg Gly Ser Leu Leu Thr Cys Gly Asp Val Glu
1               5                   10                  15

Glu Asn Pro Gly Pro
            20
```

```
<210> SEQ ID NO 22
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggctccggag agggcagagg cagcctgctg acatgtggcg acgtggaaga gaacccaggc      60
cca                                                                     63
```

```
<210> SEQ ID NO 23
<211> LENGTH: 1243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23
```

-continued

```
Met Val Leu Ala Gln Gly Leu Leu Ser Met Ala Leu Leu Ala Leu Cys
1               5                   10                  15

Trp Glu Arg Ser Leu Ala Gly Ala Glu Glu Thr Ile Pro Leu Gln Thr
                20                  25                  30

Leu Arg Cys Tyr Asn Asp Tyr Thr Ser His Ile Thr Cys Arg Trp Ala
            35                  40                  45

Asp Thr Gln Asp Ala Gln Arg Leu Val Asn Val Thr Leu Ile Arg Arg
        50                  55                  60

Val Asn Glu Asp Leu Leu Glu Pro Val Ser Cys Asp Leu Ser Asp Asp
65                  70                  75                  80

Met Pro Trp Ser Ala Cys Pro His Pro Arg Cys Val Pro Arg Arg Cys
                85                  90                  95

Val Ile Pro Cys Gln Ser Phe Val Val Thr Asp Val Asp Tyr Phe Ser
            100                 105                 110

Phe Gln Pro Asp Arg Pro Leu Gly Thr Arg Leu Thr Val Thr Leu Thr
        115                 120                 125

Gln His Val Gln Pro Pro Glu Pro Arg Asp Leu Gln Ile Ser Thr Asp
        130                 135                 140

Gln Asp His Phe Leu Leu Thr Trp Ser Val Ala Leu Gly Ser Pro Gln
145                 150                 155                 160

Ser His Trp Leu Ser Pro Gly Asp Leu Glu Phe Glu Val Val Tyr Lys
                165                 170                 175

Arg Leu Gln Asp Ser Trp Glu Asp Ala Ala Ile Leu Leu Ser Asn Thr
            180                 185                 190

Ser Gln Ala Thr Leu Gly Pro Glu His Leu Met Pro Ser Ser Thr Tyr
            195                 200                 205

Val Ala Arg Val Arg Thr Arg Leu Ala Pro Gly Ser Arg Leu Ser Gly
        210                 215                 220

Arg Pro Ser Lys Trp Ser Pro Glu Val Cys Trp Asp Ser Gln Pro Gly
225                 230                 235                 240

Asp Glu Ala Gln Pro Gln Asn Leu Glu Cys Phe Phe Asp Gly Ala Ala
                245                 250                 255

Val Leu Ser Cys Ser Trp Glu Val Arg Lys Glu Val Ala Ser Ser Val
            260                 265                 270

Ser Phe Gly Leu Phe Tyr Lys Pro Ser Pro Asp Ala Gly Ser Ala Val
            275                 280                 285

Leu Leu Arg Glu Glu Glu Cys Ser Pro Val Leu Arg Glu Gly Leu Gly
        290                 295                 300

Ser Leu His Thr Arg His His Cys Gln Ile Pro Val Pro Asp Pro Ala
305                 310                 315                 320

Thr His Gly Gln Tyr Ile Val Ser Val Gln Pro Arg Arg Ala Glu Lys
                325                 330                 335

His Ile Lys Ser Ser Val Asn Ile Gln Met Ala Pro Pro Ser Leu Asn
            340                 345                 350

Val Thr Lys Asp Gly Asp Ser Tyr Ser Leu Arg Trp Glu Thr Met Lys
            355                 360                 365

Met Arg Tyr Glu His Ile Asp His Thr Phe Glu Ile Gln Tyr Arg Lys
        370                 375                 380

Asp Thr Ala Thr Trp Lys Asp Ser Lys Thr Glu Thr Leu Gln Asn Ala
385                 390                 395                 400

His Ser Met Ala Leu Pro Ala Leu Glu Pro Ser Thr Arg Tyr Trp Ala
                405                 410                 415
```

-continued

Arg Val Arg Val Arg Thr Ser Arg Thr Gly Tyr Asn Gly Ile Trp Ser
        420             425             430

Glu Trp Ser Glu Ala Arg Ser Trp Asp Thr Glu Ser Val Leu Pro Met
        435             440             445

Trp Gly Val Leu Leu Tyr Ile Leu Leu Gly Thr Ile Gly Thr Leu Val
    450             455             460

Ala Val Leu Ala Ala Ser Ala Leu Leu Tyr Arg His Trp Ile Glu Ile
465             470             475             480

Val Leu Leu Tyr Arg Thr Tyr Gln Ser Lys Asp Gln Thr Leu Gly Asp
            485             490             495

Lys Lys Asp Phe Asp Ala Phe Val Ser Tyr Ala Lys Trp Ser Ser Phe
        500             505             510

Pro Ser Glu Ala Thr Ser Ser Leu Ser Glu Glu His Leu Ala Leu Ser
        515             520             525

Leu Phe Pro Asp Val Leu Glu Asn Lys Tyr Gly Tyr Ser Leu Cys Leu
        530             535             540

Leu Glu Arg Asp Val Ala Pro Gly Gly Val Tyr Ala Glu Asp Ile Val
545             550             555             560

Ser Ile Ile Lys Arg Ser Arg Arg Gly Ile Phe Ile Leu Ser Pro Asn
            565             570             575

Tyr Val Asn Gly Pro Ser Ile Phe Glu Leu Gln Ala Ala Val Asn Leu
            580             585             590

Ala Leu Asp Asp Gln Thr Leu Lys Leu Ile Leu Ile Lys Phe Cys Tyr
        595             600             605

Phe Gln Glu Pro Glu Ser Leu Pro His Leu Val Lys Lys Ala Leu Arg
        610             615             620

Val Leu Pro Thr Val Thr Trp Arg Gly Leu Lys Ser Val Pro Pro Asn
625             630             635             640

Ser Arg Phe Trp Ala Lys Met Arg Tyr His Met Pro Val Lys Asn Ser
            645             650             655

Gln Gly Phe Thr Trp Asn Gln Leu Arg Ile Thr Ser Arg Ile Phe Gln
            660             665             670

Trp Lys Gly Leu Ser Arg Thr Glu Thr Thr Gly Arg Ser Ser Gln Pro
        675             680             685

Lys Glu Trp Gly Ser Gly Glu Gly Arg Gly Ser Leu Leu Thr Cys Gly
    690             695             700

Asp Val Glu Glu Asn Pro Gly Pro Met Leu Leu Leu Val Thr Ser Leu
705             710             715             720

Leu Leu Cys Glu Leu Pro His Pro Ala Phe Leu Leu Ile Pro Glu Lys
            725             730             735

Ser Asp Leu Arg Thr Val Ala Pro Ala Ser Ser Leu Asn Val Arg Phe
            740             745             750

Asp Ser Arg Thr Met Asn Leu Ser Trp Asp Cys Gln Glu Asn Thr Thr
        755             760             765

Phe Ser Lys Cys Phe Leu Thr Asp Lys Lys Asn Arg Val Val Glu Pro
    770             775             780

Arg Leu Ser Asn Asn Glu Cys Ser Cys Thr Phe Arg Glu Ile Cys Leu
785             790             795             800

His Glu Gly Val Thr Phe Glu Val His Val Asn Thr Ser Gln Arg Gly
            805             810             815

Phe Gln Gln Lys Leu Leu Tyr Pro Asn Ser Gly Arg Glu Gly Thr Ala
        820             825             830

Ala Gln Asn Phe Ser Cys Phe Ile Tyr Asn Ala Asp Leu Met Asn Cys

-continued

```
              835                840                845
Thr Trp Ala Arg Gly Pro Thr Ala Pro Arg Asp Val Gln Tyr Phe Leu
    850                855                860

Tyr Ile Arg Asn Ser Lys Arg Arg Arg Glu Ile Arg Cys Pro Tyr Tyr
865                870                875                880

Ile Gln Asp Ser Gly Thr His Val Gly Cys His Leu Asp Asn Leu Ser
                885                890                895

Gly Leu Thr Ser Arg Asn Tyr Phe Leu Val Asn Gly Thr Ser Arg Glu
            900                905                910

Ile Gly Ile Gln Phe Phe Asp Ser Leu Leu Asp Thr Lys Lys Ile Glu
            915                920                925

Arg Phe Asn Pro Pro Ser Asn Val Thr Val Arg Cys Asn Thr Thr His
    930                935                940

Cys Leu Val Arg Trp Lys Gln Pro Arg Thr Tyr Gln Lys Leu Ser Tyr
945                950                955                960

Leu Asp Phe Gln Tyr Gln Leu Asp Val His Arg Lys Asn Thr Gln Pro
                965                970                975

Gly Thr Glu Asn Leu Leu Ile Asn Val Ser Gly Asp Leu Glu Asn Arg
                980                985                990

Tyr Asn Phe Pro Ser Ser Glu Pro  Arg Ala Lys His Ser  Val Lys Ile
        995                1000                1005

Arg Ala  Ala Asp Val Arg Ile  Leu Asn Trp Ser Ser  Trp Ser Glu
    1010                1015                1020

Ala Ile  Glu Phe Gly Ser Asp  Asp Gly Met Ile Ile  Ala Val Leu
    1025                1030                1035

Ile Leu  Val Ala Val Val Cys  Leu Val Thr Val Cys  Val Ile Tyr
    1040                1045                1050

Arg Val  Asp Leu Val Leu Phe  Tyr Arg His Leu Thr  Arg Arg Asp
    1055                1060                1065

Glu Thr  Leu Thr Asp Gly Lys  Thr Tyr Asp Ala Phe  Val Ser Tyr
    1070                1075                1080

Leu Lys  Glu Cys Arg Pro Glu  Asn Gly Glu Glu His  Thr Phe Ala
    1085                1090                1095

Val Glu  Ile Leu Pro Arg Val  Leu Glu Lys His Phe  Gly Tyr Lys
    1100                1105                1110

Leu Cys  Ile Phe Glu Arg Asp  Val Val Pro Gly Gly  Ala Val Val
    1115                1120                1125

Asp Glu  Ile His Ser Leu Ile  Glu Lys Ser Arg Arg  Leu Ile Ile
    1130                1135                1140

Val Leu  Ser Lys Ser Tyr Met  Ser Asn Glu Val Arg  Tyr Glu Leu
    1145                1150                1155

Glu Ser  Gly Leu His Glu Ala  Leu Val Glu Arg Lys  Ile Lys Ile
    1160                1165                1170

Ile Leu  Ile Glu Phe Thr Pro  Val Thr Asp Phe Thr  Phe Leu Pro
    1175                1180                1185

Gln Ser  Leu Lys Leu Leu Lys  Ser His Arg Val Leu  Lys Trp Lys
    1190                1195                1200

Ala Asp  Lys Ser Leu Ser Tyr  Asn Ser Arg Phe Trp  Lys Asn Leu
    1205                1210                1215

Leu Tyr  Leu Met Pro Ala Lys  Thr Val Lys Pro Gly  Arg Asp Glu
    1220                1225                1230

Pro Glu  Val Leu Pro Val Leu  Ser Glu Ser
    1235                1240
```

-continued

```
<210> SEQ ID NO 24
<211> LENGTH: 3732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
atggttctgg cccagggcct gctgtctatg gctctgcttg ctctgtgctg ggagagaagt      60
ctggctggcg ccgaggaaac aatccctctg cagaccctgc ggtgctacaa cgactacacc     120
agccacatca cctgtagatg ggccgacaca caggacgccc agagactggt caatgtgacc     180
ctgatcagaa gagtgaacga ggacctgctg gaacccgtgt cctgtgacct gagcgacgat     240
atgccttgga gcgcctgtcc tcatcctaga tgtgtgcctc ggagatgcgt gatcccctgc     300
cagagctttg tggtcaccga tgtggactac ttcagcttcc agcctgacag acccctgggc     360
accagactga cagtgacact gacacagcac gtgcagcctc agagcctag ggacctgcag      420 atctctaccg accaggacca cttcctgctg acttggagtg tggccctggg aagccctcag     480
tctcattggc ttagccctgg cgacctggaa ttcgaggtgg tgtacaagag actgcaggac     540
agctgggaag atgccgccat cctgctgagc aataccagcc aggctacact gggccccgaa     600
cacctgatgc ctagctctac ctatgtggcc agagtgcgga caagactggc ccctggatct     660
agactgagcg gcagaccttc taagtggtcc cctgaagtct gctgggatag ccagcctggg     720
gatgaagccc agcctcagaa cctggaatgc ttcttcgatg gcgccgctgt gctgagctgt     780
tcttgggaag tgcggaaaga ggtggccagc agcgttagct cggcctgtt ctacaagccc      840 tctccagatg ccggatctgc cgtgctgctg agagaagagg aatgcagccc cgtgctcaga     900
gaaggcctgg atctctgca caccagacac cactgtcaga tccccgtgcc tgatcctgcc      960
acacacggcc agtatatcgt gtccgtgcag ccaagaaggg ccgagaagca catcaagagc    1020
agcgtgaaca tccagatggc ccctccaagc ctgaacgtga ccaaggacgg cgacagctac    1080
agcctgagat gggagacaat gaagatgcgc tacgagcaca tcgaccacac cttcgagatc    1140
cagtaccgga aggataccgc cacctggaag gacagcaaga ccgagacact gcagaacgcc    1200
cactctatgg cactgccagc tctcgagccc tccaccagat attgggccag agtcagagtg    1260
cggaccagca gaacaggcta caacggcatt tggagcgagt ggagcgaagc cagaagctgg    1320
gatacagagt ctgtactacc aatgtggggc gtgctgctgt acatcctgct gggcacaatc    1380
ggaacactgg tggctgtgct ggctgccagc gctctgctgt atagacactg gatcgagatc    1440
gtcctgctgt accggaccta ccagagcaag gatcagaccc tgggcgacaa gaaggacttc    1500
gacgcctttg tgtcctacgc caagtggtcc agctttccca gcgaggccac aagcagcctg    1560
agcgaagaac atctggccct gtctctgttc cccgatgtgc tggaaaacaa atacggctac    1620
agcctgtgcc tgctggaaag agatgttgcc cctggcggag tgtacgccga ggatatcgtg    1680
tccatcatca gcggagcag acggggcatc ttcattctga gccccaacta cgtgaacggc    1740
cccagcatct ttgaactgca agccgccgtg aacctggctc tggacgatca gacactgaag    1800
ctgatcctga tcaagttctg ctacttccaa gagcctgaga gcctgcctca cctggtcaag    1860
aaagccctga gagtgctgcc taccgtgact tggagaggcc tgaagtccgt gcctcctaac    1920
agcagattct gggccaagat gagataccac atgcctgtga gaacagcca gggcttcacc     1980 tggaaccagc tgcggatcac ctccagaatc ttccagtgga agggcctgag ccggaccgag    2040
```

-continued

```
acaacaggca gaagcagcca gcctaaagag tggggctccg gagagggcag aggcagcctg    2100
ctgacatgtg gcgacgtgga agagaaccca ggcccaatgc tgctgctggt cacatctctg    2160
ctgctgtgcg agctgcccca tcctgccttt ctgctgatcc ccgagaagtc cgacctgaga    2220
acagtggccc ctgccagctc tctgaacgtt cgcttcgaca gccggaccat gaacctgagc    2280
tgggactgcc aagagaacac aaccttcagc aagtgcttcc tgaccgacaa gaagaaccgg    2340
gtcgtcgagc ccagactgag caacaatgag tgctcctgca ccttcagaga gatctgcctg    2400
cacgagggcg tgacctttga ggtgcacgtg aacacaagcc agcggggctt tcagcagaag    2460
ctgctgtacc ccaatagcgg cagagaggga accgccgctc agaacttcag ctgcttcatc    2520
tacaacgccg acctcatgaa ctgcacctgg gccagaggac ctaccgctcc tagagatgtg    2580
cagtacttcc tgtacattcg gaacagcaag cggcggagag aaatcaggtg cccctactac    2640
atccaagaca gcggcacaca cgtgggctgc cacctggata tctgtctgg cctgaccagc    2700 cggaactact tcctggtcaa tggcaccagc cgcgagatcg gcatccagtt ctttgacagc    2760
ctgctggaca ccaagaagat cgagcggttc aaccctccta gcaacgtgac cgtgcggtgc    2820
aacaccacac attgtctcgt gcggtggaag cagccccgga cataccagaa gctgagctac    2880
ctggacttcc agtaccagct ggatgtgcac cggaagaaca cccagcctgg caccgagaac    2940
ctgctgatca atgtgtccgg cgacctggaa aaccggtaca acttccctag cagcgagccc    3000
agggccaagc acagcgtgaa aattagagcc gccgatgtgc gcatcctgaa ctggtcctct    3060
tggagcgagg ccatcgagtt tggatccgac gacggcatga tcattgccgt gctgatcctg    3120
gtggccgtcg tgtgtctggt caccgtgtgc gtgatctaca gagtggacct ggtgctgttc    3180
taccggcacc tgaccagaag ggacgagaca ctgaccgacg gcaagaccta cgatgccttc    3240
gtgtcctacc tgaaagagtg cagacccgag aacggcgagg aacacacctt cgccgtggaa    3300
atcctgccta gagtgctgga aaagcacttc ggctacaagc tgtgcatctt cgagagggac    3360
gttgtgcctg gcggagctgt ggtggatgag atccacagcc tgatcgagaa gtccagacgg    3420
ctgatcatcg tgctgagcaa gagctacatg agcaacgaag tccgctacga gctggaaagc    3480
ggactgcacg aagccctggt ggaacggaag atcaagatca tcctgattga gttcaccccct    3540 gtgaccgact tcacattcct gcctcagagc ctgaagctgc tgaagtccca cagagtgctg    3600
aagtggaagg ccgacaagag cctgagctac aacagccggt tctggaagaa cctgctgtac    3660
ctgatgcctg ccaagaccgt gaagcccggc agagatgaac ctgaggtgct gcctgtgctg    3720
agcgagtctt aa                                                        3732
```

<210> SEQ ID NO 25
<211> LENGTH: 377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
ccatatgaga tcttatatgg ggcacccccg ccccttgtaa acttccctga ccctgacatg      60
acaagagtta ctaacagccc ctctctccaa gctcacttac aggctctcta cttagtccag     120
cacgaagtct ggagacctct ggcggcagcc taccaagaac aactggaccg accggtggta     180 cctcacccttt accgagtcgg cgacacagtg tgggtccgcc gacaccagac taagaaccta     240
gaacctcgct ggaaaggacc ttacacagtc ctgctgacca cccccaccgc cctcaaagta     300
```

-continued

```
gacggcatcg cagcttggat acacgccgcc cacgtgaagg ctgccgaccc cgggggtgga      360
ccatcctcta gactgcc                                                     377
```

<210> SEQ ID NO 26
<211> LENGTH: 462
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 26

```
Met Asp Trp Ile Trp Arg Ile Leu Phe Leu Val Gly Ala Ala Thr Gly
1               5                   10                  15

Ala His Ser Glu Val Gln Leu Gln Gln Ser Gly Pro Glu Leu Lys Lys
                20                  25                  30

Pro Gly Glu Thr Val Lys Ile Ser Cys Lys Ala Ser Gly Tyr Pro Phe
            35                  40                  45

Thr Asn Tyr Gly Met Asn Trp Val Lys Gln Ala Pro Gly Gln Gly Leu
        50                  55                  60

Lys Trp Met Gly Trp Ile Asn Thr Ser Thr Gly Glu Ser Thr Phe Ala
65                  70                  75                  80

Asp Asp Phe Lys Gly Arg Phe Asp Phe Ser Leu Glu Thr Ser Ala Asn
                85                  90                  95

Thr Ala Tyr Leu Gln Ile Asn Asn Leu Lys Ser Glu Asp Met Ala Thr
                100                 105                 110

Tyr Phe Cys Ala Arg Trp Glu Val Tyr His Gly Tyr Val Pro Tyr Trp
            115                 120                 125

Gly Gln Gly Thr Thr Val Thr Val Ser Ser Gly Gly Gly Gly Ser Gly
        130                 135                 140

Gly Gly Gly Ser Gly Gly Gly Gly Ser Asp Ile Gln Leu Thr Gln Ser
145                 150                 155                 160

His Lys Phe Leu Ser Thr Ser Val Gly Asp Arg Val Ser Ile Thr Cys
                165                 170                 175

Lys Ala Ser Gln Asp Val Tyr Asn Ala Val Ala Trp Tyr Gln Gln Lys
                180                 185                 190

Pro Gly Gln Ser Pro Lys Leu Leu Ile Tyr Ser Ala Ser Ser Arg Tyr
            195                 200                 205

Thr Gly Val Pro Ser Arg Phe Thr Gly Ser Gly Ser Gly Pro Asp Phe
        210                 215                 220

Thr Phe Thr Ile Ser Ser Val Gln Ala Glu Asp Leu Ala Val Tyr Phe
225                 230                 235                 240

Cys Gln Gln His Phe Arg Thr Pro Phe Thr Phe Gly Ser Gly Thr Lys
                245                 250                 255

Leu Glu Ile Lys Ala Leu Asp Leu Glu Pro Lys Ser Cys Asp Lys Thr
                260                 265                 270

His Thr Cys Pro Pro Cys Pro Asp Pro Lys Phe Trp Val Leu Val Val
            275                 280                 285

Val Gly Gly Val Leu Ala Cys Tyr Ser Leu Leu Val Thr Val Ala Phe
        290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335
```

-continued

```
Gln Pro Tyr Ala Pro Pro Arg Asp Phe Ala Ala Tyr Arg Ser Arg Val
        340             345             350

Lys Phe Ser Arg Ser Ala Asp Ala Pro Ala Tyr Gln Gln Gly Gln Asn
        355             360             365

Gln Leu Tyr Asn Glu Leu Asn Leu Gly Arg Arg Glu Glu Tyr Asp Val
    370             375             380

Leu Asp Lys Arg Arg Gly Arg Asp Pro Glu Met Gly Gly Lys Pro Arg
385             390             395             400

Arg Lys Asn Pro Gln Glu Gly Leu Tyr Asn Glu Leu Gln Lys Asp Lys
                405             410             415

Met Ala Glu Ala Tyr Ser Glu Ile Gly Met Lys Gly Glu Arg Arg Arg
        420             425             430

Gly Lys Gly His Asp Gly Leu Tyr Gln Gly Leu Ser Thr Ala Thr Lys
        435             440             445

Asp Thr Tyr Asp Ala Leu His Met Gln Ala Leu Pro Pro Arg
    450             455             460
```

<210> SEQ ID NO 27
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
atggactgga tctggcgcat cctcttcctc gtcggcgctg ctaccggcgc tcattctgag      60
gtacaactgc agcagtctgg acctgaactg aagaagcctg gagagacagt caagatctcc     120
tgcaaggcct ctgggtatcc tttcacaaac tatggaatga actgggtgaa gcaggctcca     180
ggacagggtt taaagtggat gggctggatt aacacctcca ctggagagtc aacatttgct     240
gatgacttca agggacggtt tgacttctct ttggaaacct ctgccaacac tgcctatttg     300
cagatcaaca acctcaaaag tgaagacatg gctacatatt tctgtgcaag atgggaggtt     360
taccacggct acgttcctta ctggggccaa gggaccacgg tcaccgtttc tctggcggt     420 ggcggttctg gtggcggtgg ctccggcggt ggcggttctg acatccagct gacccagtct     480
cacaaattcc tgtccacttc agtaggagac agggtcagca tcacctgcaa ggccagtcag     540
gatgtgtata atgctgttgc ctggtatcaa cagaaaccag gacaatctcc taaacttctg     600
atttactcgg catcctcccg gtacactgga gtcccttctc gcttcactgg cagtggctct     660
gggccggatt tcactttcac catcagcagt gtgcaggctg aagacctggc agtttatttc     720
tgtcagcaac attttcgtac tccattcacg ttcggctcgg gacaaaatt ggagatcaaa     780 gctctagatc tcgagcccaa atcttgtgac aaaactcaca tgcccaccg tgcccggat     840 cccaaatttt gggtgctggt ggtggttggt ggagtcctgg cttgctatag cttgctagta     900
acagtggcct ttattatttt ctgggtgagg agtaagagga gcaggctcct gcacagtgac     960
tacatgaaca tgactccccg ccgccccggg cccacccgca agcattacca gccctatgcc    1020
ccaccacgcg acttcgcagc ctatcgctcc agagtgaagt tcagcaggag cgcagacgcc    1080
cccgcgtacc agcagggcca gaaccagctc tataacgagc tcaatctagg acgaagagag    1140
gagtacgatg ttttggacaa gagacgtggc cgggaccctg agatggggg aaagccgaga    1200 aggaagaacc ctcaggaagg cctgtacaat gaactgcaga agataagat ggcggaggcc    1260 tacagtgaga ttgggatgaa aggcgagcgc cggagggca aggggcacga tggcctttac    1320
```

-continued

```
cagggtctca gtacagccac caaggacacc tacgacgccc ttcacatgca ggccctgccc      1380
cctcgctaa                                                             1389
```

<210> SEQ ID NO 28
<211> LENGTH: 810
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Asp Trp Ile Trp Arg Ile Leu Phe Leu Val Gly Ala Ala Thr Gly
1               5                   10                  15

Ala His Ser Gln Val Gln Leu Leu Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Ser Tyr Thr Met Ser Trp Val Arg Gln Ala Pro Gly Gln Ala Leu
        50                  55                  60

Glu Trp Met Gly Thr Ile Ser Ser Gly Gly Thr Tyr Thr Tyr Tyr Pro
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Ala Ile Phe Thr Tyr Trp Gly Arg Gly Thr
        115                 120                 125

Leu Val Thr Ser Ser Gly Gly Gly Gly Ser Gly Gly Gly Gly Ser Gly
    130                 135                 140

Gly Gly Gly Ser Asp Ile Gln Leu Thr Gln Ser Pro Ser Ser Leu Ser
145                 150                 155                 160

Ala Ser Val Gly Asp Arg Val Thr Ile Thr Cys Lys Ala Ser Gln Asp
                165                 170                 175

Ile Asn Asn Tyr Leu Ser Trp Tyr Gln Gln Lys Pro Gly Gln Ala Pro
            180                 185                 190

Arg Leu Leu Ile Tyr Arg Ala Asn Arg Leu Val Asp Gly Val Pro Asp
        195                 200                 205

Arg Phe Ser Gly Ser Gly Tyr Gly Thr Asp Phe Thr Leu Thr Ile Asn
    210                 215                 220

Asn Ile Glu Ser Glu Asp Ala Ala Tyr Tyr Phe Cys Leu Lys Tyr Asp
225                 230                 235                 240

Val Phe Pro Tyr Thr Phe Gly Gln Gly Thr Lys Val Glu Ile Lys Asp
                245                 250                 255

Leu Glu Pro Lys Ser Cys Asp Lys Thr His Thr Cys Pro Pro Cys Pro
            260                 265                 270

Asp Pro Lys Phe Trp Val Leu Val Val Val Gly Gly Val Leu Ala Cys
        275                 280                 285

Tyr Ser Leu Leu Val Thr Val Ala Phe Ile Ile Phe Trp Val Arg Ser
    290                 295                 300

Lys Arg Ser Arg Leu Leu His Ser Asp Tyr Met Asn Met Thr Pro Arg
305                 310                 315                 320

Arg Pro Gly Pro Thr Arg Lys His Tyr Gln Pro Tyr Ala Pro Pro Arg
                325                 330                 335

Asp Phe Ala Ala Tyr Arg Ser Arg Val Lys Phe Ser Arg Ser Ala Asp
```

-continued

```
              340              345              350

Ala Pro Ala Tyr Gln Gln Gly Gln Asn Gln Leu Tyr Asn Glu Leu Asn
        355              360              365

Leu Gly Arg Arg Glu Glu Tyr Asp Val Leu Asp Lys Arg Arg Gly Arg
        370              375              380

Asp Pro Glu Met Gly Gly Lys Pro Arg Arg Lys Asn Pro Gln Glu Gly
385              390              395              400

Leu Tyr Asn Glu Leu Gln Lys Asp Lys Met Ala Glu Ala Tyr Ser Glu
              405              410              415

Ile Gly Met Lys Gly Glu Arg Arg Arg Gly Lys Gly His Asp Gly Leu
              420              425              430

Tyr Gln Gly Leu Ser Thr Ala Thr Lys Asp Thr Tyr Asp Ala Leu His
        435              440              445

Met Gln Ala Leu Pro Pro Arg Ala Ser Arg Ala Glu Gly Arg Gly Ser
        450              455              460

Leu Leu Thr Cys Gly Asp Val Glu Glu Asn Pro Gly Pro Met Pro Pro
465              470              475              480

Pro Arg Leu Leu Phe Phe Leu Leu Phe Leu Thr Pro Met Glu Val Arg
              485              490              495

Pro Glu Glu Pro Leu Val Val Lys Val Glu Glu Gly Asp Asn Ala Val
        500              505              510

Leu Gln Cys Leu Lys Gly Thr Ser Asp Gly Pro Thr Gln Gln Leu Thr
        515              520              525

Trp Ser Arg Glu Ser Pro Leu Lys Pro Phe Leu Lys Leu Ser Leu Gly
        530              535              540

Leu Pro Gly Leu Gly Ile His Met Arg Pro Leu Ala Ile Trp Leu Phe
545              550              555              560

Ile Phe Asn Val Ser Gln Gln Met Gly Gly Phe Tyr Leu Cys Gln Pro
              565              570              575

Gly Pro Pro Ser Glu Lys Ala Trp Gln Pro Gly Trp Thr Val Asn Val
              580              585              590

Glu Gly Ser Gly Glu Leu Phe Arg Trp Asn Val Ser Asp Leu Gly Gly
              595              600              605

Leu Gly Cys Gly Leu Lys Asn Arg Ser Ser Glu Gly Pro Ser Ser Pro
        610              615              620

Ser Gly Lys Leu Met Ser Pro Lys Leu Tyr Val Trp Ala Lys Asp Arg
625              630              635              640

Pro Glu Ile Trp Glu Gly Glu Pro Pro Cys Leu Pro Pro Arg Asp Ser
              645              650              655

Leu Asn Gln Ser Leu Ser Gln Asp Leu Thr Met Ala Pro Gly Ser Thr
              660              665              670

Leu Trp Leu Ser Cys Gly Val Pro Pro Asp Ser Val Ser Arg Gly Pro
        675              680              685

Leu Ser Trp Thr His Val His Pro Lys Gly Pro Lys Ser Leu Leu Ser
        690              695              700

Leu Glu Leu Lys Asp Asp Arg Pro Ala Arg Asp Met Trp Val Met Glu
705              710              715              720

Thr Gly Leu Leu Leu Pro Arg Ala Thr Ala Gln Asp Ala Gly Lys Tyr
              725              730              735

Tyr Cys His Arg Gly Asn Leu Thr Met Ser Phe His Leu Glu Ile Thr
              740              745              750

Ala Arg Pro Val Leu Trp His Trp Leu Leu Arg Thr Gly Gly Trp Lys
        755              760              765
```

Val Ser Ala Val Thr Leu Ala Tyr Leu Ile Phe Cys Leu Cys Ser Leu
    770                 775                 780

Val Gly Ile Leu His Leu Gln Arg Ala Leu Val Leu Arg Arg Lys Arg
785                 790                 795                 800

Lys Arg Met Thr Asp Pro Thr Arg Arg Phe
                805                 810

<210> SEQ ID NO 29
<211> LENGTH: 2433
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
atggactgga tctggcggat tctgttcctc gtgggagccg ccacaggcgc tcactcacag      60
gtgcagctgc tggaatctgg cggcggactg gtgcagcctg gcggcagcct gagactgagc     120
tgcgccgcca gcggcttcac cttcagcagc tacaccatga gctgggtccg gcaggctcct     180
ggacaggccc tggaatggat gggcaccatc agcagcggcg gcacctacac ctactacccc     240
gacagcgtga agggccggtt caccatcagc cgggacaacg ccaagaacag cctgtacctg     300
cagatgaaca gcctgagagc cgaggacaca gccgtgtact actgcgccag agaggccatc     360
ttcacctact ggggcagagg caccctggtc acaagcagcg gaggcggagg aagtggaggg     420
ggaggatcag gcggcggagg cagcgatatc agctgacccc agagccctag cagcctgagc     480
gccagcgtgg gcgacagagt gaccatcaca tgcaaggcca gccaggacat caacaactac     540
ctgagctggt atcagcagaa gcccggccag gcccccagac tgctgatcta ccgggccaac     600
agactggtgg acggcgtgcc cgatagattc agcggcagcg gctacggcac cgacttcacc     660
ctgaccatca caacatcga gtccgaggac gccgcctact acttctgcct gaagtacgac     720
gtgttcccct acaccttcgg ccagggcacc aaggtggaga tcaaggatct cgagcccaaa     780
tcttgtgaca aaactcacac atgcccaccg tgcccggatc ccaagttctg ggtgctggtg     840
gtcgtgggcg gagtgctggc ctgttacagc ctgctcgtga ccgtggcctt catcatcttt     900
tgggtgcgca gcaagcggag ccggctgctg cacagcgact acatgaacat gacccccaga     960
cggcctggcc ccaccagaaa gcactaccag ccttacgccc tcccagaga cttcgccgcc    1020 taccggtcca gagtgaagtt cagcagaagc gccgacgccc tgcctatca gcagggccag    1080 aaccagctgt acaacgagct gaacctgggc agacgggaag agtacgacgt gctggacaag    1140
cggagaggca gggaccctga tgggcggc aagcccagaa gaaagaaccc ccaggaaggc    1200
ctgtataacg aactgcagaa agacaagatg gccgaggcct acagcgagat cggcatgaag    1260
ggcgagcgga gaaagaggcaa gggccacgat ggcctgtacc agggactgag caccgccacc    1320
aaggacacct acgacgccct gcacatgcag gccctgcctc caagagcctc tagagccgag    1380
ggcagaggca gcctgctgac atgtggcgac gtggaagaga acccaggccc catgcctccc    1440
cccagactgc tgttcttcct gctgttcctg accctatgg aagtgcggcc cgaggaaccc    1500
ctggtcgtga aagtggaaga gggcgacaac gccgtgctgc agtgtctgaa gggcacctcc    1560
gatggcccta cccagcagct gacctggtcc agagagagcc ccctgaagcc cttcctgaag    1620
ctgtctctgg gctgcctgg cctgggcatc catatgaggc cactggccat ctggctgttc    1680
atcttcaacg tgtcccagca gatgggaggc ttctacctgt gccagcctgg cccaccttct    1740

-continued

```
gagaaggctt ggcagcctgg ctggaccgtg aacgtggaag gatctggcga gctgttccgg      1800
tggaacgtgt ccgatctggg cggcctggga tgcggcctga agaacagatc tagcgagggc      1860
cccagcagcc ccagcggcaa actgatgagc cccaagctgt acgtgtgggc caaggacaga      1920
cccgagattt gggagggcga gccccttgc ctgccccta gagatagcct gaaccagagc         1980
ctgagccagg acctgacaat ggcccctggc agcacactgt ggctgagctg tggcgtgcca      2040
cccgactctg tgtctagagg ccctctgagc tggacccacg tgcaccctaa gggccctaag      2100
agcctgctgt ccctggaact gaaggacgac aggcccgcca gagatatgtg ggtcatggaa      2160
accggcctgc tgctgcctag agccacagcc caggatgccg gcaagtacta ctgccacaga      2220
ggcaacctga ccatgagctt ccacctggaa atcaccgcca gacccgtgct gtggcactgg      2280
ctgctgagaa ccggcggatg gaaagtgtcc gccgtgactc tggcctacct gatcttctgc      2340
ctgtgctccc tcgtgggcat cctgcatctg cagagggctc tggtgctgcg gcggaagcgg      2400
aagagaatga ccgaccctac ccggcggttc taa                                     2433
```

<210> SEQ ID NO 30
<211> LENGTH: 19
<212> TYPE: PRT
<213> ORGANISM: Thosea asigna virus

<400> SEQUENCE: 30

```
Ala Glu Gly Arg Gly Ser Leu Leu Thr Cys Gly Asp Val Glu Glu Asn
1               5                   10                  15

Pro Gly Pro
```

<210> SEQ ID NO 31
<211> LENGTH: 18
<212> TYPE: PRT
<213> ORGANISM: Thosea asigna virus

<400> SEQUENCE: 31

```
Glu Gly Arg Gly Ser Leu Leu Thr Cys Gly Asp Val Glu Glu Asn Pro
1               5                   10                  15

Gly Pro
```

<210> SEQ ID NO 32
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Gly Ser Gly Ser Arg Val Thr Glu Leu Leu Tyr Arg Met Lys Arg Ala
1               5                   10                  15

Glu Thr Tyr Cys Pro Arg Pro Leu Leu Ala Ile His Pro Thr Glu Ala
            20                  25                  30

Arg His Lys Gln Lys Ile Val Ala Pro Val Lys Gln Leu Leu Asn Phe
        35                  40                  45

Asp Leu Leu Lys Leu Ala Gly Asp Val Glu Ser Asn Pro Gly Pro
    50                  55                  60
```

<210> SEQ ID NO 33
<211> LENGTH: 19
<212> TYPE: PRT
<213> ORGANISM: Amphimedon queenslandica

<400> SEQUENCE: 33

Leu Leu Cys Phe Leu Leu Leu Leu Leu Ser Gly Asp Val Glu Leu Asn
1               5                   10                  15

Pro Gly Pro

<210> SEQ ID NO 34
<211> LENGTH: 20
<212> TYPE: PRT
<213> ORGANISM: Amphimedon queenslandica

<400> SEQUENCE: 34

His His Phe Met Phe Leu Leu Leu Leu Leu Ala Gly Asp Ile Glu Leu
1               5                   10                  15

Asn Pro Gly Pro
            20

<210> SEQ ID NO 35
<211> LENGTH: 20
<212> TYPE: PRT
<213> ORGANISM: Saccoglossus kowalevskii

<400> SEQUENCE: 35

Trp Phe Leu Val Leu Leu Ser Phe Ile Leu Ser Gly Asp Ile Glu Val
1               5                   10                  15

Asn Pro Gly Pro
            20

<210> SEQ ID NO 36
<211> LENGTH: 20
<212> TYPE: PRT
<213> ORGANISM: Branchiostoma floridae

<400> SEQUENCE: 36

Lys Asn Cys Ala Met Tyr Met Leu Leu Leu Ser Gly Asp Val Glu Thr
1               5                   10                  15

Asn Pro Gly Pro
            20

<210> SEQ ID NO 37
<211> LENGTH: 20
<212> TYPE: PRT
<213> ORGANISM: Branchiostoma floridae

<400> SEQUENCE: 37

Met Val Ile Ser Gln Leu Met Leu Lys Leu Ala Gly Asp Val Glu Glu
1               5                   10                  15

Asn Pro Gly Pro
            20

<210> SEQ ID NO 38
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 39
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 40

Asp Xaa Glu Xaa Asn Pro Gly Pro
1               5

<210> SEQ ID NO 41
<211> LENGTH: 4109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
ccatatgaga tcttatatgg ggcacccccg ccccttgtaa acttccctga ccctgacatg      60
acaagagtta ctaacagccc ctctctccaa gctcacttac aggctctcta cttagtccag     120
cacgaagtct ggagacctct ggcggcagcc taccaagaac aactggaccg accggtggta     180
cctcaccctt accgagtcgg cgacacagtg tgggtccgcc gacaccagac taagaaccta     240
gaacctcgct ggaaaggacc ttacacagtc ctgctgacca cccccaccgc cctcaaagta     300
gacggcatcg cagcttggat acacgccgcc cacgtgaagg ctgccgaccc cggggggtgga    360 ccatcctcta gactgccatg gttctggccc agggcctgct gtctatggct ctgcttgctc     420
tgtgctggga gagaagtctg gctggcgccg aggaaacaat ccctctgcag accctgcggt     480
gctacaacga ctacaccagc cacatcacct gtagatgggc cgacacacag gacgcccaga     540
gactggtcaa tgtgaccctg atcagaagag tgaacgagga cctgctggaa cccgtgtcct     600
gtgacctgag cgacgatatg ccttggagcg cctgtcctca tctagatgt gtgcctcgga     660 gatgcgtgat ccctgccag agctttgtgg tcaccgatgt ggactacttc agcttccagc     720
ctgacagacc cctgggcacc agactgacag tgacactgac acagcacgtg cagcctccag     780
agcctaggga cctgcagatc tctaccgacc aggaccactt cctgctgact tggagtgtgg    840

-continued

```
ccctgggaag ccctcagtct cattggctta gccctggcga cctggaattc gaggtggtgt     900
acaagagact gcaggacagc tgggaagatg ccgccatcct gctgagcaat accagccagg     960
ctacactggg ccccgaacac ctgatgccta gctctaccta tgtggccaga gtgcggacaa    1020
gactggcccc tggatctaga ctgagcggca dacct
ctaa gtggtccct gaagtctgct    1080 gggatagcca gcctggggat gaagcccagc ctcagaacct ggaatgcttc ttcgatggcg    1140
ccgctgtgct gagctgttct tgggaagtgc ggaaagaggt ggccagcagc gttagcttcg    1200
gcctgttcta caagccctct ccagatgccg gatctgccgt gctgctgaga gaagaggaat    1260
gcagccccgt gctcagagaa ggcctgggat ctctgcacac cagacaccac tgtcagatcc    1320
ccgtgcctga tcctgccaca cacggccagt atatcgtgtc cgtgcagcca agaagggccg    1380
agaagcacat caagagcagc gtgaacatcc agatggcccc tccaagcctg aacgtgacca    1440
aggacggcga cagctacagc ctgagatggg agacaatgaa gatgcgctac gagcacatcg    1500
accacacctt cgagatccag taccggaagg ataccgccac ctggaaggac agcaagaccg    1560
agacactgca gaacgcccac tctatggcac tgccagctct cgagccctcc accagatatt    1620
gggccagagt cagagtgcgg accagcagaa caggctacaa cggcatttgg agcgagtgga    1680
gcgaagccag aagctgggat acagagtctg tactaccaat gtggggcgtg ctgctgtaca    1740
tcctgctggg cacaatcgga acactggtgg ctgtgctggc tgccagcgct ctgctgtata    1800
gacactggat cgagatcgtc ctgctgtacc ggacctacca gagcaaggat cagaccctgg    1860
gcgacaagaa ggacttcgac gcctttgtgt cctacgccaa gtggtccagc tttcccagcg    1920
aggccacaag cagcctgagc gaagaacatc tggccctgtc tctgttcccc gatgtgctgg    1980
aaaacaaata cggctacagc ctgtgcctgc tggaaagaga tgttgcccct ggcggagtgt    2040
acgccgagga tatcgtgtcc atcatcaagc ggagcagacg gggcatcttc attctgagcc    2100
ccaactacgt gaacggcccc agcatctttg aactgcaagc cgccgtgaac ctggctctgg    2160
acgatcagac actgaagctg atcctgatca agttctgcta cttccaagag cctgagagcc    2220
tgcctcacct ggtcaagaaa gccctgagag tgctgcctac cgtgacttgg agaggcctga    2280
agtccgtgcc tcctaacagc agattctggg ccaagatgag ataccacatg cctgtgaaga    2340
acagccaggg cttcacctgg aaccagctgc ggatcacctc cagaatcttc cagtggaagg    2400
gcctgagccg gaccgagaca acaggcagaa gcagccagcc taaagagtgg ggctccggag    2460
agggcagagg cagcctgctg acatgtggcg acgtggaaga gaacccaggc ccaatgctgc    2520
tgctggtcac atctctgctg ctgtgcgagc tgccccatcc tgcctttctg ctgatccccg    2580
agaagtccga cctgagaaca gtggcccctg ccagctctct gaacgttcgc ttcgacagcc    2640
ggaccatgaa cctgagctgg gactgccaag agaacacaac cttcagcaag tgcttcctga    2700
ccgacaagaa gaaccgggtc gtcgagccca gactgagcaa caatgagtgc tcctgcacct    2760
tcagagagat ctgcctgcac gagggcgtga ccttttgaggt gcacgtgaac acaagccagc    2820
ggggctttca gcagaagctg ctgtacccca atagcggcag agagggaacc gccgctcaga    2880
acttcagctg cttcatctac aacgccgacc tcatgaactg cacctgggcc agaggaccta    2940
ccgctcctag agatgtgcag tacttcctgt acattcggaa cagcaagcgg cggagagaaa    3000
tcaggtgccc ctactacatc caagacagcg gcacacacgt gggctgccac ctggataatc    3060
tgtctggcct gaccagccgg aactacttcc tggtcaatgg caccagccgc gagatcggca    3120
tccagttctt tgacagcctg ctggacacca agaagatcga gcggttcaac cctcctagca    3180
acgtgaccgt gcggtgcaac accacacatt gtctcgtgcg gtggaagcag ccccggacat    3240
```

-continued

```
accagaagct gagctacctg gacttccagt accagctgga tgtgcaccgg aagaacaccc      3300
agcctggcac cgagaacctg ctgatcaatg tgtccggcga cctggaaaac cggtacaact      3360
tccctagcag cgagcccagg gccaagcaca gcgtgaaaat tagagccgcc gatgtgcgca      3420
tcctgaactg gtcctcttgg agcgaggcca tcgagtttgg atccgacgac ggcatgatca      3480
ttgccgtgct gatcctggtg gccgtcgtgt gtctggtcac cgtgtgcgtg atctacagag      3540
tggacctggt gctgttctac cggcacctga ccagaaggga cgagacactg accgacggca      3600
agacctacga tgccttcgtg tcctacctga agagtgcag acccgagaac ggcgaggaac       3660
acaccttcgc cgtggaaatc ctgcctagag tgctggaaaa gcacttcggc tacaagctgt      3720
gcatcttcga gaggacgtt gtgcctggcg gagctgtggt ggatgagatc cacagcctga       3780
tcgagaagtc cagacggctg atcatcgtgc tgagcaagag ctacatgagc aacgaagtcc      3840
gctacgagct ggaaagcgga ctgcacgaag ccctggtgga acggaagatc aagatcatcc      3900
tgattgagtt caccccctgtg accgacttca cattcctgcc tcagagcctg aagctgctga     3960
agtcccacag agtgctgaag tggaaggccg acaagagcct gagctacaac agccggttct      4020
ggaagaacct gctgtacctg atgcctgcca agaccgtgaa gcccggcaga gatgaacctg      4080
aggtgctgcc tgtgctgagc gagtcttaa                                       4109
```

```
<210> SEQ ID NO 42
<211> LENGTH: 1766
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
ccatatgaga tcttatatgg ggcacccccg ccccttgtaa acttccctga ccctgacatg        60
acaagagtta ctaacagccc ctctctccaa gctcacttac aggctctcta cttagtccag       120
cacgaagtct ggagacctct ggcggcagcc taccaagaac aactggaccg accggtggta       180
cctcacccct accgagtcgg cgacacagtg tgggtccgcc gacaccagac taagaaccta       240
gaacctcgct ggaaaggacc ttacacagtc ctgctgacca cccccaccgc cctcaaagta       300
gacggcatcg cagcttggat acacgccgcc cacgtgaagg ctgccgaccc cgggggtgga       360
ccatcctcta gactgccatg gactggatct ggcgcatcct cttcctcgtc ggcgctgcta       420
ccggcgctca ttctgaggta caactgcagc agtctggacc tgaactgaag aagcctggag       480
agacagtcaa gatctcctgc aaggcctctg ggtatccttt cacaaactat ggaatgaact       540
gggtgaagca ggctccagga cagggtttaa agtggatggg ctggattaac acctccactg       600
gagagtcaac atttgctgat gacttcaagg gacggtttga cttctctttg gaaacctctg       660
ccaacactgc ctatttgcag atcaacaacc tcaaaagtga agacatggct acatatttct       720
gtgcaagatg ggaggtttac cacggctacg ttccttactg gggccaaggg accacggtca       780
ccgtttcctc tggcggtggc ggttctggtg gcggtggctc cggcggtggc ggttctgaca       840
tccagctgac ccagtctcac aaattcctgt ccacttcagt aggagacagg gtcagcatca       900
cctgcaaggc cagtcaggat gtgtataatg ctgttgcctg gtatcaacag aaaccaggac       960
aatctcctaa acttctgatt tactcggcat cctcccggta cactggagtc ccttctcgct      1020
tcactggcag tggctctggg ccggatttca ctttcaccat cagcagtgtg caggctgaag      1080
acctggcagt ttatttctgt cagcaacatt ttcgtactcc attcacgttc ggctcgggga      1140
```

-continued

```
caaaattgga gatcaaagct ctagatctcg agcccaaatc ttgtgacaaa actcacacat    1200
gcccaccgtg cccggatccc aaattttggg tgctggtggt ggttggtgga gtcctggctt    1260
gctatagctt gctagtaaca gtggccttta ttattttctg ggtgaggagt aagaggagca    1320
ggctcctgca cagtgactac atgaacatga ctccccgccg ccccgggccc acccgcaagc    1380
attaccagcc ctatgcccca ccacgcgact tcgcagccta tcgctccaga gtgaagttca    1440
gcaggagcgc agacgccccc gcgtaccagc agggccagaa ccagctctat aacgagctca    1500
atctaggacg aagagaggag tacgatgttt tggacaagag acgtggccgg gaccctgaga    1560 tgggggggaaa gccgagaagg aagaaccctc aggaaggcct gtacaatgaa ctgcagaaag    1620
ataagatggc ggaggcctac agtgagattg ggatgaaagg cgagcgccgg aggggcaagg    1680
ggcacgatgg cctttaccag ggtctcagta cagccaccaa ggacacctac gacgcccttc    1740
acatgcaggc cctgccccct cgctaa                                          1766
```

<210> SEQ ID NO 43
<211> LENGTH: 2810
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
ccatatgaga tcttatatgg ggcacccccg ccccttgtaa acttccctga ccctgacatg       60
acaagagtta ctaacagccc ctctctccaa gctcacttac aggctctcta cttagtccag      120
cacgaagtct ggagacctct ggcggcagcc taccaagaac aactggaccg accggtggta      180 cctcacccctt accgagtcgg cgacacagtg tgggtccgcc gacaccagac taagaaccta      240
gaacctcgct ggaaaggacc ttacacagtc ctgctgacca cccccaccgc cctcaaagta      300
gacggcatcg cagcttggat acacgccgcc cacgtgaagg ctgccgaccc cggggggtgga      360 ccatcctcta gactgccatg gactggatct ggcggattct gttcctcgtg ggagccgcca      420
caggcgctca ctcacaggtg cagctgctgg aatctggcgg cggactggtg cagcctggcg      480
gcagcctgag actgagctgc gccgccagcg gcttcacctt cagcagctac accatgagct      540
gggtccggca ggctcctgga caggccctgg aatggatggg caccatcagc agcggcggca      600
cctacaccta ctaccccgac agcgtgaagg gccggttcac catcagccgg gacaacgcca      660
agaacagcct gtacctgcag atgaacagcc tgagagccga ggacacagcc gtgtactact      720
gcgccagaga ggccatcttc acctactggg gcagaggcac cctggtcaca agcagcggag      780
gcggaggaag tggaggggga ggatcaggcg gcggaggcag cgatatccag ctgacccaga      840
gccctagcag cctgagcgcc agcgtgggcg acagagtgac catcacatgc aaggccagcc      900
aggacatcaa caactacctg agctggtatc agcagaagcc cggccaggcc cccgactgc       960 tgatctaccg ggccaacaga ctggtggacg gcgtgcccga tagattcagc ggcagcggct    1020
acggcaccga cttcaccctg accatcaaca catcgagtc cgaggacgcc gcctactact    1080
tctgcctgaa gtacgacgtg ttcccctaca ccttcggcca gggcaccaag gtggagatca    1140
aggatctcga gcccaaatct tgtgacaaaa ctcacacatg cccaccgtgc ccggatccca    1200
agttctgggt gctggtggtc gtgggcggag tgctggcctg ttacagcctg ctcgtgaccg    1260
tggccttcat catcttttgg gtgcgcagca agcggagccg gctgctgcac agcgactaca    1320
tgaacatgac ccccagacgg cctggcccca ccagaaagca ctaccagcct tacgcccctc    1380
```

```
ccagagactt cgccgcctac cggtccagag tgaagttcag cagaagcgcc gacgcccctg    1440
cctatcagca gggccagaac cagctgtaca acgagctgaa cctgggcaga cgggaagagt    1500
acgacgtgct ggacaagcgg agaggcaggg accctgagat gggcggcaag cccagaagaa    1560 agaacccca  ggaaggcctg tataacgaac tgcagaaaga caagatggcc gaggcctaca    1620
gcgagatcgg catgaagggc gagcggagaa gaggcaaggg ccacgatggc ctgtaccagg    1680
gactgagcac cgccaccaag gacacctacg acgccctgca catgcaggcc ctgcctccaa    1740
gagcctctag agccgagggc agaggcagcc tgctgacatg tggcgacgtg gaagagaacc    1800
caggccccat gcctccccc  agactgctgt tcttcctgct gttcctgacc cctatggaag    1860
tgcggcccga ggaacccctg gtcgtgaaag tggaagaggg cgacaacgcc gtgctgcagt    1920
gtctgaaggg cacctccgat ggccctaccc agcagctgac ctggtccaga gagagccccc    1980
tgaagcccct cctgaagctg tctctgggcc tgcctggcct gggcatccat atgaggccac    2040
tggccatctg gctgttcatc ttcaacgtgt cccagcagat gggaggcttc tacctgtgcc    2100
agcctggccc accttctgag aaggcttggc agcctggctg gaccgtgaac gtggaaggat    2160
ctggcgagct gttccggtgg aacgtgtccg atctgggcgg cctgggatgc ggcctgaaga    2220
acagatctag cgagggcccc agcagcccca gcggcaaact gatgagcccc aagctgtacg    2280
tgtgggccaa ggacagaccc gagatttggg agggcgagcc cccttgcctg cccctagag     2340 atagcctgaa ccagagcctg agccaggacc tgacaatggc ccctggcagc acactgtggc    2400
tgagctgtgg cgtgccaccc gactctgtgt ctagaggccc tctgagctgg acccacgtgc    2460
accctaaggg ccctaagagc ctgctgtccc tggaactgaa ggacgacagg cccgccagag    2520
atatgtgggt catggaaacc ggcctgctgc tgcctagagc cacagcccag gatgccggca    2580
agtactactg ccacagaggc aacctgacca tgagcttcca cctggaaatc accgccagac    2640
ccgtgctgtg gcactggctg ctgagaaccg gcggatggaa agtgtccgcc gtgactctgg    2700
cctacctgat cttctgcctg tgctccctcg tgggcatcct gcatctgcag agggctctgg    2760
tgctgcggcg gaagcggaag agaatgaccg accctacccg gcggttctaa               2810
```

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Met Asp Trp Ile Trp Arg Ile Leu Phe Leu Val Gly Ala Ala Thr Gly
1               5                   10                  15

Ala His Ser
```

<210> SEQ ID NO 45
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

```
atggactgga tctggcgcat cctcttcctc gtcggcgctg ctaccggcgc tcattct       57
```

```
<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Met Ala Leu Pro Val Thr Ala Leu Leu Leu Pro Leu Ala Leu Leu Leu
1               5                   10                  15

His Ala Ala Arg Pro
            20

<210> SEQ ID NO 47
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atggccttac cagtgaccgc cttgctcctg ccgctggcct tgctgctcca cgccgccagg      60
ccg                                                                    63

<210> SEQ ID NO 48
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asn Leu Gly Ser Val Tyr Ile Tyr Val Leu Leu Ile Val Gly Thr Leu
1               5                   10                  15

Val Cys Gly Ile Val Leu Gly Phe Leu Phe
            20                  25

<210> SEQ ID NO 49
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
aacctcggct ctgtgtacat ttatgtgctc ctaatcgtgg gaacccttgt ctgtggcatc      60
gtcctcggct tcctcttt                                                     78

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Val Leu Ala Leu Ile Val Ile Phe Leu Thr Ile Ala Val Leu Leu Ala
1               5                   10                  15

Leu
```

<210> SEQ ID NO 51
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gtgctggccc tcatcgtgat cttcctcacc atcgctgtgc tcctggccct c                51

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Thr Tyr Gln Lys Leu Ser Tyr Leu Asp Phe
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Asp Val Arg Ile Leu Asn
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Cys Gln Ser Phe Val Val Thr Asp
1               5

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Met Lys Met Arg Tyr Glu His Ile Asp
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Ser Arg Thr Gly Tyr Asn Gly
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Glu Asn Leu Leu
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Tyr Asn Phe Pro Ser Ser
1               5

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Glu His Ile Asp
1

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Thr Leu Gln Asn Ala His Ser Met Ala Leu Pro
1               5                   10

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Leu Asn Val Thr Lys Asp Gly Asp Ser Tyr Ser Leu Arg Trp Glu
1               5                   10                  15

Thr

<210> SEQ ID NO 62
<211> LENGTH: 12
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Glu Trp Ser Glu Ala Arg Ser Trp Asp Thr Glu Ser
1               5                   10
```